US012774289B2

(12) United States Patent
Brown et al.

(10) Patent No.: US 12,774,289 B2
(45) Date of Patent: Oct. 27, 2026

(54) H4 ANTAGONIST COMPOUNDS

(71) Applicant: NXERA PHARMA UK LIMITED, Cambridge (GB)

(72) Inventors: Giles Albert Brown, Cambridge (GB); Miles Stuart Congreve, Cambridge (GB); Barry Teobald, Cambridge (GB); Nigel Alan Swain, Cambridge (GB); Charlotte Fieldhouse, Cambridge (GB); Mark Pickworth, Cambridge (GB); Malken Bayrakdarian, Quebec (CA); Delphine Karila, Quebec (CA); Daniel Beaudoin, Quebec (CA)

(73) Assignee: NXERA PHARMA UK LIMITED (GB)

( * ) Notice: Subject to any disclaimer, the term of this patent is extended or adjusted under 35 U.S.C. 154(b) by 501 days.

(21) Appl. No.: 18/257,413

(22) PCT Filed: Dec. 14, 2021

(86) PCT No.: PCT/GB2021/053286
§ 371 (c)(1),
(2) Date: Jun. 14, 2023

(87) PCT Pub. No.: WO2022/129890
PCT Pub. Date: Jun. 23, 2022

(65) Prior Publication Data

US 2024/0317775 A1 Sep. 26, 2024

(30) Foreign Application Priority Data

Dec. 14, 2020 (GB) ...................................... 2019667

(51) Int. Cl.
*C07D 498/04* (2006.01)
*A61K 31/5383* (2006.01)
*A61K 31/553* (2006.01)
*C07D 498/14* (2006.01)

(52) U.S. Cl.
CPC ........ *C07D 498/04* (2013.01); *A61K 31/5383* (2013.01); *A61K 31/553* (2013.01); *C07D 498/14* (2013.01)

(58) Field of Classification Search
CPC ................ C07D 498/04; C07D 498/14; A61K 31/5383; A61K 31/553
See application file for complete search history.

(56) References Cited

U.S. PATENT DOCUMENTS

| | | | | |
|---|---|---|---|---|
| 4,748,175 | A | 5/1988 | Kasztreiner et al. | |
| 7,384,937 | B2 * | 6/2008 | Barbosa ............... | C07D 487/04 514/224.2 |
| 9,580,443 | B2 * | 2/2017 | Lan ......................... | A61P 35/00 |
| 9,850,255 | B2 * | 12/2017 | Lan .......................... | A61N 5/10 |
| 10,287,300 | B2 * | 5/2019 | Lan ...................... | C07D 487/04 |

FOREIGN PATENT DOCUMENTS

| | | | |
|---|---|---|---|
| CN | 104583215 | B | 12/2016 |
| EP | 1103551 | A1 | 5/2001 |
| RU | 2489430 | C2 | 8/2013 |
| RU | 2573828 | C2 | 1/2016 |
| SU | 1567122 | A3 | 5/1990 |
| WO | 2005054239 | A1 | 6/2005 |
| WO | 2007072163 | A2 | 6/2007 |
| WO | 2008031556 | A2 | 3/2008 |
| WO | 2008060766 | A2 | 5/2008 |
| WO | 2009068512 | A1 | 6/2009 |
| WO | 2009077608 | A1 | 6/2009 |
| WO | 2009080721 | A2 | 7/2009 |
| WO | 2010059658 | A1 | 5/2010 |
| WO | 2010108059 | A1 | 9/2010 |
| WO | WO 2011/059839 | | 5/2011 |
| WO | 2011076878 | A1 | 6/2011 |

(Continued)

OTHER PUBLICATIONS

International Search Report mailed Mar. 22, 2022 in International Application No. PCT/GB2021/053286, filed on Dec. 14, 2021.
Kasztreiner, E., et al. "Synthesis and positive inotropic activity of novel pyrimido-[5, 4-b][1, 4] oxazin-7 (8H)-ones." European journal of medicinal chemistry 25.4 (1990): 333-341.
Andaloussi, Mounir, et al. "A novel series of histamine H4 receptor antagonists based on the pyrido [3, 2-d] pyrimidine scaffold: comparison of hERG binding and target residence time with PF-3893787." Bioorganic & medicinal chemistry letters 23.9 (2013): 2663-2670.
Altenbach, Robert J., et al. "Structure—activity studies on a series of a 2-aminopyrimidine-containing histamine H4 receptor ligands." Journal of medicinal chemistry 51.20 (2008): 6571-6580.
Beasley, Richard, Alex Semprini, and Edwin A. Mitchell. "Risk factors for asthma: is prevention possible?." The Lancet 386.9998 (2015): 1075-1085.

(Continued)

*Primary Examiner* — Andrew D Kosar
(74) *Attorney, Agent, or Firm* — Barnes & Thornburg; Amy H. Fix; Lisa M. Seaney

(57) ABSTRACT

The disclosures herein relate to novel compounds of formula (1):

(1)

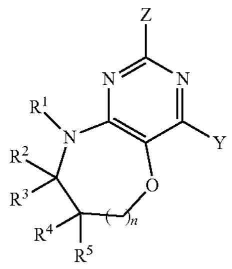

and salts thereof, wherein Y, Z, $R^1$, $R^2$, $R^3$, $R^4$, $R^5$ and n are defined herein, and their use in treating, preventing, ameliorating, controlling or reducing the risk of disorders associated with H4 receptors.

25 Claims, 1 Drawing Sheet

(56) References Cited

FOREIGN PATENT DOCUMENTS

| | | | |
|---|---|---|---|
| WO | 2014033196 A1 | 3/2014 | |
| WO | WO 2014/078637 | 5/2014 | |
| WO | WO 2018/023029 | 2/2018 | |
| WO | 2020079457 A1 | 4/2020 | |

OTHER PUBLICATIONS

Correa, Michelle Fidelis, and João Paulo dos Santos Fernandes. "Histamine H4 receptor ligands: future applications and state of art." Chemical Biology & Drug Design 85.4 (2015): 461-480.
International Search Report Issued for International Application No. PCT/GB2019/052997 mailed Nov. 26, 2019.
Ko, Kwangseok, et al. "Discovery of a novel highly selective histamine H4 receptor antagonist for the treatment of atopic dermatitis." Journal of Medicinal Chemistry 61.7 (2018): 2949-2961.
Mollanazar, Nicholas K., Peter K. Smith, and Gil Yosipovitch. "Mediators of chronic pruritus in atopic dermatitis: getting the itch out?." Clinical reviews in allergy & immunology 51 (2016): 263-292.
Mowbray, Charles E., et al. "Challenges of drug discovery in novel target space. The discovery and evaluation of PF-3893787: a novel histamine H4 receptor antagonist." Bioorganic & medicinal chemistry letters 21.21 (2011): 6596-6602.
Savall, Brad M., et al. "Discovery and SAR of 6-alkyl-2, 4-diaminopyrimidines as histamine H4 receptor antagonists." Journal of medicinal chemistry 57.6 (2014): 2429-2439.
Thurmond, R. L., et al. "Pharmacology and clinical activity of toreforant, a histamine H4 receptor antagonist." Ann Pharmacol Pharm 2.2 (2017): 1013.
Venable, Jennifer D., et al. "Preparation and biological evaluation of indole, benzimidazole, and thienopyrrole piperazine carboxamides: potent human histamine H4 antagonists." Journal of medicinal chemistry 48.26 (2005): 8289-8298.
Walter, Miriam, Tim Kottke, and Holger Stark. "The histamine H4 receptor: targeting inflammatory disorders." European journal of pharmacology 668.1-2 (2011): 1-5.

* cited by examiner

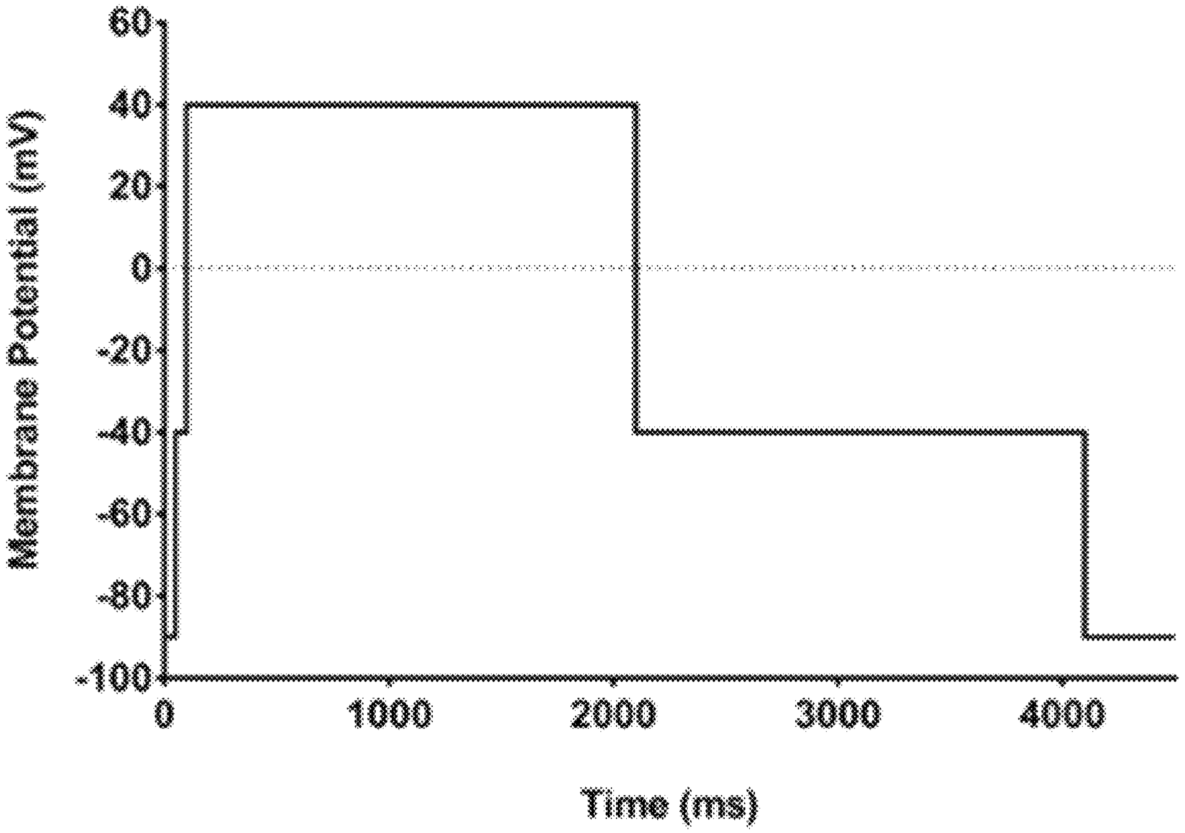
60
40
20
0
-20
-40
-60
-80
-100
Membrane Potential (mV)
0
1000
2000
3000
4000
Time (ms)

H4 ANTAGONIST COMPOUNDS

CROSS-REFERENCE TO RELATED APPLICATIONS

The present application is a 371 (National Stage) of PCT/GB2021/053286, filed Dec. 14, 2021, which claims benefit of GB 2019667.1 filed on Dec. 14, 2020.

This application relates to novel compounds and their use as Histamine H4 receptor antagonists. Compounds described herein may be useful in the treatment or prevention of diseases in which H4 receptors are involved. The application is also directed to pharmaceutical compositions comprising these compounds and the manufacture and use of these compounds and compositions in the prevention or treatment of such diseases in which H4 receptors are involved.

BACKGROUND OF THE INVENTION

Histamine is a short-acting biogenic amine generated in mast cells where it is stored in cytosolic granules and released in response to various immunological and non-immunological stimuli. Histamine release from mast cells has been traditionally associated with mild to severe signs and symptoms that characterize hypersensitivity reactions, including erythema, urticaria, itching, tachycardia, hypotension, ventricular fibrillations, bronchospasm, and cardiac and respiratory arrest. To date, numerous additional sources have been identified, including basophils, neurons and cancer cells. In addition to modulating a wide range of physiological processes, histamine is implicated in pathological conditions including allergies and anaphylaxis, asthma and chronic inflammation, autoimmune, cardiovascular, neuropsychiatric and endocrine disorders as well as cancer.

Histamine exerts its pleiotropic actions mainly through binding to four types of G-protein-coupled receptors (GPCRs), designated as H1-H4 that are differentially expressed in various cell types and exhibit considerable variations among species. The H2 receptor is responsible for gastric acid secretion; the H3 receptor controls the release of histamine and other neuromodulators in the CNS and the H1 receptor is associated with wakefulness and inflammatory response.

Identified in 2000, the high affinity H4 receptor displays constitutive activity and is expressed mostly, but not exclusively on cells of the immune system including mast cells, monocytes, dendritic cells, eosinophils, basophils, neutrophils, and T cells. This discovery led to the attractive prospect of a new drug target with therapeutic potential in acute and chronic inflammation, autoimmune disease, host defense and neuropathic pain.

The H4R shares only 40% homology with its nearest neighbour the H3R and neither H2 nor H1 antagonists were shown to inhibit histamine induced eosinophil chemotaxis. Histamine has been shown to inhibit forskolin-induced cAMP responses in a pertussis toxin (PTx)-sensitive manner, suggesting that H4R signals via heterotrimeric Gai/o proteins. Transient expression of the H4R in heterologous cell systems (e.g. HEK293 cells) is a widely used method to measure H4 ligand signaling and binding to generate estimates of functional potency and receptor affinity respectively.

The discovery of H4R antagonists using these techniques and their study in various animal disease models including asthma, chronic pruritus, dermatitis, rheumatoid arthritis, gastric ulcerogenesis and colitis has confirmed H4R antagonism leads to a profound anti-inflammatory effect and has validated the therapeutic benefit for targeting this receptor. The first H4R antagonist phase 2a clinical trial in patients suffering from moderate-to-severe atopic dermatitis has already been conducted, further confirming H4 as a druggable target in patients Notwithstanding a number of published H4R ligands, there remains a need to develop new H4R antagonists with good drug candidate quality. These antagonists should display excellent low nM potency and affinity with full selectivity against H1-H3 receptors. They should display no agonist activity due to risks associated with the induction of pro-inflammatory responses, and ideally display a similar pharmacological profile across species to support PK/PD in various animal models of disease. They should be metabolically stable, with excellent PK, non-toxic and show excellent H4 specificity in broad safety panel profiling.

The human ether-a-go-go-related gene (hERG) encodes the pore-forming subunit of the rapidly activating delayed rectifier potassium channel (IKr), which plays an important role in ventricular repolarisation and in determining the QT-interval of the electrocardiogram with QT-interval being the time taken for ventricular depolarisation and repolarisation. It is widely acknowledged that hERG is highly susceptible to inhibition by a wide range of structurally diverse compounds. When the channels ability to conduct electrical current across the cell membrane is inhibited or compromised by application of drugs, it can result in a potentially fatal disorder called QT syndrome. A number of clinically successful drugs in the market have had the tendency to inhibit hERG, and create a concomitant risk of sudden death, as a side-effect, which has made hERG inhibition an important anti-target that must be avoided during drug development.

Compounds of the invention are antagonists of the H4 receptor. Certain compounds have a low hERG inhibition, making these particularly beneficial.

THE INVENTION

The present invention provides compounds having activity as H4 receptor antagonists. More particularly, the invention provides compounds that combine H4 receptor antagonism with low hERG activity.

Accordingly, in one embodiment the invention provides a compound of the formula (1):

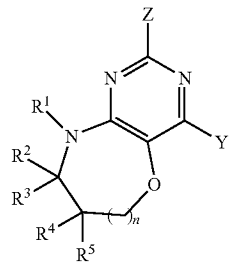

or a salt thereof, wherein;

Z is H, $NH_2$ or $C_{1-3}$ alkyl;

Y is selected from the group consisting of:

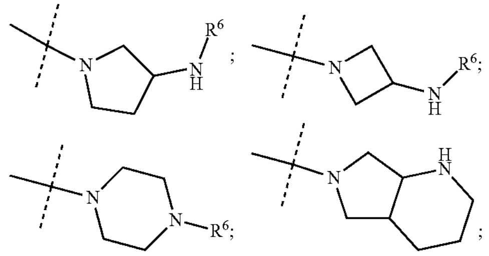

n is 0 or 1;

$R^1$ is H or $C_{1-3}$ alkyl optionally substituted with 1 to 6 fluorine atoms, or is joined to $R^3$ to form a ring which is optionally substituted with 1 to 6 fluorine atoms;

$R^2$ is H, optionally substituted $C_{1-6}$ alkyl, optionally substituted $C_{3-6}$ cycloalkyl, or an optionally substituted 3 to 6-membered heterocyclyl group, wherein the optional substituents are selected from $OC_{1-3}$ alkyl or 1 to 6 fluorine atoms, or $R^2$ is joined to $R^3$ to form a ring which is optionally substituted with 1 to 6 fluorine atoms;

$R^3$ is H or $C_{1-3}$ alkyl optionally substituted with 1 to 6 fluorine atoms, or is joined to $R^1$ to form a ring which is optionally substituted with 1 to 6 fluorine atoms, or is joined to $R^2$ to form a ring which is optionally substituted with 1 to 6 fluorine atoms, or is joined to $R^4$ to form a ring which is optionally substituted with 1 to 6 fluorine atoms;

$R^4$ is H or $C_{1-3}$ alkyl optionally substituted with 1 to 6 fluorine atoms, or is joined to $R^3$ to form a ring which is optionally substituted with 1 to 6 fluorine atoms, or is joined to $R^5$ to form a ring which is optionally substituted with 1 to 6 fluorine atoms;

$R^5$ is H or $C_{1-3}$ alkyl optionally substituted with 1 to 6 fluorine atoms, or is joined to $R^4$ to form a ring which is optionally substituted with 1 to 6 fluorine atoms;

and $R^5$ is H or methyl.

Particular compounds include compounds of formula (1a) and (1b):

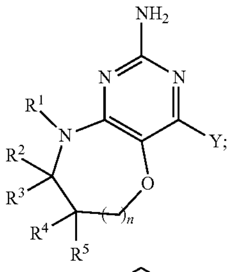

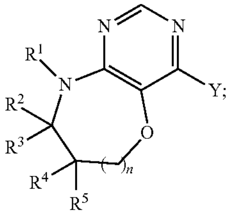

or salts thereof, wherein Y, $R^1$, $R^2$, $R^3$, $R^4$, $R^5$ and n are as defined above.

Particular compounds include compounds of formula (2a) and (2b):

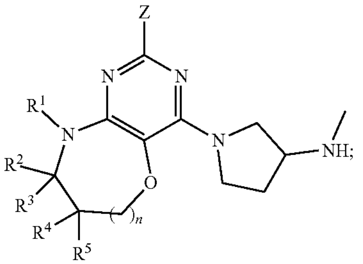

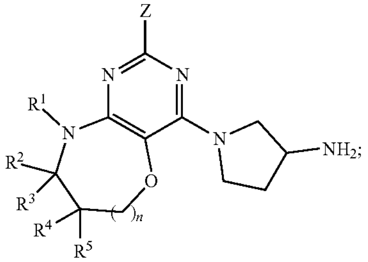

or salts thereof, wherein Z, $R^1$, $R^2$, $R^3$, $R^4$, $R^5$ and n are as defined above.

Particular compounds include compounds of formula (2c) and (2d):

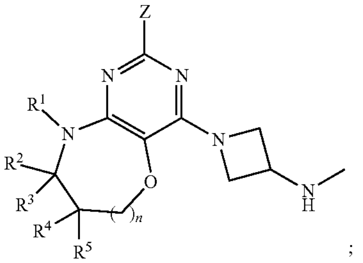

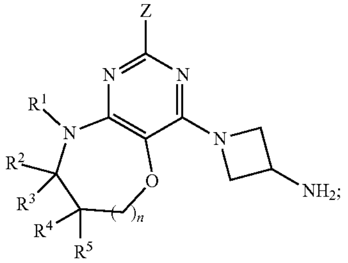

or salts thereof, wherein Z, $R^1$, $R^2$, $R^3$, $R^4$, $R^5$ and n are as defined above.

Particular compounds include a compound of formula (2e):

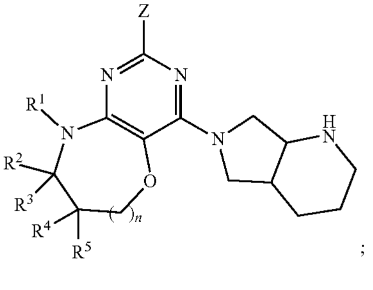

or a salt thereof, wherein Z, $R^1$, $R^2$, $R^3$, $R^4$, $R^5$ and n are as defined above.

Particular compounds include compounds of formula (3a) and (3b):

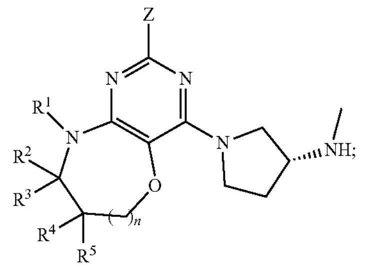

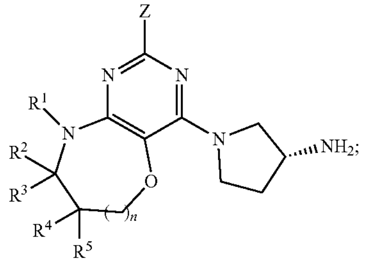

or salts thereof, wherein Z, $R^1$, $R^2$, $R^3$, $R^4$, $R^5$ and n are as defined above.

Particular compounds include a compound of formula (3c):

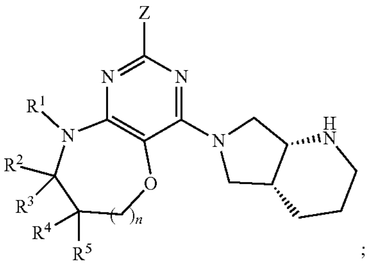

;

or a salt thereof, wherein Z, $R^1$, $R^2$, $R^3$, $R^4$, $R^5$ and n are as defined above.

Particular compounds include a compound of formula (4):

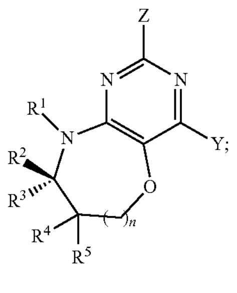

or a salt thereof, wherein Y, Z, $R^1$, $R^2$, $R^3$, $R^4$, $R^5$ and n are as defined above.

Particular compounds include a compound of formula (5):

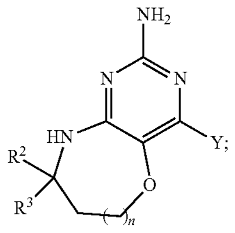

or a salt thereof, wherein Y, $R^2$, $R^3$ and n are as defined above.

Particular compounds include a compound of formula (5a):

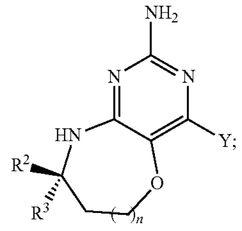

or a salt thereof, wherein Y, $R^2$, $R^3$ and n are as defined above.

Particular compounds include a compound of formula (6a) and (6b):

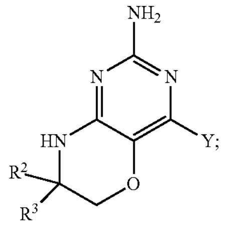

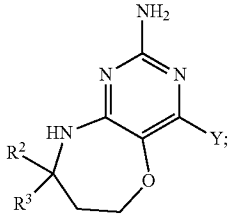

or a salt thereof, wherein Y, $R^2$ and $R^3$ are as defined above.

Particular compounds include a compound of formula (7a) and (7b):

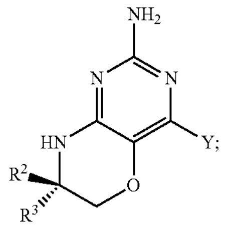

-continued

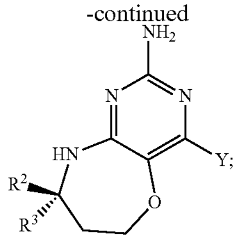

or a salt thereof, wherein Y, $R^2$ and $R^3$ are as defined above.

The compounds may be used as H4 receptor antagonists. The compounds may be used in the manufacture of medicaments. The compounds or medicaments may be for use in treating, preventing, ameliorating, controlling or reducing the risk of inflammatory disorders including asthma, chronic pruritus, dermatitis, rheumatoid arthritis, gastric ulcerogenesis and colitis.

BRIEF DESCRIPTION OF DRAWINGS

FIG. 1 depicts a schematic of the QPatch voltage protocol used for the hERG assay.

DETAILED DESCRIPTION OF THE INVENTION

The invention relates to novel compounds. The invention also relates to the use of novel compounds as antagonists of the H4 receptor. The invention further relates to the use of novel compounds in the manufacture of medicaments for use as H4 receptor antagonists or for the treatment of H4 system dysfunction. The invention further relates to compounds, compositions and medicaments which are selective H4 receptor antagonists.

The invention further relates to compounds, compositions and medicaments useful for the treatment of acute and chronic inflammation, autoimmune disease, host defense disorders and neuropathic pain.

The invention further relates to compounds, compositions and medicaments useful for the treatment of inflammatory disorders including asthma, chronic pruritus, dermatitis, rheumatoid arthritis, gastric ulcerogenesis and colitis.

Compounds of the invention include compounds according to formula (1):

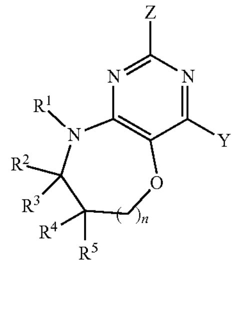

or a salt thereof, wherein;

Z is H, $NH_2$ or $C_{1-3}$ alkyl;

Y is selected from the group consisting of:

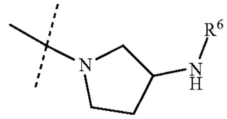
;
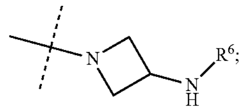

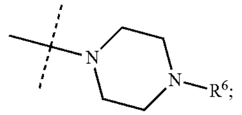
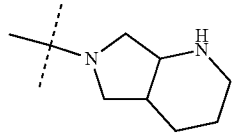
;

n is 0 or 1;

$R^1$ is H or $C_{1-3}$ alkyl optionally substituted with 1 to 6 fluorine atoms, or is joined to $R^3$ to form a ring which is optionally substituted with 1 to 6 fluorine atoms;

$R^2$ is H, optionally substituted $C_{1-6}$ alkyl, optionally substituted $C_{3-6}$ cycloalkyl, or an optionally substituted 3 to 6-membered heterocyclyl group, wherein the optional substituents are selected from $OC_{1-3}$ alkyl or 1 to 6 fluorine atoms, or $R^2$ is joined to $R^3$ to form a ring which is optionally substituted with 1 to 6 fluorine atoms;

$R^3$ is H or $C_{1-3}$ alkyl optionally substituted with 1 to 6 fluorine atoms, or is joined to R, to form a ring which is optionally substituted with 1 to 6 fluorine atoms, or is joined to $R^2$ to form a ring which is optionally substituted with 1 to 6 fluorine atoms, or is joined to $R^4$ to form a ring which is optionally substituted with 1 to 6 fluorine atoms;

$R^4$ is H or $C_{1-3}$ alkyl optionally substituted with 1 to 6 fluorine atoms, or is joined to $R^3$ to form a ring which is optionally substituted with 1 to 6 fluorine atoms, or is joined to $R^5$ to form a ring which is optionally substituted with 1 to 6 fluorine atoms;

$R^5$ is H or $C_{1-3}$ alkyl optionally substituted with 1 to 6 fluorine atoms, or is joined to $R^4$ to form a ring which is optionally substituted with 1 to 6 fluorine atoms;

and $R^6$ is H or methyl.

In the compounds herein, Z can be H. Z can be $NH_2$. Z can be $C_{1-3}$ alkyl. Z can be methyl.

In the compounds herein, Y can be an optionally substituted 3-aminopyrrolidine ring. Y can be an optionally substituted 3-aminoazetidine ring. Y can be an optionally substituted piperazine ring. Y can be an optionally substituted octahydro-1H-pyrrolo[3,4-b]pyridine ring system. Y can be 3-aminopyrrolidine. Y can be 3-aminoazetidine. Y can be piperazine. Y can be octahydro-1H-pyrrolo[3,4-b]pyridine. Y can be N-methylazetidin-3-amine. Y can be N-methylpyrrolidin-3-amine. Y can be N-methylpiperazine. Y can be (3R)-N-methylpyrrolidin-3-amine. Y can be (3R)-pyrrolidin-3-amine. Y can be (4aR,7aR)-octahydro-1H-pyrrolo[3,4-b]pyridine.

Y can be

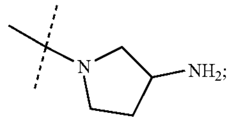
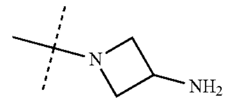
;

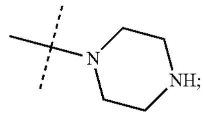
or
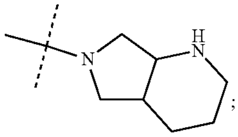
;

Y can be:

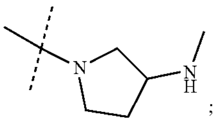
;
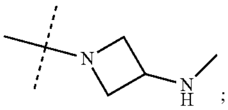
; or
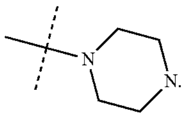

Y can be:

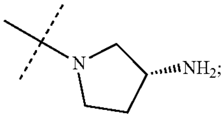
; or
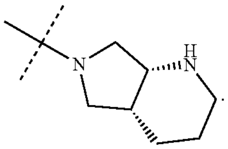

Y can be:

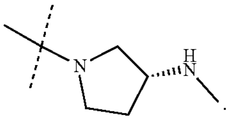

In the compounds herein, $R^1$ can be H or $C_{1-3}$ alkyl optionally substituted with 1 to 6 fluorine atoms. $R^1$ can be H or methyl. $R^1$ can be H. $R^1$ can be $C_{1-3}$ alkyl. $R^1$ can be joined to $R^3$ to form a ring which is optionally substituted with 1 to 6 fluorine atoms. $R^1$ can be methyl. $R^1$ can be joined to $R^3$ to form a 3 to 6-membered ring which is optionally substituted with 1 to 6 fluorine atoms. $R^1$ can be joined to $R^3$ to form a 5-membered ring which is optionally substituted with 1 to 6 fluorine atoms. $R^1$ can be joined to $R^3$ to form a 3 to 6-membered heterocycloalkyl ring which is optionally substituted with 1 to 6 fluorine atoms. $R^1$ can be joined to $R^3$ to form a 5-membered heterocycloalkyl ring which is optionally substituted with 1 to 6 fluorine atoms.

In the compounds herein, $R^2$ can be H, optionally substituted $C_{1-6}$ alkyl, optionally substituted $C_{3-6}$ cycloalkyl or an optionally substituted 3 to 6-membered heterocyclyl group, wherein the optional substituents are selected from OMe or 1 to 3 fluorine atoms, or $R^2$ is joined to $R^3$ to form a ring which is optionally substituted with 1 to 6 fluorine atoms. $R^2$ can be selected from the group consisting of H, methyl, ethyl, isopropyl, cyclopropyl, isobutyl, trifluoromethyl, $CH_2OMe$, $CH(CH_3)OMe$, $C(CH_3)_2OMe$ and oxetanyl. $R^2$ can be H. $R^2$ can be methyl. $R^2$ can be ethyl. $R^2$ can be isopropyl. $R^2$ can be cyclopropyl. $R^2$ can be isobutyl. $R^2$ can be trifluoromethyl. $R^2$ can be $CH_2OMe$. $R^2$ can be $CH(CH_3)OMe$. $R^2$ can be $C(CH_3)_2OMe$. $R^2$ can be oxetanyl. $R^2$ can be joined to $R^3$ to form a 3 to 6-membered ring which is optionally substituted with 1 to 6 fluorine atoms. $R^2$ can be joined to $R^3$ to form a 5-membered ring which is optionally substituted with 1 to 6 fluorine atoms. $R^2$ can be joined to $R^3$ to form a 4-membered ring which is optionally substituted with 1 to 6 fluorine atoms. $R^2$ can be joined to $R^3$ to form a 3 to 6-membered cycloalkyl ring which is optionally substituted with 1 to 6 fluorine atoms. $R^2$ can be joined to $R^3$ to form a 5-membered cycloalkyl ring which is optionally substituted with 1 to 6 fluorine atoms. $R^2$ can be joined to $R^3$ to form a 4-membered cycloalkyl ring which is optionally substituted with 1 to 6 fluorine atoms.

In the compounds herein, $R^3$ can be H or $C_{1-3}$ alkyl optionally substituted with 1 to 6 fluorine atoms. $R^3$ can be H. $R^3$ can be $C_{1-3}$ alkyl. $R^3$ can be joined to $R^1$ to form a ring which is optionally substituted with 1 to 6 fluorine atoms. $R^3$ can be joined to $R^2$ to form a ring which is optionally substituted with 1 to 6 fluorine atoms. $R^3$ can be joined to $R^4$ to form a ring which is optionally substituted with 1 to 6 fluorine atoms. $R^3$ can be methyl. $R^3$ can be joined to $R^1$ to form a 3 to 6-membered ring which is optionally substituted with 1 to 6 fluorine atoms. $R^3$ can be joined to $R^2$ to form a 3 to 6-membered ring which is optionally substituted with 1 to 6 fluorine atoms. $R^3$ can be joined to $R^4$ to form a 3 to 6-membered ring which is optionally substituted with 1 to 6 fluorine atoms. $R^3$ can be joined to $R^1$ to form a 5-membered ring which is optionally substituted with 1 to 6 fluorine atoms. $R^3$ can be joined to $R^2$ to form a 5-membered ring which is optionally substituted with 1 to 6 fluorine atoms. $R^3$ can be joined to $R^2$ to form a 4-membered ring which is optionally substituted with 1 to 6 fluorine atoms. $R^3$ can be joined to $R^1$ to form a 3 to 6-membered heterocycloalkyl ring which is optionally substituted with 1 to 6 fluorine atoms. $R^3$ can be joined to $R^2$ to form a 3 to 6-membered cycloalkyl ring which is optionally substituted with 1 to 6 fluorine atoms. $R^3$ can be joined to $R^4$ to form a 3 to 6-membered cycloalkyl ring which is optionally substituted with 1 to 6 fluorine atoms. $R^3$ can be joined to $R^1$ to form a heterocycloalkyl ring which is optionally substituted with 1 to 6 fluorine atoms. $R^3$ can be joined to $R^2$ to form a cycloalkyl ring which is optionally substituted with 1 to 6 fluorine atoms. $R^3$ can be joined to $R^4$ to form a cycloalkyl ring which is optionally substituted with 1 to 6 fluorine atoms. $R^3$ can be joined to $R^1$ to form a 5-membered heterocycloalkyl ring which is optionally substituted with 1 to 6 fluorine atoms. $R^3$ can be joined to $R^2$ to form a 5-membered cycloalkyl ring which is optionally substituted with 1 to 6 fluorine atoms. $R^3$ can be joined to $R^2$ to form a 4-membered cycloalkyl ring which is optionally substituted with 1 to 6 fluorine atoms. $R^3$ can be joined to $R^4$ to form a 5-membered cycloalkyl ring which is optionally substituted with 1 to 6 fluorine atoms.

In the compounds herein, $R^4$ can be H or $C_{1-3}$ alkyl optionally substituted with 1 to 6 fluorine atoms, or can be joined to $R^3$ to form a ring which is optionally substituted with 1-6 fluorine atoms or can be joined to $R^5$ to form a ring which is optionally substituted with 1 to 6 fluorine atoms. $R^4$ can be selected from H, methyl, ethyl or isopropyl. $R^4$ can be H. $R^4$ can be $C_{1-3}$ alkyl. $R^4$ can be methyl. $R^4$ can be ethyl. $R^4$ can be isopropyl. $R^4$ can be joined to $R^3$ to form a 3 to 6-membered ring which is optionally substituted with 1 to 6 fluorine atoms. $R^4$ can be joined to $R^5$ to form a 3 to 6-membered ring which is optionally substituted with 1 to 6 fluorine atoms. $R^4$ can be joined to $R^3$ to form a 5-membered ring which is optionally substituted with 1 to 6 fluorine atoms. $R^4$ can be joined to $R^5$ to form a 5-membered ring which is optionally substituted with 1 to 6 fluorine atoms. $R^4$ can be joined to $R^3$ to form a cycloalkyl ring which is optionally substituted with 1 to 6 fluorine atoms. $R^4$ can be joined to $R^5$ to form a cycloalkyl ring which is optionally substituted with 1 to 6 fluorine atoms. $R^4$ can be joined to $R^3$ to form a 3 to 6-membered cycloalkyl ring which is optionally substituted with 1 to 6 fluorine atoms. $R^4$ can be joined to $R^5$ to form a 3 to 6-membered cycloalkyl ring which is optionally substituted with 1 to 6 fluorine atoms. $R^4$ can be joined to $R^3$ to form a 5-membered cycloalkyl ring which is optionally substituted with 1 to 6 fluorine atoms. $R^4$ can be joined to $R^5$ to form a 5-membered cycloalkyl ring which is optionally substituted with 1 to 6 fluorine atoms.

In the compounds herein, $R^5$ can be H or $C_{1-3}$ alkyl optionally substituted with 1 to 6 fluorine atoms, or can be joined to $R^4$ to form a ring which is optionally substituted with 1 to 6 fluorine atoms. $R^5$ can be H. $R^5$ can be $C_{1-3}$ alkyl optionally substituted with 1 to 6 fluorine atoms. $R^5$ can be $C_{1-3}$ alkyl. $R^5$ can be joined to $R^4$ to form a ring which is optionally substituted with 1 to 6 fluorine atoms. $R^5$ can be methyl. $R^5$ can be joined to $R^4$ to form a 3 to 6-membered ring which is optionally substituted with 1 to 6 fluorine atoms. $R^5$ can be joined to $R^4$ to form a 5-membered ring which is optionally substituted with 1 to 6 fluorine atoms. $R^5$ can be joined to $R^4$ to form a cycloalkyl ring which is optionally substituted with 1 to 6 fluorine atoms. $R^5$ can be joined to $R^4$ to form a 5-membered cycloalkyl ring which is optionally substituted with 1 to 6 fluorine atoms.

In the compounds herein, n can be 0. n can be 1.

Compounds of the invention include compounds according to formula (4):

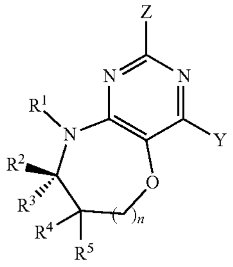

or a salt thereof, wherein Y, Z, $R^1$, $R^2$, $R^3$, $R^4$, $R^5$ and n are as defined above.

The moiety comprising groups $R^1$, $R^2$, $R^3$, $R^4$ and $R^5$ can be selected from the group consisting of:

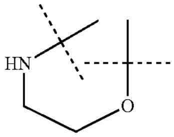
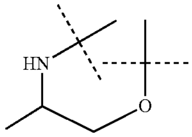
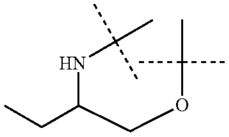
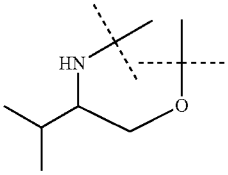
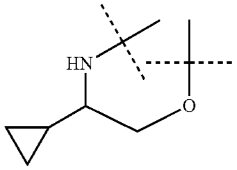
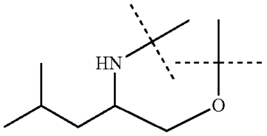
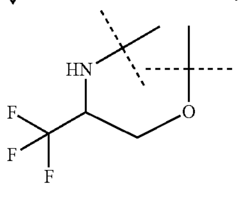
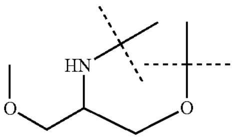

-continued

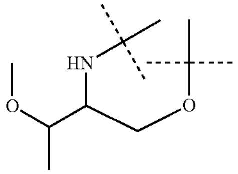
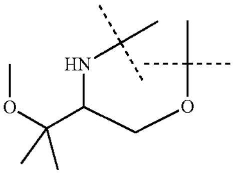
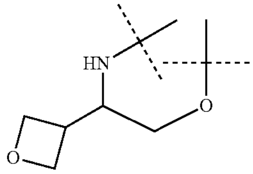
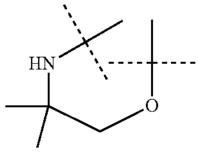
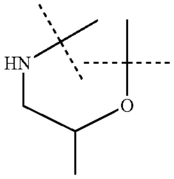
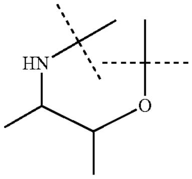
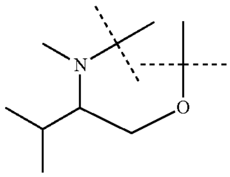
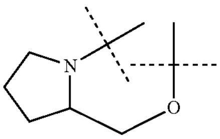
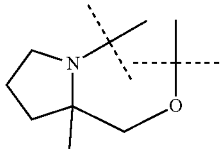
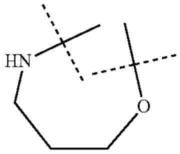
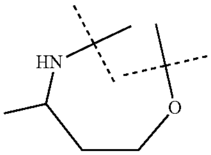
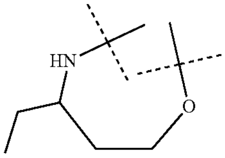
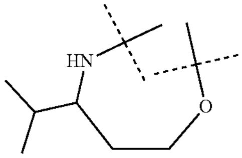
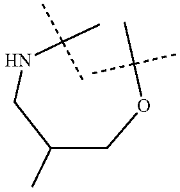
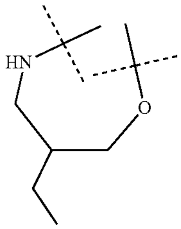
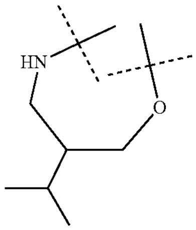
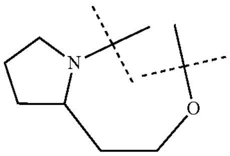
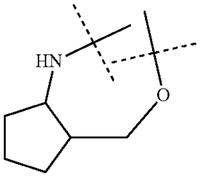

-continued
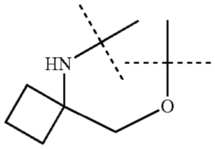
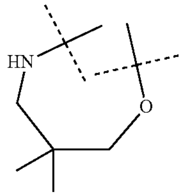
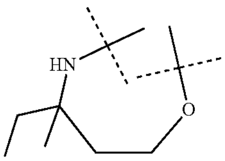
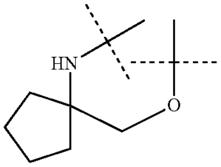
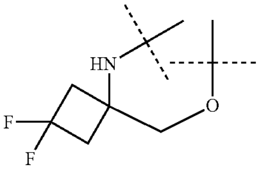
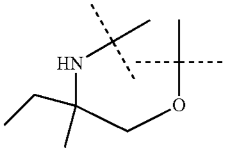
The compound can be selected from the group consisting of:
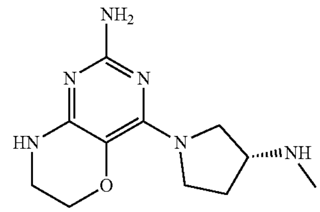 [SMILES: CN[C@@H]1CCN(c2nc(N)nc3c2OCCN3)C1]
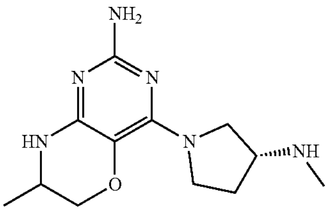
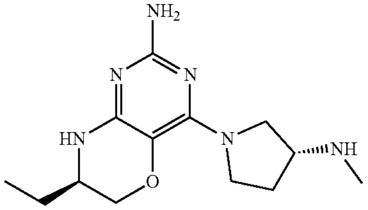 [SMILES: CC[C@@H]1COc2c(nc(N)nc2N2CC[C@@H](NC)C2)N1]
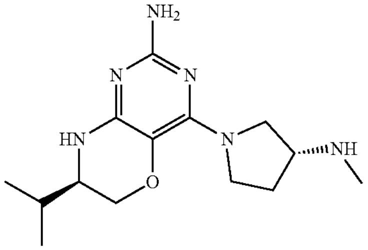
-continued
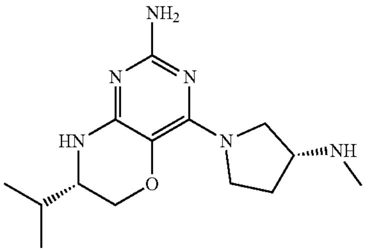
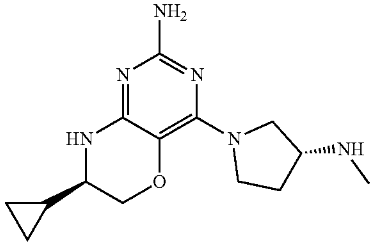
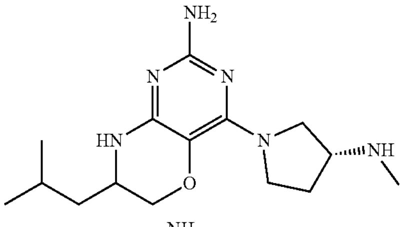
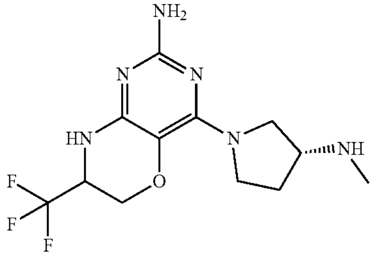
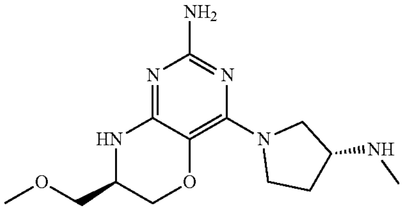
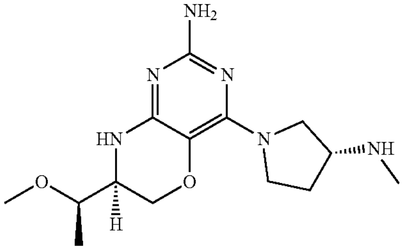
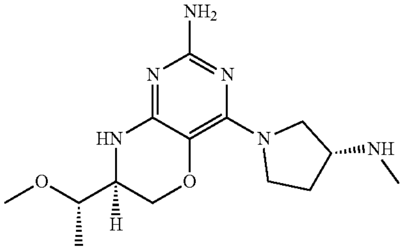

-continued
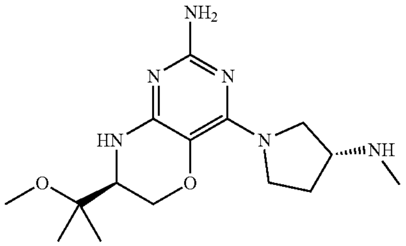
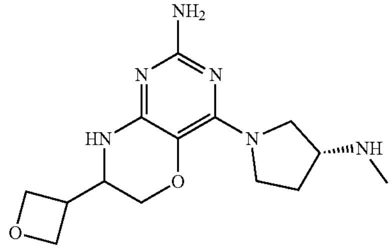
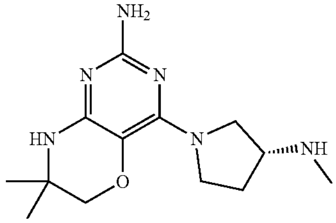
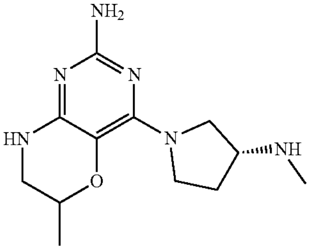
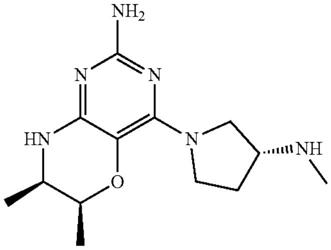
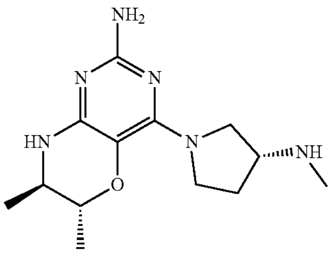
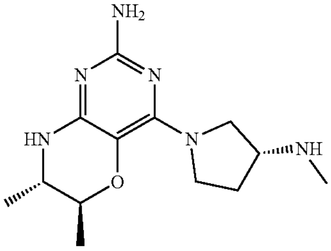
-continued
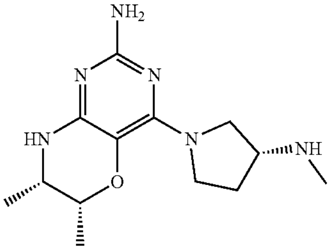
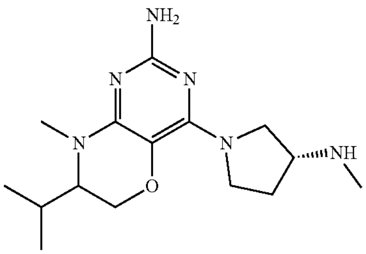
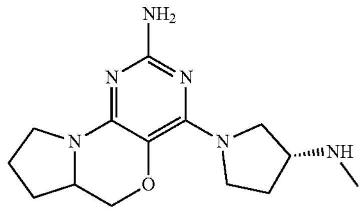
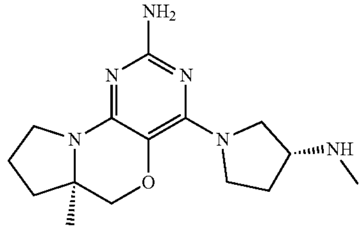
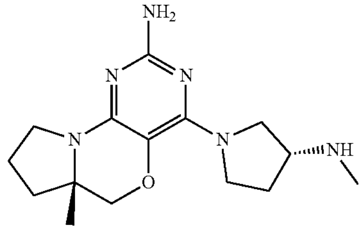
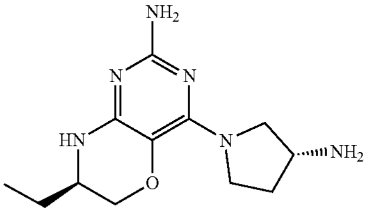
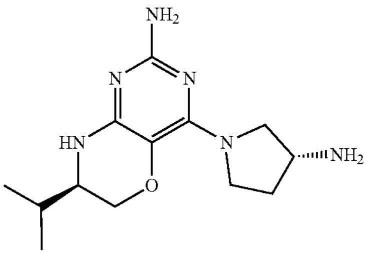

-continued
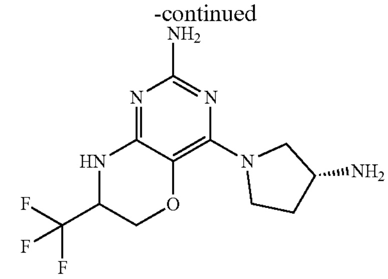
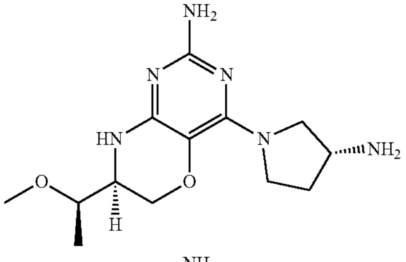
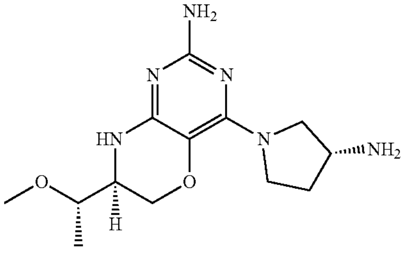
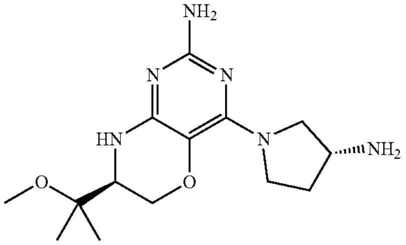
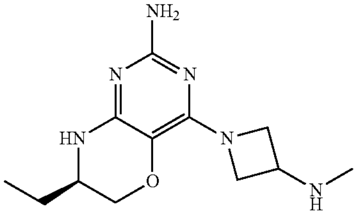
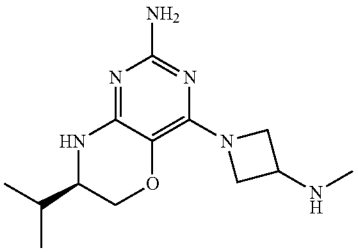
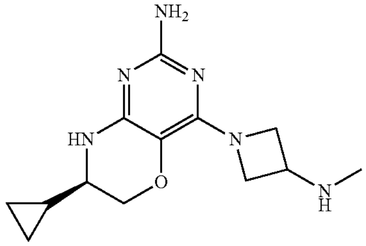
-continued
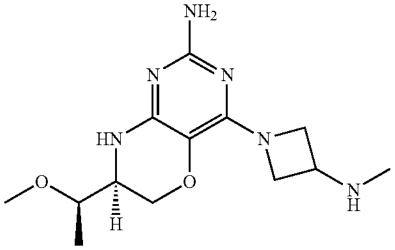
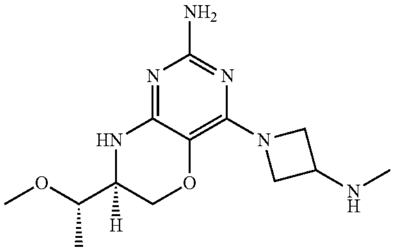
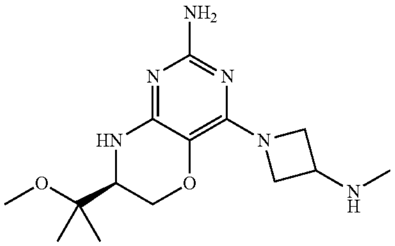
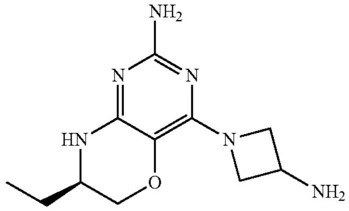
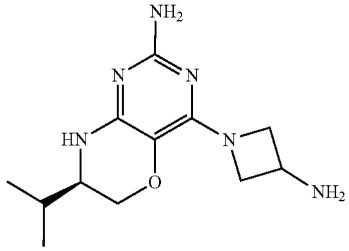
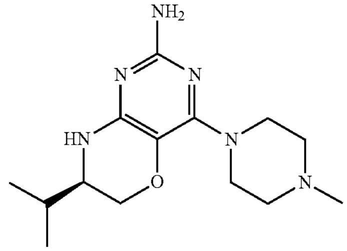
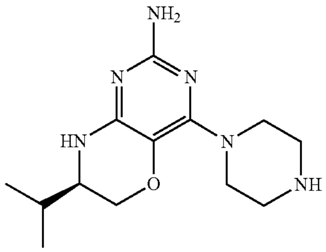

-continued
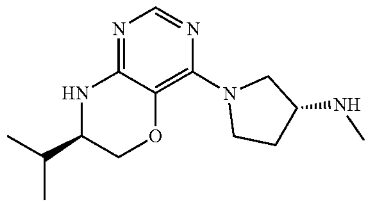
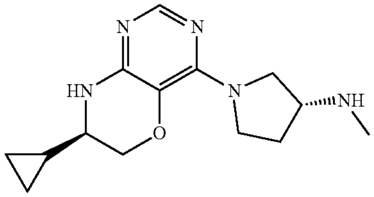
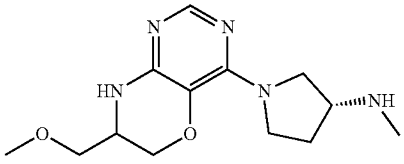
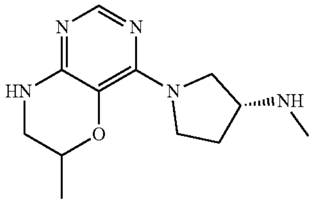
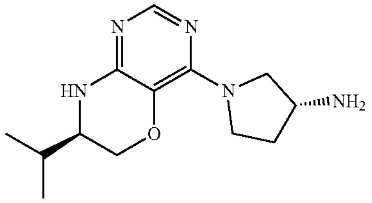
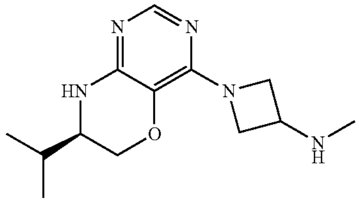
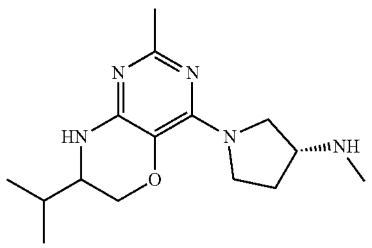
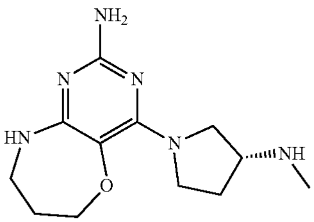
-continued
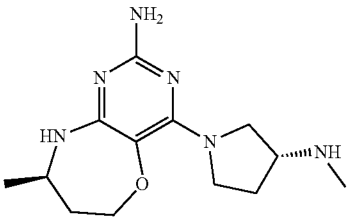
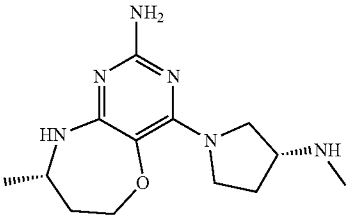
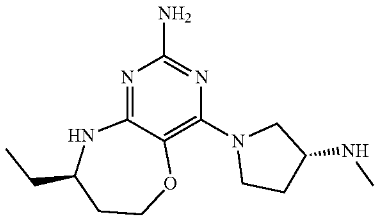
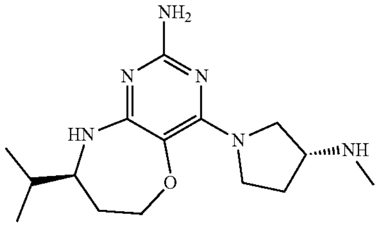
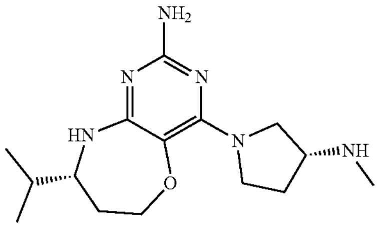
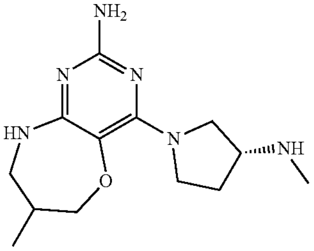
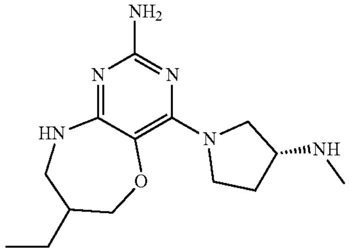

-continued

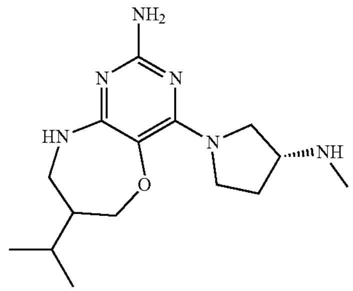

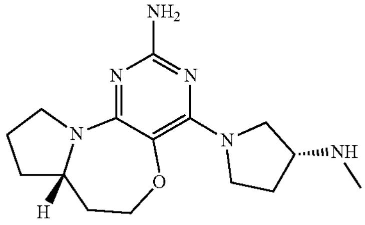

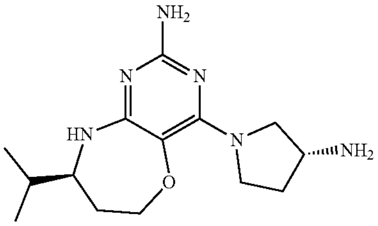

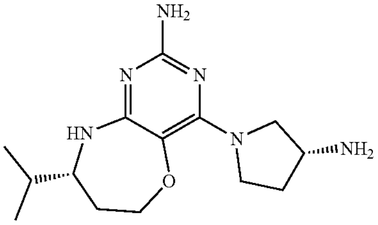

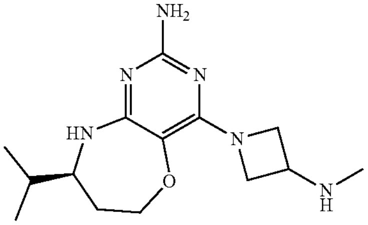

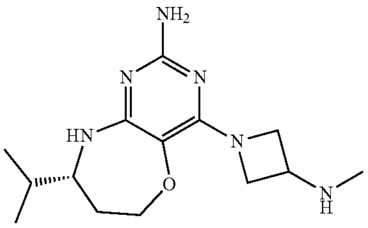

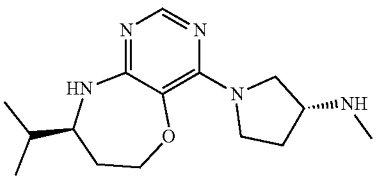

-continued

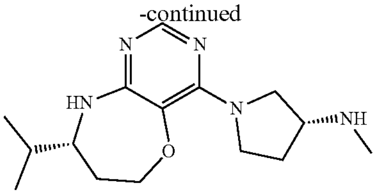

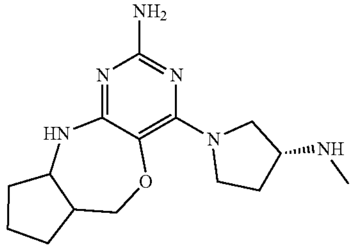

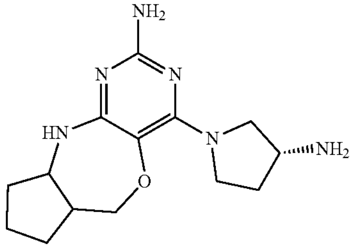

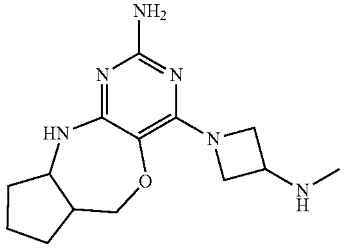

or a salt thereof.

The compound can be selected from the group consisting of:

(R)-4-(3-(Methylamino)pyrrolidin-1-yl)-7,8-dihydro-6H-pyrimido[5,4-b][1,4]oxazin-2-amine;

7-Methyl-4-((R)-3-(methylamino)pyrrolidin-1-yl)-7,8-dihydro-6H-pyrimido[5,4-b][1,4]oxazin-2-amine;

(R)-7-Ethyl-4-((R)-3-(methylamino)pyrrolidin-1-yl)-7,8-dihydro-6H-pyrimido[5,4-b][1,4]oxazin-2-amine;

(R)-7-Isopropyl-4-((R)-3-(methylamino)pyrrolidin-1-yl)-7,8-dihydro-6H-pyrimido[5,4-b][1,4]oxazin-2-amine;

(S)-7-Isopropyl-4-((R)-3-(methylamino)pyrrolidin-1-yl)-7,8-dihydro-6H-pyrimido[5,4-b][1,4]oxazin-2-amine;

(R)-7-Cyclopropyl-4-((R)-3-(methylamino)pyrrolidin-1-yl)-7,8-dihydro-6H-pyrimido[5,4-b][1,4]oxazin-2-amine;

7-isobutyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-7-(trifluoromethyl)-7,8-dihydro-6H-pyrimido[5,4-b][1,4]oxazin-2-amine;

(R)-7-(Methoxymethyl)-4-((R)-3-(methylamino)pyrrolidin-1-yl)-7,8-dihydro-6H-pyrimido[5,4-b][1,4]oxazin-2-amine;

(S)-7-((R)-1-Methoxyethyl)-4-((R)-3-(methylamino)pyrrolidin-1-yl)-7,8-dihydro-6H-pyrimido[5,4-b][1,4]oxazin-2-amine;

(S)-7-((S)-1-Methoxyethyl)-4-((R)-3-(methylamino)pyrrolidin-1-yl)-7,8-dihydro-6H-pyrimido[5,4-b][1,4]oxazin-2-amine;

(S)-7-(2-Methoxypropan-2-yl)-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-7-(oxetan-3-yl)-7,8-dihydro-6H-pyrimido[5,4-b][1,4]oxazin-2-amine;

(R)-7,7-Dimethyl-4-(3-(methylamino)pyrrolidin-1-yl)-7,8-dihydro-6H-pyrimido[5,4-b][1,4]oxazin-2-amine;

6-Methyl-4-((R)-3-(methylamino)pyrrolidin-1-yl)-7,8-dihydro-6H-pyrimido[5,4-b][1,4]oxazin-2-amine;

(6S,7R)-6,7-Dimethyl-4-((R)-3-(methylamino)pyrrolidin-1-yl)-7,8-dihydro-6H-pyrimido[5,4-b][1,4]oxazin-2-amine;

(6R,7R)-6,7-Dimethyl-4-((R)-3-(methylamino)pyrrolidin-1-yl)-7,8-dihydro-6H-pyrimido[5,4-b][1,4]oxazin-2-amine;

(6S,7S)-6,7-Dimethyl-4-((R)-3-(methylamino)pyrrolidin-1-yl)-7,8-dihydro-6H-pyrimido[5,4-b][1,4]oxazin-2-amine;

(6R,7S)-6,7-Dimethyl-4-((R)-3-(methylamino)pyrrolidin-1-yl)-7,8-dihydro-6H-pyrimido[5,4-b][1,4]oxazin-2-amine;

7-Isopropyl-8-methyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-6a,7,8,9-tetrahydro-6H-pyrimido[5,4-b]pyrrolo[1,2-d][1,4]oxazin-2-amine;

(R)-6a-Methyl-4-((R)-3-(methylamino)pyrrolidin-1-yl)-6a,7,8,9-tetrahydro-6H-pyrimido[5,4-b]pyrrolo[1,2-d][1,4]oxazin-2-amine;

(S)-6a-Methyl-4-((R)-3-(methylamino)pyrrolidin-1-yl)-6a,7,8,9-tetrahydro-6H-pyrimido[5,4-b]pyrrolo[1,2-d][1,4]oxazin-2-amine;

(R)-4-((R)-3-Aminopyrrolidin-1-yl)-7-ethyl-7,8-dihydro-6H-pyrimido[5,4-b][1,4]oxazin-2-amine;

(R)-4-((R)-3-Aminopyrrolidin-1-yl)-7-isopropyl-7,8-dihydro-6H-pyrimido[5,4-b][1,4]oxazin-2-amine;

4-((R)-3-Aminopyrrolidin-1-yl)-7-(trifluoromethyl)-7,8-dihydro-6H-pyrimido[5,4-b][1,4]oxazin-2-amine;

(S)-4-((R)-3-Aminopyrrolidin-1-yl)-7-((R)-1-methoxyethyl)-7,8-dihydro-6H-pyrimido[5,4-b][1,4]oxazin-2-amine;

(S)-4-((R)-3-Aminopyrrolidin-1-yl)-7-((S)-1-methoxyethyl)-7,8-dihydro-6H-pyrimido[5,4-b][1,4]oxazin-2-amine;

(S)-4-((R)-3-Aminopyrrolidin-1-yl)-7-(2-methoxypropan-2-yl)-7,8-dihydro-6H-pyrimido[5,4-b][1,4]oxazin-2-amine;

(R)-7-Ethyl-4-(3-(methylamino)azetidin-1-yl)-7,8-dihydro-6H-pyrimido[5,4-b][1,4]oxazin-2-amine;

(R)-7-Isopropyl-4-(3-(methylamino)azetidin-1-yl)-7,8-dihydro-6H-pyrimido[5,4-b][1,4]oxazin-2-amine;

(R)-7-Cyclopropyl-4-(3-(methylamino)azetidin-1-yl)-7,8-dihydro-6H-pyrimido[5,4-b][1,4]oxazin-2-amine;

(S)-7-((R)-1-Methoxyethyl)-4-(3-(methylamino)azetidin-1-yl)-7,8-dihydro-6H-pyrimido[5,4-b][1,4]oxazin-2-amine;

(S)-7-((S)-1-Methoxyethyl)-4-(3-(methylamino)azetidin-1-yl)-7,8-dihydro-6H-pyrimido[5,4-b][1,4]oxazin-2-amine;

(S)-7-(2-Methoxypropan-2-yl)-4-(3-(methylamino)azetidin-1-yl)-7,8-dihydro-6H-pyrimido[5,4-b][1,4]oxazin-2-amine;

(R)-4-(3-Aminoazetidin-1-yl)-7-ethyl-7,8-dihydro-6H-pyrimido[5,4-b][1,4]oxazin-2-amine;

(R)-4-(3-Aminoazetidin-1-yl)-7-isopropyl-7,8-dihydro-6H-pyrimido[5,4-b][1,4]oxazin-2-amine (R)-7-Isopropyl-4-(4-methylpiperazin-1-yl)-7,8-dihydro-6H-pyrimido[5,4-b][1,4]oxazin-2-amine;

(R)-7-Isopropyl-4-(piperazin-1-yl)-7,8-dihydro-6H-pyrimido[5,4-b][1,4]oxazin-2-amine;

(R)-1-((R)-7-Isopropyl-7,8-dihydro-6H-pyrimido[5,4-b][1,4]oxazin-4-yl)-N-methylpyrrolidin-3-amine;

(R)-1-((R)-7-Cyclopropyl-7,8-dihydro-6H-pyrimido[5,4-b][1,4]oxazin-4-yl)-N-methylpyrrolidin-3-amine;

(3R)-1-(7-(Methoxymethyl)-7,8-dihydro-6H-pyrimido[5,4-b][1,4]oxazin-4-yl)-N-methylpyrrolidin-3-amine;

(R)-1-((S)-7-((R)-1-Methoxyethyl)-7,8-dihydro-6H-pyrimido[5,4-b][1,4]oxazin-4-yl)-N-methylpyrrolidin-3-amine;

(3R)-N-Methyl-1-(6-methyl-7,8-dihydro-6H-pyrimido[5,4-b][1,4]oxazin-4-yl)pyrrolidin-3-amine;

(R)-1-((R)-7-Isopropyl-7,8-dihydro-6H-pyrimido[5,4-b][1,4]oxazin-4-yl)pyrrolidin-3-amine;

(R)-1-((S)-7-((R)-1-Methoxyethyl)-7,8-dihydro-6H-pyrimido[5,4-b][1,4]oxazin-4-yl)pyrrolidin-3-amine;

(R)-1-(7-Isopropyl-7,8-dihydro-6H-pyrimido[5,4-b][1,4]oxazin-4-yl)-N-methylazetidin-3-amine;

(3R)-1-(7-Isopropyl-2-methyl-7,8-dihydro-6H-pyrimido[5,4-b][1,4]oxazin-4-yl)-N-methylpyrrolidin-3-amine;

(R)-4-(3-(Methylamino)pyrrolidin-1-yl)-6,7,8,9-tetrahydropyrimido[5,4-b][1,4]oxazepin-2-amine;

(R)-8-Methyl-4-((R)-3-(methylamino)pyrrolidin-1-yl)-6,7,8,9-tetrahydropyrimido[5,4-b][1,4]oxazepin-2-amine;

(S)-8-Methyl-4-((R)-3-(methylamino)pyrrolidin-1-yl)-6,7,8,9-tetrahydropyrimido[5,4-b][1,4]oxazepin-2-amine;

(R)-8-Ethyl-4-((R)-3-(methylamino)pyrrolidin-1-yl)-6,7,8,9-tetrahydropyrimido[5,4-b][1,4]oxazepin-2-amine;

(S)-8-Isopropyl-4-((R)-3-(methylamino)pyrrolidin-1-yl)-6,7,8,9-tetrahydropyrimido[5,4-b][1,4]oxazepin-2-amine;

(R)-8-Isopropyl-4-((R)-3-(methylamino)pyrrolidin-1-yl)-6,7,8,9-tetrahydropyrimido[5,4-b][1,4]oxazepin-2-amine;

7-Methyl-4-((R)-3-(methylamino)pyrrolidin-1-yl)-6,7,8,9-tetrahydropyrimido[5,4-b][1,4]oxazepin-2-amine;

7-Ethyl-4-((R)-3-(methylamino)pyrrolidin-1-yl)-6,7,8,9-tetrahydropyrimido[5,4-b][1,4]oxazepin-2-amine;

7-Isopropyl-4-((R)-3-(methylamino)pyrrolidin-1-yl)-6,7,8,9-tetrahydropyrimido[5,4-b][1,4]oxazepin-2-amine;

(S)-4-((R)-3-(Methylamino)pyrrolidin-1-yl)-6,7,7a,8,9,10-hexahydropyrimido[5,4-b]pyrrolo[1,2-d][1,4]oxazepin-2-amine;

(S)-4-((R)-3-Aminopyrrolidin-1-yl)-8-isopropyl-6,7,8,9-tetrahydropyrimido[5,4-b][1,4]oxazepin-2-amine;

(R)-4-((R)-3-Aminopyrrolidin-1-yl)-8-isopropyl-6,7,8,9-tetrahydropyrimido[5,4-b][1,4]oxazepin-2-amine;

(S)-8-Isopropyl-4-(3-(methylamino)azetidin-1-yl)-6,7,8,9-tetrahydropyrimido[5,4-b][1,4]oxazepin-2-amine;

(R)-8-Isopropyl-4-(3-(methylamino)azetidin-1-yl)-6,7,8,9-tetrahydropyrimido[5,4-b][1,4]oxazepin-2-amine;

(R)-1-((S)-8-Isopropyl-6,7,8,9-tetrahydropyrimido[5,4-b][1,4]oxazepin-4-yl)-N-methylpyrrolidin-3-amine;

(R)-1-((R)-8-Isopropyl-6,7,8,9-tetrahydropyrimido[5,4-b][1,4]oxazepin-4-yl)-N-methylpyrrolidin-3-amine;

4-[(3R)-3-(methylamino)pyrrolidin-1-yl]-6a,7,8,9,9a,10-hexahydro-6H-cyclopenta[e]pyrimido[5,4-b][1,4]oxazepin-2-amine;

4-[(3R)-3-aminopyrrolidin-1-yl]-6a,7,8,9,9a,10-hexahydro-6H-cyclopenta[e]pyrimido[5,4-b][1,4]oxazepin-2-amine;

4-[3-(methylamino)azetidin-1-yl]-6a,7,8,9,9a,10-hexahydro-6H-cyclopenta[e]pyrimido[5,4-b][1,4]oxazepin-2-amine;

4'-[(3R)-3-(methylamino)pyrrolidin-1-yl]-6'H,8'H-spiro[cyclobutane-1,7'-pyrimido[5,4-b][1,4]oxazin]-2'-amine;

7,7-dimethyl-4-[(3R)-3-(methylamino)pyrrolidin-1-yl]-6,7,8,9-tetrahydropyrimido[5,4-b][1,4]oxazepin-2-amine;

8-ethyl-4-[3-(methylamino)azetidin-1-yl]-6,7,8,9-tetrahydropyrimido[5,4-b][1,4]oxazepin-2-amine;

4-[(3R)-3-aminopyrrolidin-1-yl]-8-ethyl-6,7,8,9-tetrahydropyrimido[5,4-b][1,4]oxazepin-2-amine;

8-ethyl-4-[(4aR,7aR)-octahydro-6H-pyrrolo[3,4-b]pyridin-6-yl]-6,7,8,9-tetrahydropyrimido[5,4-b][1,4]oxazepin-2-amine;
(3R)-1-(8-ethyl-8-methyl-6,7,8,9-tetrahydropyrimido[5,4-b][1,4]oxazepin-4-yl)-N-methylpyrrolidin-3-amine;
8-ethyl-8-methyl-4-[(3R)-3-(methylamino)pyrrolidin-1-yl]-6,7,8,9-tetrahydropyrimido[5,4-b][1,4]oxazepin-2-amine;
4'-[(3R)-3-(methylamino)pyrrolidin-1-yl]-6'H,8'H-spiro[cyclopentane-1,7'-pyrimido[5,4-b][1,4]oxazin]-2'-amine;
(3R)-N-methyl-1-(6'H,8'H-spiro[cyclopentane-1,7'-pyrimido[5,4-b][1,4]oxazin]-4'-yl)pyrrolidin-3-amine;
(3R)-1-(3,3-difluoro-6'H,8'H-spiro[cyclobutane-1,7'-pyrimido[5,4-b][1,4]oxazin]-4'-yl)-N-methylpyrrolidin-3-amine;
7-ethyl-7-methyl-4-[(3R)-3-(methylamino)pyrrolidin-1-yl]-7,8-dihydro-6H-pyrimido[5,4-b][1,4]oxazin-2-amine;
3,3-difluoro-4'-[(3R)-3-(methylamino)pyrrolidin-1-yl]-6'H,8'H-spiro[cyclobutane-1,7'-pyrimido[5,4-b][1,4]oxazin]-2'-amine;
or a salt thereof.

The compound can be a salt of any compound described above. The compound can be a dihydrochloride salt. The compound can be a hydrochloride salt. The compound can be a ditrifluoroacetic acid salt. The compound can be a trifluoroacetic acid salt.

The compound can be selected from the group consisting of:
(R)-7-Ethyl-4-((R)-3-(methylamino)pyrrolidin-1-yl)-7,8-dihydro-6H-pyrimido[5,4-b][1,4]oxazin-2-amine dihydrochloride salt;
(R)-7-Cyclopropyl-4-((R)-3-(methylamino)pyrrolidin-1-yl)-7,8-dihydro-6H-pyrimido[5,4-b][1,4]oxazin-2-amine ditrifluoroacetic acid salt;
(S)-7-((R)-1-Methoxyethyl)-4-((R)-3-(methylamino)pyrrolidin-1-yl)-7,8-dihydro-6H-pyrimido[5,4-b][1,4]oxazin-2-amine dihydrochloride salt;
(S)-7-((S)-1-Methoxyethyl)-4-((R)-3-(methylamino)pyrrolidin-1-yl)-7,8-dihydro-6H-pyrimido[5,4-b][1,4]oxazin-2-amine dihydrochloride salt;
(R)-7,7-Dimethyl-4-(3-(methylamino)pyrrolidin-1-yl)-7,8-dihydro-6H-pyrimido[5,4-b][1,4]oxazin-2-amine dihydrochloride salt;
(6S,7R)-6,7-Dimethyl-4-((R)-3-(methylamino)pyrrolidin-1-yl)-7,8-dihydro-6H-pyrimido[5,4-b][1,4]oxazin-2-amine dihydrochloride salt;
(6R,7R)-6,7-Dimethyl-4-((R)-3-(methylamino)pyrrolidin-1-yl)-7,8-dihydro-6H-pyrimido[5,4-b][1,4]oxazin-2-amine dihydrochloride salt;
(6S,7S)-6,7-Dimethyl-4-((R)-3-(methylamino)pyrrolidin-1-yl)-7,8-dihydro-6H-pyrimido[5,4-b][1,4]oxazin-2-amine dihydrochloride salt;
(6R,7S)-6,7-Dimethyl-4-((R)-3-(methylamino)pyrrolidin-1-yl)-7,8-dihydro-6H-pyrimido[5,4-b][1,4]oxazin-2-amine dihydrochloride salt;
(R)-4-((R)-3-Aminopyrrolidin-1-yl)-7-ethyl-7,8-dihydro-6H-pyrimido[5,4-b][1,4]oxazin-2-amine dihydrochloride salt;
(R)-4-((R)-3-Aminopyrrolidin-1-yl)-7-isopropyl-7,8-dihydro-6H-pyrimido[5,4-b][1,4]oxazin-2-amine dihydrochloride salt;
(S)-4-((R)-3-Aminopyrrolidin-1-yl)-7-((R)-1-methoxyethyl)-7,8-dihydro-6H-pyrimido[5,4-b][1,4]oxazin-2-amine dihydrochloride salt;
(S)-4-((R)-3-Aminopyrrolidin-1-yl)-7-((S)-1-methoxyethyl)-7,8-dihydro-6H-pyrimido[5,4-b][1,4]oxazin-2-amine dihydrochloride salt;
(R)-7-Ethyl-4-(3-(methylamino)azetidin-1-yl)-7,8-dihydro-6H-pyrimido[5,4-b][1,4]oxazin-2-amine ditrifluoroacetic acid salt;
(R)-7-Cyclopropyl-4-(3-(methylamino)azetidin-1-yl)-7,8-dihydro-6H-pyrimido[5,4-b][1,4]oxazin-2-amine ditrifluoroacetic acid salt;
(S)-7-((R)-1-Methoxyethyl)-4-(3-(methylamino)azetidin-1-yl)-7,8-dihydro-6H-pyrimido[5,4-b][1,4]oxazin-2-amine dihydrochloride salt;
(R)-4-(3-Aminoazetidin-1-yl)-7-ethyl-7,8-dihydro-6H-pyrimido[5,4-b][1,4]oxazin-2-amine ditrifluoroacetic acid salt;
(R)-1-((S)-7-((R)-1-Methoxyethyl)-7,8-dihydro-6H-pyrimido[5,4-b][1,4]oxazin-4-yl)-N-methylpyrrolidin-3-amine hydrochloride salt;
(R)-1-((S)-7-((R)-1-Methoxyethyl)-7,8-dihydro-6H-pyrimido[5,4-b][1,4]oxazin-4-yl)pyrrolidin-3-amine hydrochloride salt;
(R)-8-Methyl-4-((R)-3-(methylamino)pyrrolidin-1-yl)-6,7,8,9-tetrahydropyrimido[5,4-b][1,4]oxazepin-2-amine ditrifluoroacetic acid salt;
(S)-8-Methyl-4-((R)-3-(methylamino)pyrrolidin-1-yl)-6,7,8,9-tetrahydropyrimido[5,4-b][1,4]oxazepin-2-amine ditrifluoroacetic acid salt;
(R)-8-Ethyl-4-((R)-3-(methylamino)pyrrolidin-1-yl)-6,7,8,9-tetrahydropyrimido[5,4-b][1,4]oxazepin-2-amine ditrifluoroacetic acid salt;
(S)-8-Isopropyl-4-((R)-3-(methylamino)pyrrolidin-1-yl)-6,7,8,9-tetrahydropyrimido[5,4-b][1,4]oxazepin-2-amine ditrifluoroacetic acid salt;
(R)-8-Isopropyl-4-((R)-3-(methylamino)pyrrolidin-1-yl)-6,7,8,9-tetrahydropyrimido[5,4-b][1,4]oxazepin-2-amine ditrifluoroacetic acid salt;
7-Methyl-4-((R)-3-(methylamino)pyrrolidin-1-yl)-6,7,8,9-tetrahydropyrimido[5,4-b][1,4]oxazepin-2-amine ditrifluoroacetic acid salt;
7-Ethyl-4-((R)-3-(methylamino)pyrrolidin-1-yl)-6,7,8,9-tetrahydropyrimido[5,4-b][1,4]oxazepin-2-amine ditrifluoroacetic acid salt;
7-Isopropyl-4-((R)-3-(methylamino)pyrrolidin-1-yl)-6,7,8,9-tetrahydropyrimido[5,4-b][1,4]oxazepin-2-amine ditrifluoroacetic acid salt;
(S)-4-((R)-3-Aminopyrrolidin-1-yl)-8-isopropyl-6,7,8,9-tetrahydropyrimido[5,4-b][1,4]oxazepin-2-amine ditrifluoroacetic acid salt;
(R)-4-((R)-3-Aminopyrrolidin-1-yl)-8-isopropyl-6,7,8,9-tetrahydropyrimido[5,4-b][1,4]oxazepin-2-amine ditrifluoroacetic acid salt;
(S)-8-Isopropyl-4-(3-(methylamino)azetidin-1-yl)-6,7,8,9-tetrahydropyrimido[5,4-b][1,4]oxazepin-2-amine ditrifluoroacetic acid salt;
(R)-8-Isopropyl-4-(3-(methylamino)azetidin-1-yl)-6,7,8,9-tetrahydropyrimido[5,4-b][1,4]oxazepin-2-amine ditrifluoroacetic acid salt;
(R)-1-((S)-8-Isopropyl-6,7,8,9-tetrahydropyrimido[5,4-b][1,4]oxazepin-4-yl)-N-methylpyrrolidin-3-amine trifluoroacetic acid salt; and
(R)-1-((R)-8-Isopropyl-6,7,8,9-tetrahydropyrimido[5,4-b][1,4]oxazepin-4-yl)-N-methylpyrrolidin-3-amine trifluoroacetic acid salt.

Specific examples of compounds include those having low hERG activity.

Specific examples of compounds having low hERG activity may include compounds selected from the group consisting of:
(R)-4-(3-(Methylamino)pyrrolidin-1-yl)-7,8-dihydro-6H-pyrimido[5,4-b][1,4]oxazin-2-amine;

(R)-7-Ethyl-4-((R)-3-(methylamino)pyrrolidin-1-yl)-7,8-dihydro-6H-pyrimido[5,4-b][1,4]oxazin-2-amine;
(R)-7-Isopropyl-4-((R)-3-(methylamino)pyrrolidin-1-yl)-7,8-dihydro-6H-pyrimido[5,4-b][1,4]oxazin-2-amine;
4-((R)-3-(Methylamino)pyrrolidin-1-yl)-7-(trifluoromethyl)-7,8-dihydro-6H-pyrimido[5,4-b][1,4]oxazin-2-amine;
(R)-7-(Methoxymethyl)-4-((R)-3-(methylamino)pyrrolidin-1-yl)-7,8-dihydro-6H-pyrimido[5,4-b][1,4]oxazin-2-amine;
(S)-7-((R)-1-Methoxyethyl)-4-((R)-3-(methylamino)pyrrolidin-1-yl)-7,8-dihydro-6H-pyrimido[5,4-b][1,4]oxazin-2-amine;
(S)-7-(2-Methoxypropan-2-yl)-4-((R)-3-(methylamino)pyrrolidin-1-yl)-7,8-dihydro-6H-pyrimido[5,4-b][1,4]oxazin-2-amine;
(R)-7,7-Dimethyl-4-(3-(methylamino)pyrrolidin-1-yl)-7,8-dihydro-6H-pyrimido[5,4-b][1,4]oxazin-2-amine;
6-Methyl-4-((R)-3-(methylamino)pyrrolidin-1-yl)-7,8-dihydro-6H-pyrimido[5,4-b][1,4]oxazin-2-amine;
4-((R)-3-(Methylamino)pyrrolidin-1-yl)-6a,7,8,9-tetrahydro-6H-pyrimido[5,4-b]pyrrolo[1,2-d][1,4]oxazin-2-amine;
(R)-4-((R)-3-Aminopyrrolidin-1-yl)-7-isopropyl-7,8-dihydro-6H-pyrimido[5,4-b][1,4]oxazin-2-amine;
4-((R)-3-Aminopyrrolidin-1-yl)-7-(trifluoromethyl)-7,8-dihydro-6H-pyrimido[5,4-b][1,4]oxazin-2-amine;
(R)-7-Isopropyl-4-(3-(methylamino)azetidin-1-yl)-7,8-dihydro-6H-pyrimido[5,4-b][1,4]oxazin-2-amine;
(S)-7-((R)-1-Methoxyethyl)-4-(3-(methylamino)azetidin-1-yl)-7,8-dihydro-6H-pyrimido[5,4-b][1,4]oxazin-2-amine;
(R)-7-Isopropyl-4-(piperazin-1-yl)-7,8-dihydro-6H-pyrimido[5,4-b][1,4]oxazin-2-amine;
(R)-1-((R)-7-Isopropyl-7,8-dihydro-6H-pyrimido[5,4-b][1,4]oxazin-4-yl)pyrrolidin-3-amine;
(R)-8-Methyl-4-((R)-3-(methylamino)pyrrolidin-1-yl)-6,7,8,9-tetrahydropyrimido[5,4-b][1,4]oxazepin-2-amine;
(S)-8-Isopropyl-4-((R)-3-(methylamino)pyrrolidin-1-yl)-6,7,8,9-tetrahydropyrimido[5,4-b][1,4]oxazepin-2-amine;
(S)-4-((R)-3-Aminopyrrolidin-1-yl)-8-isopropyl-6,7,8,9-tetrahydropyrimido[5,4-b][1,4]oxazepin-2-amine;
(S)-8-Isopropyl-4-(3-(methylamino)azetidin-1-yl)-6,7,8,9-tetrahydropyrimido[5,4-b][1,4]oxazepin-2-amine;
or a salt thereof.

Definitions

In this application, the following definitions apply, unless indicated otherwise.

The term "treatment", in relation to the uses of any of the compounds described herein, including those of the formula (1), formula (1a), formula (1b), formula (2a), formula (2b), formula (2c), formula (2d), formula (2e), formula (3a), formula (3b), formula (3c) and formula (4), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "alkyl" as in "$C_{1-3}$ alkyl", "cycloalkyl" as in "$C_{3-6}$ cycloalkyl", "heterocycloalkyl" and "heterocyclyl" as in "3 to 6-membered heterocyclyl group" are all used in their conventional sense (e.g. as defined in the IUPAC Gold Book), unless indicated otherwise.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g.(+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Methods for the Preparation of Compounds of the Formula (1)

Compounds of the formula (1) can be prepared in accordance with synthetic methods well known to the skilled person and as described herein. Accordingly, in one embodiment, the invention provides a process for the preparation of a compound as defined in formula (1) above, which process comprises:

(A) When it is required to prepare a compound of formula (1) wherein Z is $NH_2$. The sequence of reactions as illustrated in Scheme 1 below:

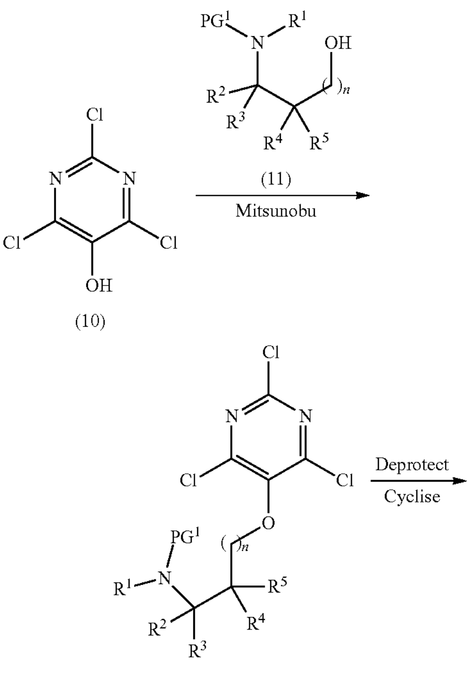

(11)
(10)
(12)

-continued

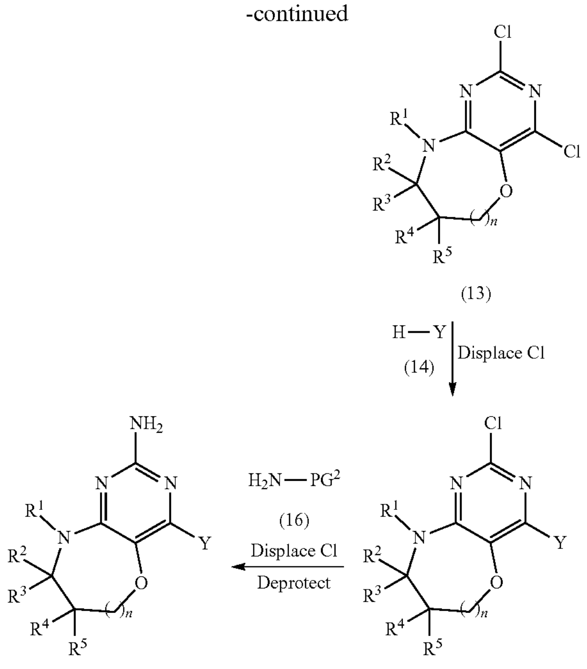

(13) (15) (17)

Thus, 2,4,6-trichloropyrimidin-5-ol (10), which is easily accessible via dealkylation of commercially available 2,4,6-trichloro-5-methoxypyrimidine, is reacted with a protected amino alcohol of formula (11), wherein $R^1$, $R^2$, $R^3$, $R^4$, $R^5$ and n are as defined above and $PG^1$ represents a suitable amino protecting group such as Boc, Cbz, Fmoc, Teoc or Bn, under Mitsunobu conditions to afford a substituted trichloropyrimidine of formula (12), wherein $R^1$, $R^2$, $R^3$, $R^4$, $R^5$ and n are as defined in above and $PG^1$ represents a suitable amino protecting group such as Boc, Cbz, Fmoc, Teoc or Bn. Typically, the Mitsunobu reaction is carried out using a trisubstituted phosphine reagent such as $Ph_3P$ or $Bu_3P$ in the presence of an azodicarboxylate species such as DEAD, DIAD or TMAD in a solvent such as THF, toluene, MeCN or DCM at about 0° C. to about room temperature, or occasionally with moderate heating at about 50° C. to 100° C.

Once formed, the amino function of the substituted trichloropyrimidine of formula (12) can be deprotected using conditions pertinent to the nature of the protecting group $PG^1$, and well understood by the skilled person, and the resulting product then cyclised via an intramolecular SNAr displacement reaction or via an intramolecular transition metal catalysed coupling reaction to form a compound of formula (13), wherein $R^1$, $R^2$, $R^3$, $R^4$, $R^5$ and n are as defined above. The SNAr displacement reaction is typically carried out in the presence of a tertiary amine base such as TEA or DIPEA, or an inorganic base such as $K_2CO_3$, $Cs_2CO_3$, $Na_2CO_3$ or $NaHCO_3$, or a strong base such as KOtBu, NaH or LiHMDS, in a suitable solvent such as 1,4-dioxane, THF, DMF, acetone, DCM, MeCN, $H_2O$, EtOH, IPA, DMSO or NMP, or a combination of suitable solvents, at a temperature between about room temperature to about 200° C., using conventional heating or optionally by heating with microwave irradiation, in an open vessel or optionally in a sealed vessel, optionally at a pressure greater than atmospheric pressure. The transition metal catalyzed coupling reaction is typically carried out in the presence of an alkoxide base such as NaOtBu or KOtBu, an inorganic base such as $K_3PO_4$, $K_2CO_3$, $Cs_2CO_3$ or NaOCN, or a tertiary amine base such as TEA or DIPEA, or a combination of suitable bases, in a suitable solvent such as 1,4-dioxane, THF, DME, $^t$BuOH or toluene, or a combination of suitable solvents, in the presence of a sub-stoichiometric quantity of a transition metal catalyst such as $Pd(OAc)_2$ (CAS: 3375-31-3), $Pd_2(dba)_3$ (CAS: 51364-51-3), $Pd(dppf)Cl_2$ (CAS: 72287-26-4), $Pd(PPh_3)_2Cl_2$ (CAS: 13965-03-2) or $Pd(PPh_3)_4$ (CAS: 14221-01-3), optionally in the presence of a sub-stoichiometric quantity of a phosphine ligand such as $Ph_3P$, $Bu_3P$, $^tBu_3P$, XPhos (CAS: 564483-18-7), Xantphos (CAS: 161265-03-8), tBuBrettPhos (CAS: 1160861-53-9) or BINAP (CAS: 76189-55-4, 76189-56-5), at a temperature between about room temperature to about 200° C., using conventional heating or optionally by heating with microwave irradiation, in an open vessel or optionally in a sealed vessel, optionally at a pressure greater than atmospheric pressure.

Once formed, the compound of formula (13) can be reacted with an amine of formula (14), wherein Y is as defined above, using a SNAr displacement reaction or a transition metal catalysed coupling reaction analogous to those described above to displace the 4-chloro substituent in the compound of formula (13) and form a compound of formula (15), wherein $R^1$, $R^2$, $R^3$, $R^4$, $R^5$, n and Y are as defined above. Once formed, the 2-chloro substituent in the compound of formula (15) can be displaced with a suitably protected $NH_3$ equivalent (16), wherein $PG^2$ represents a protecting group or groups such as Boc, Cbz, $(Boc)_2$, Ac, Bz, Bn, $Bn_2$, PMB or DMB using another transition metal catalysed coupling reaction analogous to those described above. Finally, the protecting group or groups $PG^2$ can be removed using conditions pertinent to the nature of the protecting group $PG^2$, and well understood by the skilled person, to afford the desired compound of formula (17), wherein $R^1$, $R^2$, $R^3$, $R^4$, $R^5$, n and Y are as defined above.

It will be understood by the skilled person that the order of steps as laid out in Scheme 1 may be completed in a different sequence to that shown, without affecting the overall success of the synthesis of the desired compound of formula (17). For example in Scheme 2 below, displacement of the 4-chloro substituent in the substituted trichloropyrimidine of formula (12) by reaction with an amine of formula (14) using a SNAr displacement reaction or a transition metal catalysed coupling reaction as described above, can be conducted at Step 2 to form a substituted amino dichloropyrimidine of formula (18), wherein $R^1$, $R^2$, $R^3$, $R^4$, $R^5$, n and Y are as defined above and $PG^1$ represents a suitable amino protecting group such as Boc, Cbz, Fmoc, Teoc or Bn. Once formed, the amino function of the substituted amino dichloropyrimidine of formula (18) can be deprotected using conditions pertinent to the nature of the protecting group $PG^1$, and well understood by the skilled person, and the resulting product then cyclised via an intramolecular SNAr displacement reaction or via an intramolecular transition metal catalysed coupling reaction as described above to form a compound of formula (15). The synthesis of the desired compound of formula (17) from the compound of formula (15) then follows as described for Scheme 1.

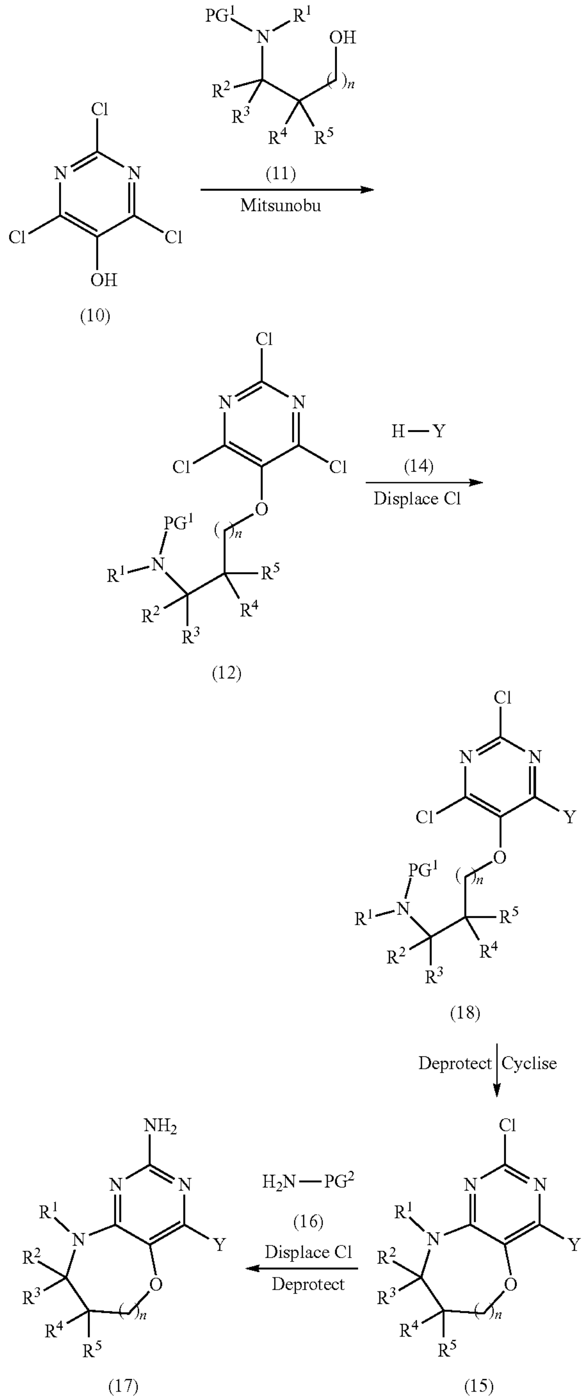

Alternatively, as set out in Scheme 3 below, displacement of the 4-chloro substituent with an amine of formula (14) can take place directly on 2,4,6-trichloropyrimidin-5-ol (10) in Step 1 of the sequence, using a SNAr displacement reaction or a transition metal catalysed coupling reaction analogous to those described above, to form a 4-amino-2,6-dichloro-pyrimidin-5-ol analogue of formula (19), wherein Y is as defined above. Once formed, the 4-amino-2,6-dichloropy-rimidin-5-ol analogue of formula (19) may then undergo reaction with a protected amino alcohol of formula (11) in Step 2, using Mitsunobu conditions analogous to those described above, to form the substituted amino dichloropy-rimidine of formula (18). The synthesis of the desired compound of formula (17) from the substituted amino dichloropyrimidine of formula (18) then follows as described for Scheme 2.

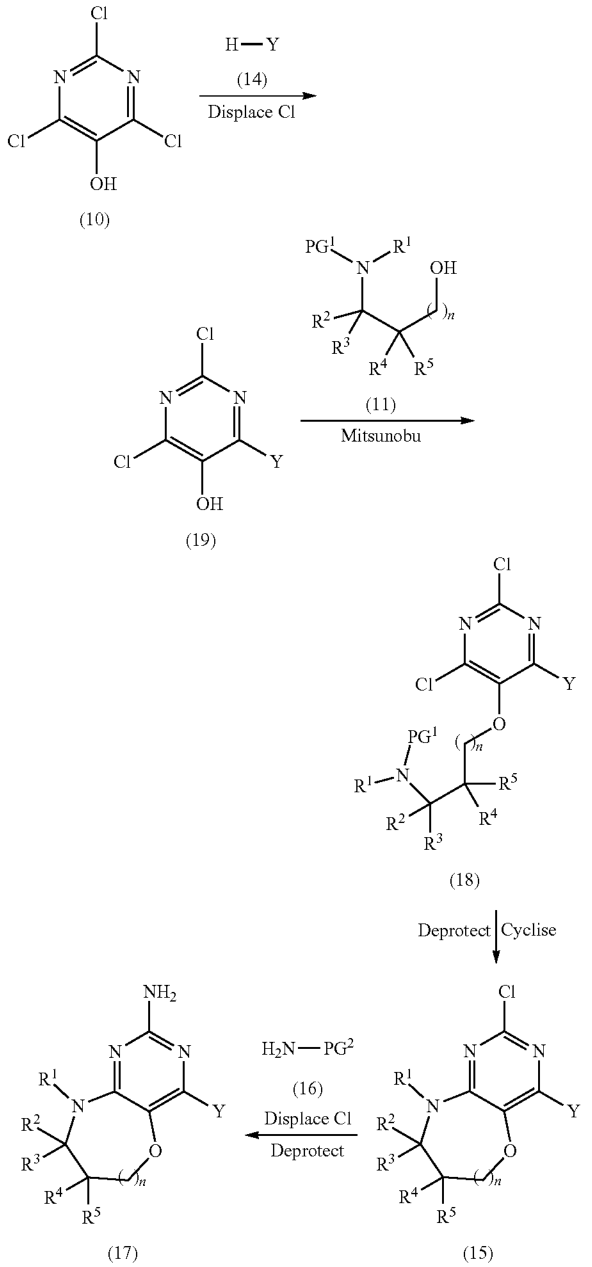

Scheme 4 below shows yet another variation, where a protected 2,4,6-trichloropyrimidin-5-ol of formula (20), wherein $PG^3$ represents a suitable phenolic OH protecting group such as Me or PMB, is reacted with an amino alcohol of formula (21), wherein $R^1$, $R^2$, $R^3$, $R^4$, $R^5$ and n are as defined above, to displace the 4-chloro substituent in pro-tected 2,4,6-trichloropyrimidin-5-ol of formula (20) using a SNAr displacement reaction or a transition metal catalysed coupling reaction analogous to those described above to form a protected 4-amino-2,6-dichloropyrimidin-5-ol of for-mula (22). Removal of the protecting group $PG^3$ in protected 4-amino-2,6-dichloropyrimidin-5-ol of formula (22) via conditions appropriate to the nature of $PG^3$, and well understood by the skilled person, then allows an intramolecular Mitsunobu reaction analogous to those described above to be conducted to form a compound of formula (13). The synthesis of the desired compound of formula (17) from the compound of formula (13) then follows as described for Scheme 1.

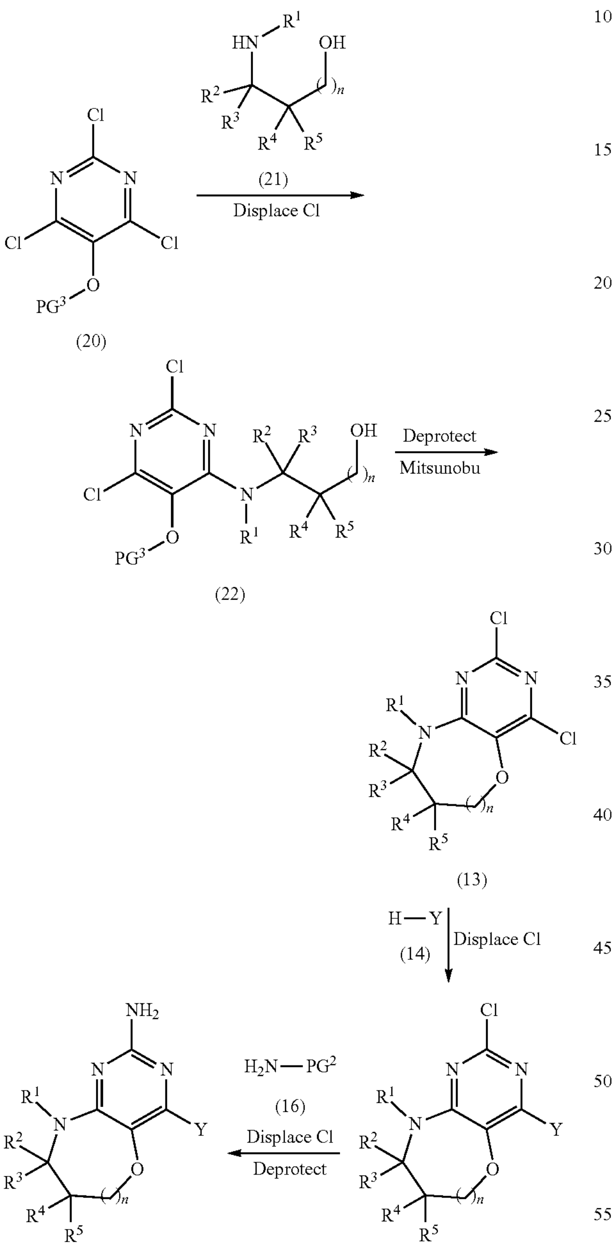

(20) (21) (22) (13) (14) (15) (16) (17)

The skilled person will understand that the reaction steps depicted in Schemes 1 to 4 may be combined in different ways as required to successfully prepare the desired compound of formula (17). It will also be obvious that there may be additional steps involving functional group modification, protection or deprotection introduced into the overall synthetic sequence. For example: carboxylic acid or ester groups may be reduced to alcohols, and the resulting alcohol then protected with a silyl-based protecting group; amide groups, nitriles or nitro groups may be reduced to amines, and the resulting amine then protected with a carbamate-based protecting group; primary or secondary amines may be further substituted using an alkylation reaction; Boc protecting groups may be reduced to methyl groups.

(B) When it is required to prepare a compound of formula (1) wherein Z is H: The sequence of reactions illustrated previously in Schemes 1 to 4 above, but starting either from 4,6-dichloropyrimidin-5-ol (23) or a protected 4,6-dichloropyrimidin-5-ol of formula (24), wherein $PG^3$ represents a suitable phenolic OH protecting group such as Me or PMB, to give the desired compound of formula (25), wherein $R^1$, $R^2$, $R^3$, $R^4$, $R^5$, n and Y are as defined above:

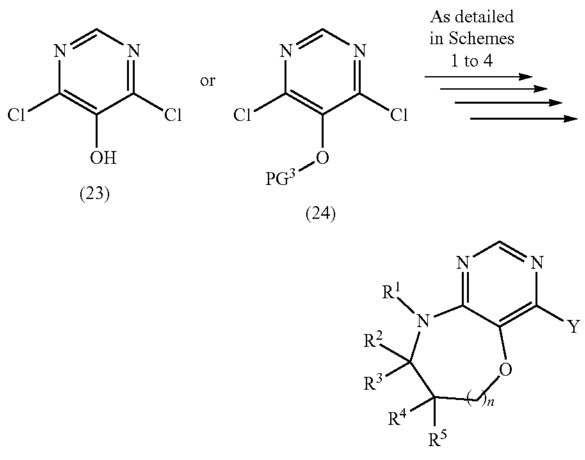

(23) or (24) (25)

Alternatively, the 2-chloro substituent in a compound of formula (15) can be removed to give the desired compound of formula (25) using reductive conditions, such as treatment with $H_2$ gas, in a solvent such as MeOH or EtOH, in the presence of a transition metal catalyst such as palladium on carbon or palladium hydroxide on carbon, optionally in the presence of a tertiary amine base such as $Et_3N$ or DIPEA, optionally at a pressure greater than atmospheric pressure. Alternatively, reductive dichlorination can be conducted using ammonium formate, in a solvent such as MeOH or EtOH, in the presence of a transition metal catalyst such as palladium on carbon or palladium hydroxide on carbon, at a temperature of between about room temperature to about the boiling temperature of the solvent that is used:

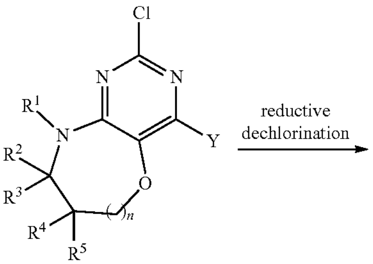

(15)

-continued

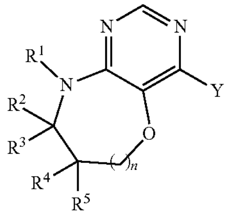

(25)

(C) When it is required to prepare a compound of formula (1) wherein Z is methyl: The sequence of reactions illustrated previously in Schemes 1 to 4 above, but starting either from 4,6-dichloro-2-methylpyrimidin-5-ol (26) or a protected 4,6-dichloro-2-methylpyrimidin-5-ol of formula (27), wherein $PG^3$ represents a suitable phenolic OH protecting group such as Me or PMB, to give the desired compound of formula (28), wherein $R^1$, $R^2$, $R^3$, $R^4$, $R^5$, n and Y are as defined above:

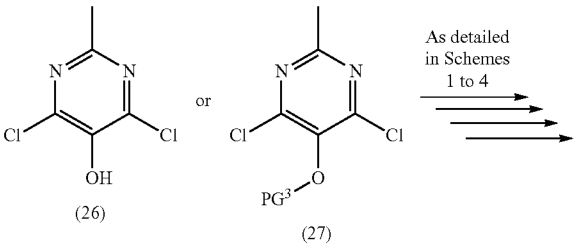

(26) or (27)

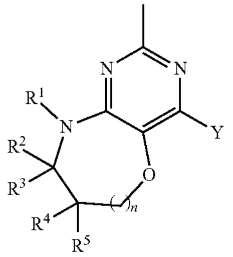

(28)

Alternatively, the 2-chloro substituent in a compound of formula (15) can be replaced with a methyl group using a transition metal catalysed coupling reaction, such as treatment with $MeB(OH)_2$, MeBPin (CAS: 94242-85-0) or trimethylboroxine (CAS: 823-96-1), in the presence of a palladium catalyst such as $Pd(PPh_3)_4$ (CAS: 14221-01-3), $PdCl_2$(dppe) (CAS: 19978-61-1), $Pd(dppf)Cl_2$ (CAS: 72287-26-4) or $Pd_2(dba)_3$ (CAS: 51364-51-3), optionally in the presence of a phosphine ligand such as $P(Cy)_3$, in the presence of an inorganic base such as $K_2CO_3$ or $Cs_2CO_3$, in a suitable solvent such as 1,4-dioxane, $H_2O$, THF or DME, or a mixture of suitable solvents, at a temperature between about room temperature to about 200° C., using conventional heating or optionally by heating with microwave irradiation, in an open vessel or optionally in a sealed vessel, optionally at a pressure greater than atmospheric pressure. Alternatively, other methods well known to the skilled person can be used such as MeMgBr or MeMgCI in combination with a nickel catalyst such as $Ni(dppf)Cl_2$ (CAS: 67292-34-6), in a solvent such as THF, $Et_2O$, DME or 1,4-dioxane at elevated temperatures; $Me_2Zn$ in combination with a palladium catalyst such as $PdCl_2$(dppe) (CAS: 19978-61-1) or $Pd(dppf)Cl_2$ (CAS: 72287-26-4), in a solvent such as toluene or 1,4-dioxane at elevated temperatures; $Me_3Al$ in combination with a palladium catalyst such as $Pd(PPh_3)_4$ (CAS: 14221-01-3), in a solvent such as THF, hexane or heptane at elevated temperatures; or $Me_4Sn$ in combination with a palladium catalyst such as $Pd(PPh_3)_4$ (CAS: 14221-01-3), in a solvent such as THF or DMF at elevated temperatures.

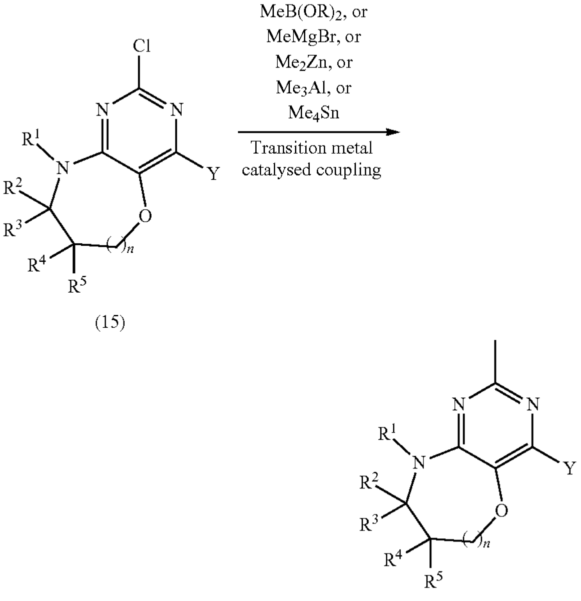

(15) (28)

(E) converting one compound of the formula (1) to another compound of the formula (1): Additionally, one compound of the formula (1) can be converted into another compound of the formula (1) by methods well known to the skilled person. Examples of synthetic procedures for converting one functional group into another functional group are set out in standard texts such as March's Advanced Organic Chemistry: Reactions, Mechanisms, and Structure, 7th Edition, Michael B. Smith, John Wiley, 2013, (ISBN: 978-0-470-46259-1), Organic Syntheses, Online Edition, www.orgsyn.org, (ISSN 2333-3553) and Fiesers' Reagents for Organic Synthesis, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in Greene's Protective Groups in Organic Synthesis, Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography) under normal or reversed-phase conditions, HPLC and SFC.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of the formula (1) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragees, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples.

Examples 1-1 to 17-15

The compounds of Examples 1-1 to 17-15 shown in Table 1 below have been prepared. NMR and LCMS properties and the methods used to prepare them are set out in Table 3. Starting materials are listed in Table 2.

TABLE 1
| Example compounds |
| --- |
| 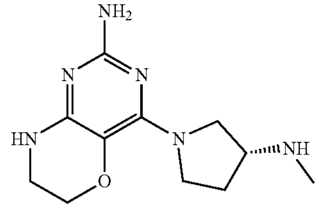 |
| Example 1-1 |
| 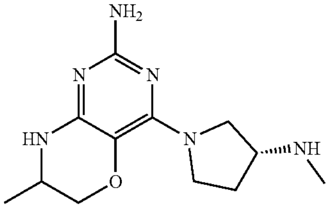 |
| Example 1-2 |
| 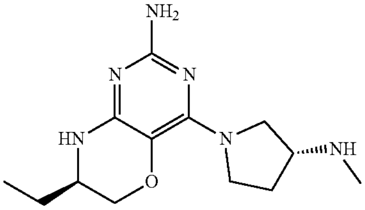 |
| Example 1-3 |
| 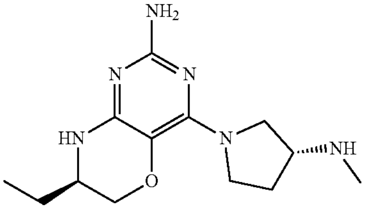 [SMILES: CC[C@@H]1COc2c(nc(N)nc2N2CC[C@@H](NC)C2)N1] |
| Example 1-4 |
| 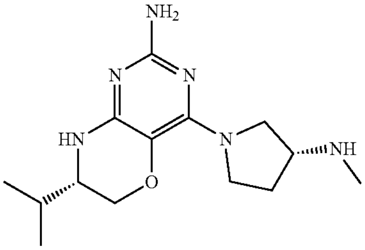 [SMILES: CN[C@@H]1CCN(c2nc(N)nc3c2OC[C@H](C(C)C)N3)C1] |
| Example 1-5 |
| 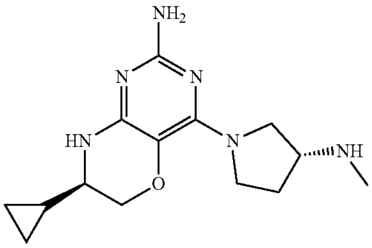 [SMILES: CN[C@@H]1CCN(c2nc(N)nc3c2OC[C@@H](C2CC2)N3)C1] |
TABLE 1-continued
| Example compounds |
| --- |
| Example 1-6 |
| 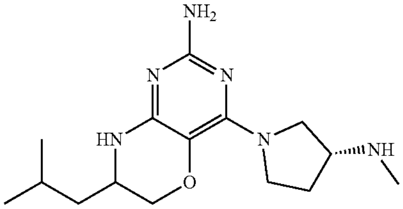 [SMILES: CN[C@@H]1CCN(c2nc(N)nc3c2OCC(CC(C)C)N3)C1] |
| Example 1-7 |
| 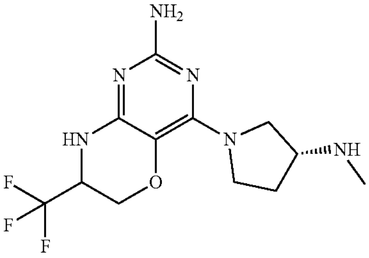 [SMILES: CN[C@@H]1CCN(c2nc(N)nc3c2OCC(C(F)(F)F)N3)C1] |
| Example 1-8 |
| 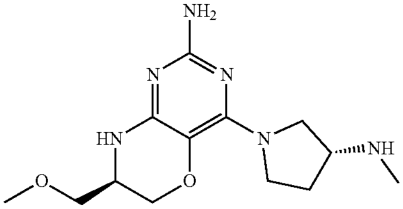 |
| Example 1-9 |
| 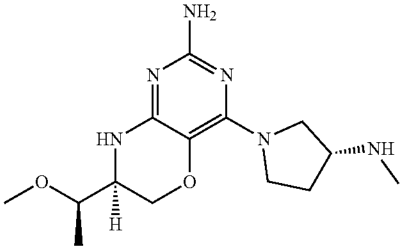 |
| Example 1-10 |
| 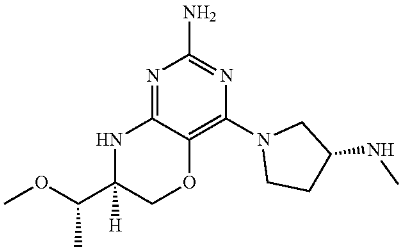 |
| Example 1-11 |

TABLE 1-continued
| Example compounds |
| --- |
| 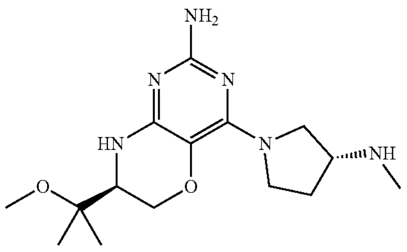 |
| Example 1-12 |
| 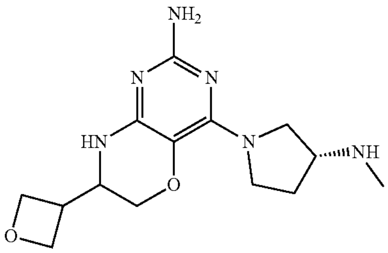 [SMILES: CN[C@@H]1CCN(c2nc(N)nc3c2OCC(C2COC2)N3)C1] |
| Example 1-13 |
| 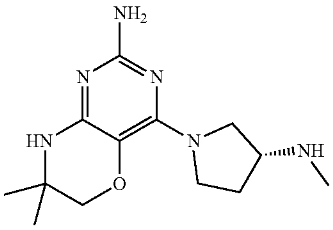 |
| Example 1-14 |
| 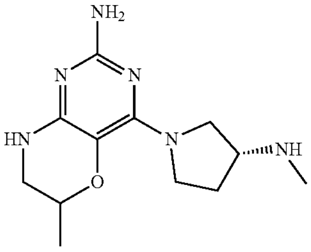 [SMILES: CN[C@@H]1CCN(c2nc(N)nc3c2OC(C)CN3)C1] |
| Example 1-15 |
| 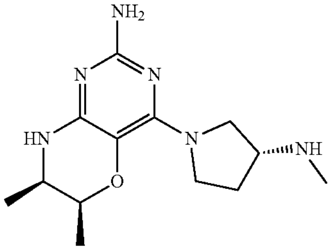 |
| Example 1-16 |
TABLE 1-continued
| Example compounds |
| --- |
| 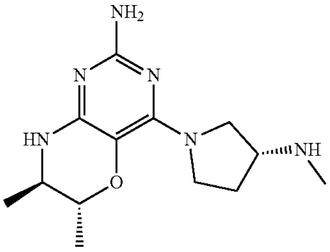 |
| Example 1-17 |
| 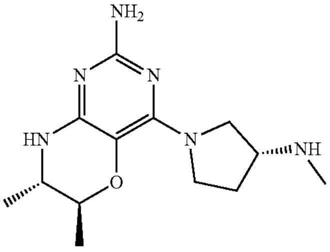 |
| Example 1-18 |
| 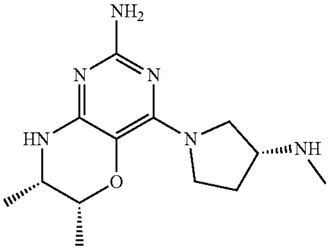 |
| Example 1-19 |
| 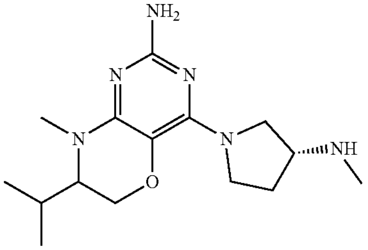 [SMILES: CN[C@@H]1CCN(c2nc(N)nc3c2OCC(C(C)C)N3C)C1] |
| Example 1-20 |
| 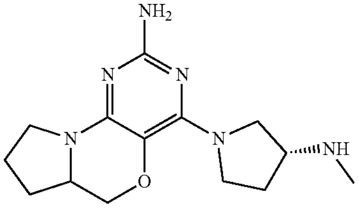 [SMILES: CN[C@@H]1CCN(c2nc(N)nc3c2OCC2CCCN32)C1] |
| Example 1-21 |

TABLE 1-continued
| Example compounds |
| --- |
| 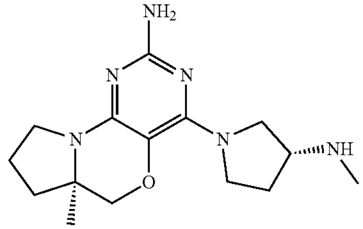 [SMILES: CN[C@@H]1CCN(c2nc(N)nc3c2OC[C@@]2(C)CCCN32)C1] |
| Example 1-22 |
| 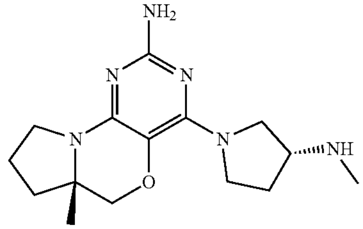 [SMILES: CN[C@@H]1CCN(c2nc(N)nc3c2OC[C@]2(C)CCCN32)C1] |
| Example 1-23 |
| 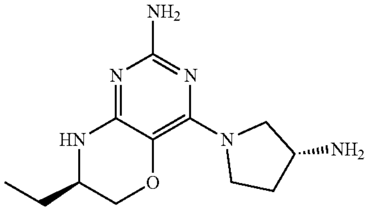 [SMILES: CC[C@@H]1COc2c(nc(N)nc2N2CC[C@@H](N)C2)N1] |
| Example 2-1 |
| 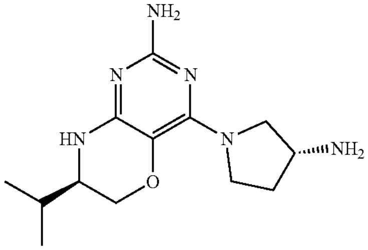 [SMILES: CC(C)[C@@H]1COc2c(nc(N)nc2N2CC[C@@H](N)C2)N1] |
| Example 2-2 |
| 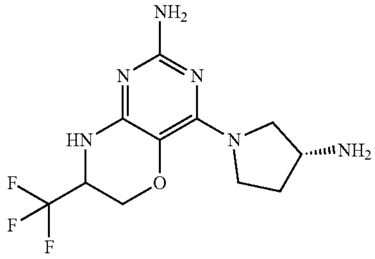 [SMILES: Nc1nc2c(c(N3CC[C@@H](N)C3)n1)OCC(C(F)(F)F)N2] |
| Example 2-3 |
TABLE 1-continued
| Example compounds |
| --- |
| 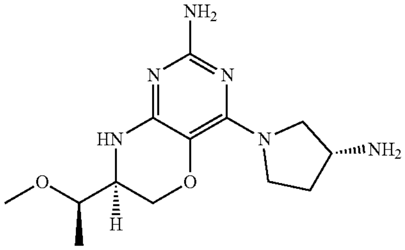 [SMILES: CO[C@H](C)[C@@H]1COc2c(nc(N)nc2N2CC[C@@H](N)C2)N1] |
| Example 2-4 |
| 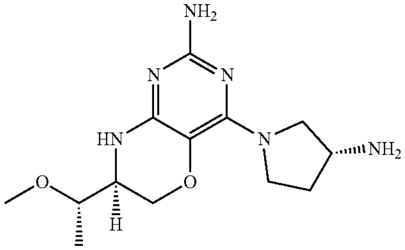 [SMILES: CO[C@@H](C)[C@@H]1COc2c(nc(N)nc2N2CC[C@@H](N)C2)N1] |
| Example 2-5 |
| 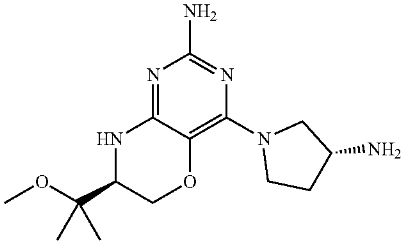 [SMILES: COC(C)(C)[C@@H]1COc2c(nc(N)nc2N2CC[C@@H](N)C2)N1] |
| Example 2-6 |
| 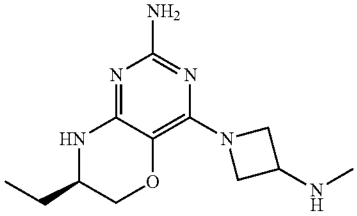 [SMILES: CC[C@@H]1COc2c(nc(N)nc2N2CC(NC)C2)N1] |
| Example 3-1 |
| 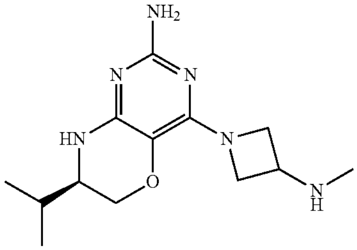 [SMILES: CNC1CN(c2nc(N)nc3c2OC[C@@H](C(C)C)N3)C1] |
| Example 3-2 |

TABLE 1-continued
Example compounds
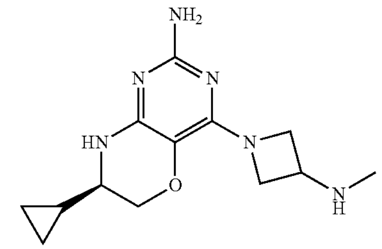 [SMILES: CNC1CN(c2nc(N)nc3c2OC[C@@H](C2CC2)N3)C1]
Example 3-3
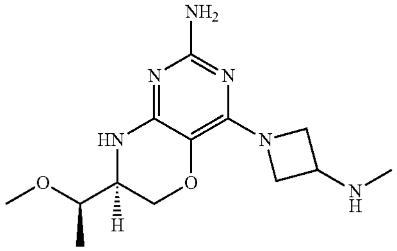
Example 3-4
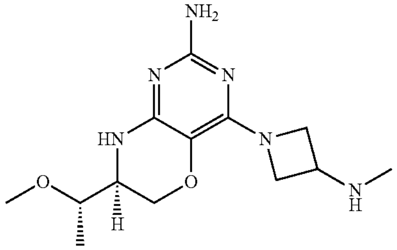
Example 3-5
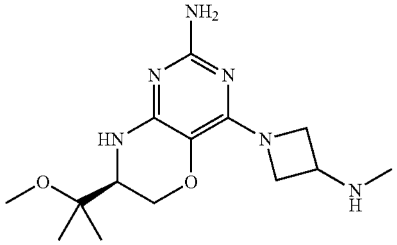
Example 3-6
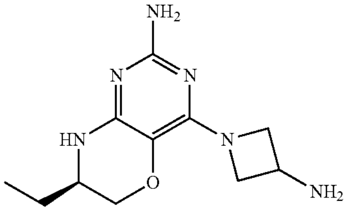
Example 4-1
TABLE 1-continued
Example compounds
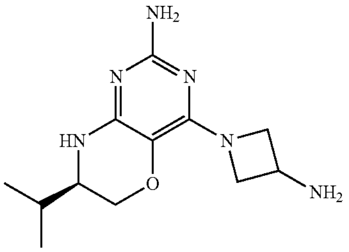 [SMILES: CC(C)[C@@H]1COc2c(nc(N)nc2N2CC(N)C2)N1]
Example 4-2
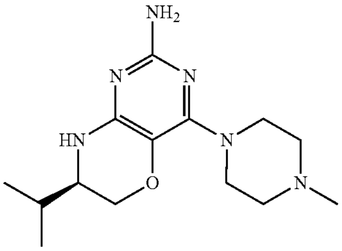 [SMILES: CC(C)[C@@H]1COc2c(nc(N)nc2N2CCN(C)CC2)N1]
Example 5-1
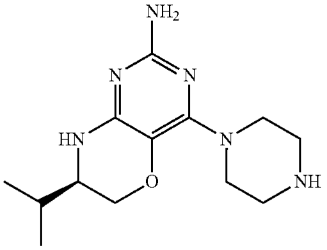 [SMILES: CC(C)[C@@H]1COc2c(nc(N)nc2N2CCNCC2)N1]
Example 6-1
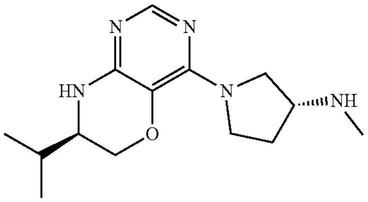 [SMILES: CN[C@@H]1CCN(c2ncnc3c2OC[C@@H](C(C)C)N3)C1]
Example 7-1
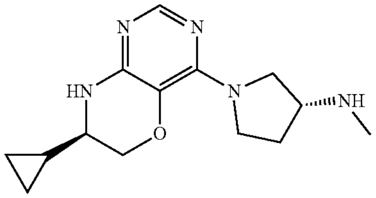 [SMILES: CN[C@@H]1CCN(c2ncnc3c2OC[C@@H](C2CC2)N3)C1]
Example 7-2
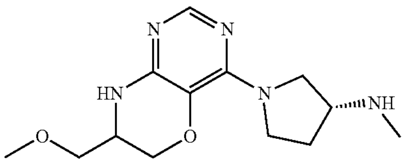
Example 7-3

TABLE 1-continued
Example compounds
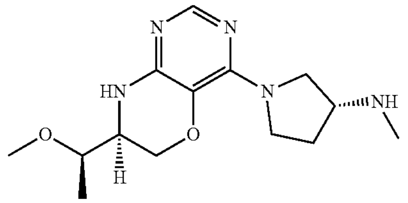
Example 7-4
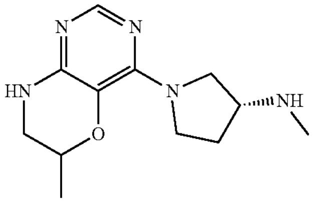 [SMILES: CN[C@@H]1CCN(c2ncnc3c2OC(C)CN3)C1]
Example 7-5
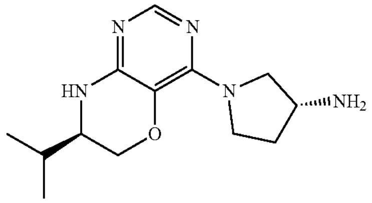 [SMILES: CC(C)[C@@H]1COc2c(ncnc2N2CC[C@@H](N)C2)N1]
Example 8-1
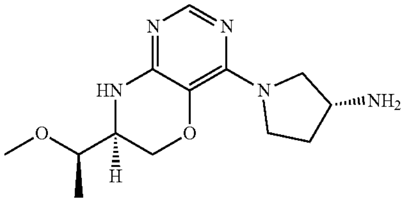 [SMILES: CO[C@H](C)[C@@H]1COc2c(ncnc2N2CC[C@@H](N)C2)N1]
Example 8-2
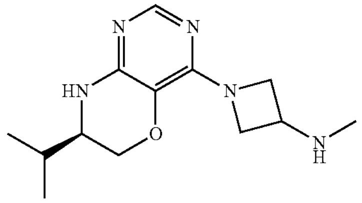 [SMILES: CNC1CN(c2ncnc3c2OC[C@@H](C(C)C)N3)C1]
Example 9-1
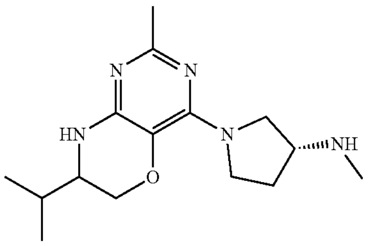 [SMILES: CN[C@@H]1CCN(c2nc(C)nc3c2OCC(C(C)C)N3)C1]
Example 10-1
TABLE 1-continued
Example compounds
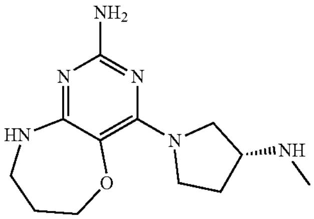 [SMILES: CN[C@@H]1CCN(c2nc(N)nc3c2OCCCN3)C1]
Example 11-1
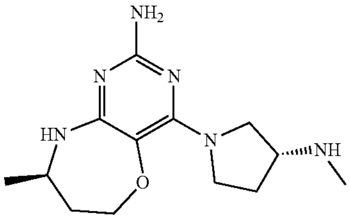
Example 11-2
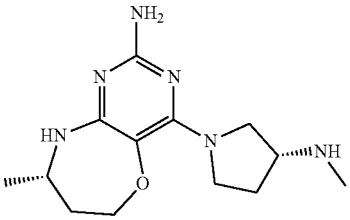
Example 11-3
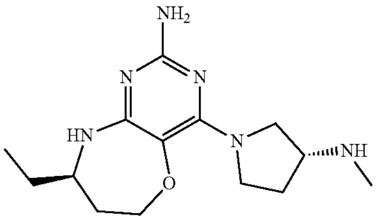 [SMILES: CC[C@@H]1CCOc2c(nc(N)nc2N2CC[C@@H](NC)C2)N1]
Example 11-4
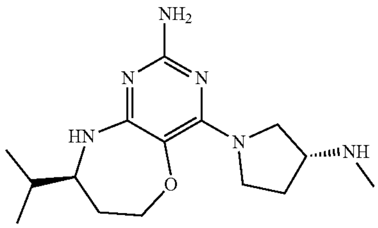 [SMILES: CN[C@@H]1CCN(c2nc(N)nc3c2OCC[C@@H](C(C)C)N3)C1]
Example 11-5

TABLE 1-continued
| Example compounds |
| --- |
| 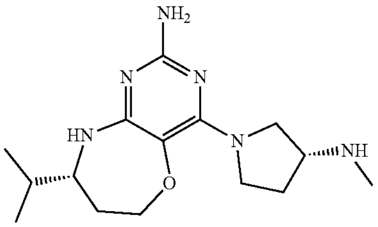 [SMILES: CN[C@@H]1CCN(c2nc(N)nc3c2OCC[C@H](C(C)C)N3)C1] |
| Example 11-6 |
| 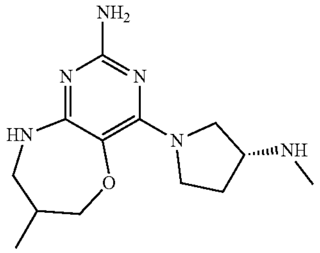 [SMILES: CN[C@@H]1CCN(c2nc(N)nc3c2OCC(C)CN3)C1] |
| Example 11-7 |
| 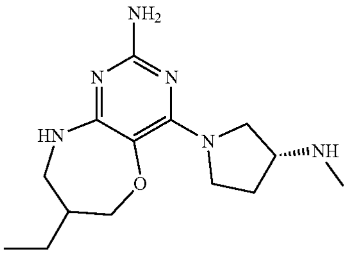 [SMILES: CCC1CNc2nc(N)nc(N3CC[C@@H](NC)C3)c2OC1] |
| Example 11-8 |
| 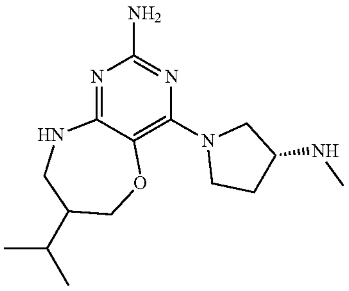 [SMILES: CN[C@@H]1CCN(c2nc(N)nc3c2OCC(C(C)C)CN3)C1] |
| Example 11-9 |
| 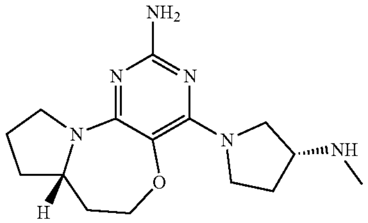 [SMILES: CN[C@@H]1CCN(c2nc(N)nc3c2OCC[C@@H]2CCCN32)C1] |
| Example 11-10 |
TABLE 1-continued
| Example compounds |
| --- |
| 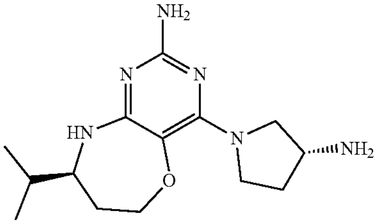 [SMILES: CC(C)[C@@H]1CCOc2c(nc(N)nc2N2CC[C@@H](N)C2)N1] |
| Example 12-1 |
| 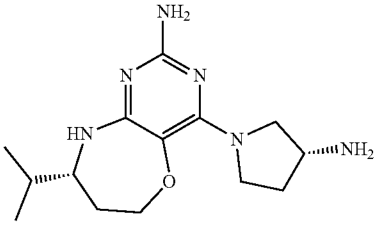 [SMILES: CC(C)[C@H]1CCOc2c(nc(N)nc2N2CC[C@@H](N)C2)N1] |
| Example 12-2 |
| 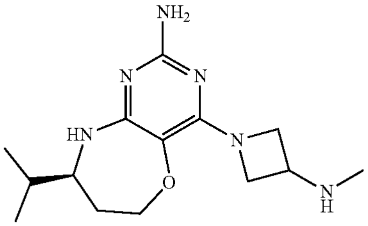 [SMILES: CNC1CN(c2nc(N)nc3c2OCC[C@@H](C(C)C)N3)C1] |
| Example 13-1 |
| 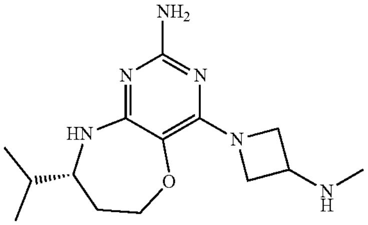 [SMILES: CNC1CN(c2nc(N)nc3c2OCC[C@H](C(C)C)N3)C1] |
| Example 13-2 |
| 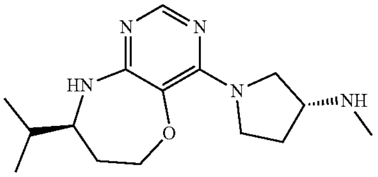 [SMILES: CN[C@@H]1CCN(c2ncnc3c2OCC[C@@H](C(C)C)N3)C1] |
| Example 14-1 |
| 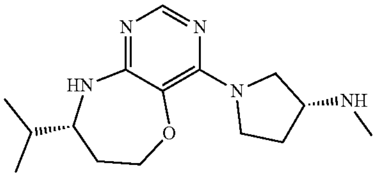 [SMILES: CN[C@@H]1CCN(c2ncnc3c2OCC[C@H](C(C)C)N3)C1] |
| Example 14-2 |

TABLE 1-continued
| Example compounds |
| --- |
| 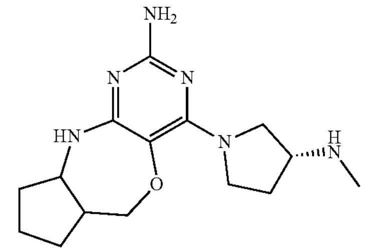 [SMILES: CN[C@@H]1CCN(c2nc(N)nc3c2OCC2CCCC2N3)C1] |
| Example 17-1 |
| 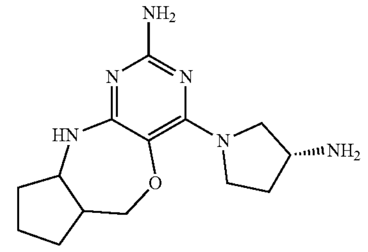 [SMILES: Nc1nc2c(c(N3CC[C@@H](N)C3)n1)OCC1CCCC1N2] |
| Example 17-2 |
| 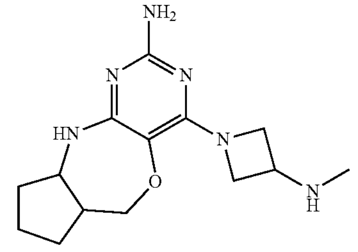 [SMILES: CNC1CN(c2nc(N)nc3c2OCC2CCCC2N3)C1] |
| Example 17-3 |
| 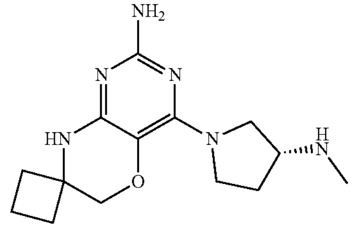 [SMILES: CN[C@@H]1CCN(c2nc(N)nc3c2OCC2(CCC2)N3)C1] |
| Example 17-4 |
| 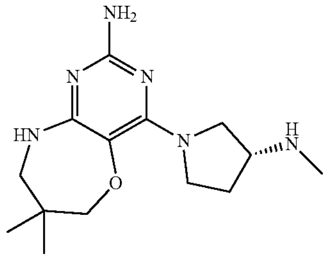 |
| Example 17-5 |
TABLE 1-continued
| Example compounds |
| --- |
| 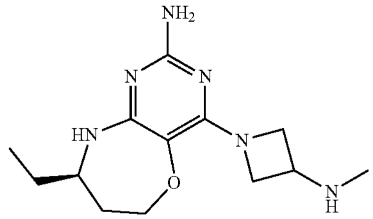 [SMILES: CC[C@@H]1CCOc2c(nc(N)nc2N2CC(NC)C2)N1] |
| Example 17-6 |
| 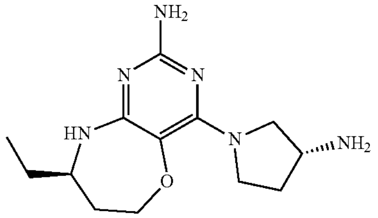 [SMILES: CC[C@@H]1CCOc2c(nc(N)nc2N2CC[C@@H](N)C2)N1] |
| Example 17-7 |
| 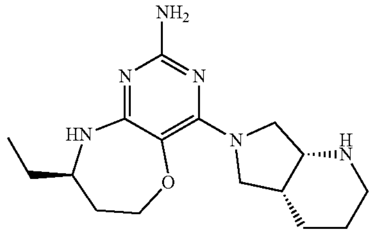 [SMILES: CC[C@@H]1CCOc2c(nc(N)nc2N2C[C@H]3CCCN[C@H]3C2)N1] |
| Example 17-8 |
| 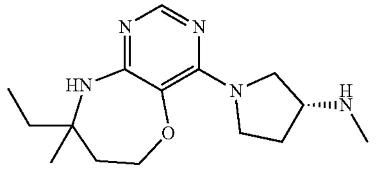 [SMILES: CCC1(C)CCOc2c(ncnc2N2CC[C@@H](NC)C2)N1] |
| Example 17-9 |
| 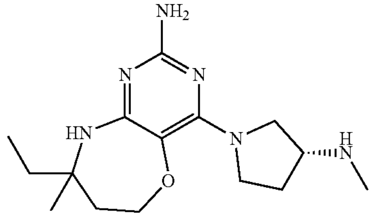 [SMILES: CCC1(C)CCOc2c(nc(N)nc2N2CC[C@@H](NC)C2)N1] |
| Example 17-10 |
| 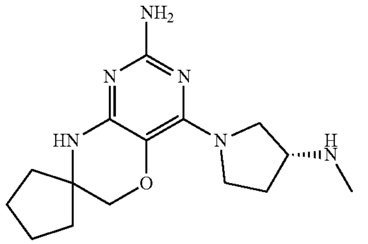 [SMILES: CN[C@@H]1CCN(c2nc(N)nc3c2OCC2(CCCC2)N3)C1] |
| Example 17-11 |

TABLE 1-continued

| Example compounds |
|---|
| 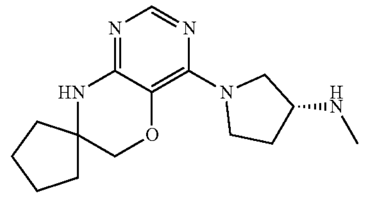 [SMILES: CN[C@@H]1CCN(c2ncnc3c2OCC2(CCCC2)N3)C1] |
| Example 17-12 |
| 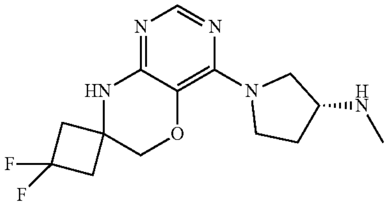 [SMILES: CN[C@@H]1CCN(c2ncnc3c2OCC2(CC(F)(F)C2)N3)C1] |
| Example 17-13 |
| 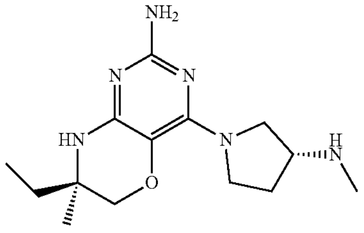 [SMILES: CC[C@]1(C)COc2c(nc(N)nc2N2CC[C@@H](NC)C2)N1] |
| Example 17-14 |
| 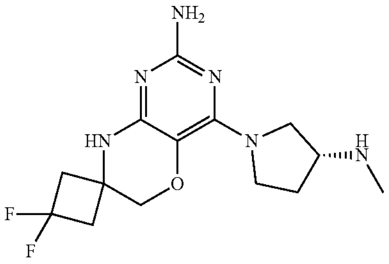 [SMILES: CN[C@@H]1CCN(c2nc(N)nc3c2OCC2(CC(F)(F)C2)N3)C1] |
| Example 17-15 |

General Procedures

Where no preparative routes are included, the relevant intermediate is commercially available. Commercial reagents were utilized without further purification. Final compounds and intermediates are named using ChemDraw Professional, Version 17.0.0.206 (121). Room temperature (RT) refers to approximately 20-27° C. $^1$H NMR spectra were recorded at 400 or 500 MHz on either a Bruker, Varian or Jeol instrument. Chemical shift values are expressed in parts per million (ppm), i.e. (S)-values relative to the following solvents: chloroform-d=7.26 ppm, DMSO-$d_6$=2.50 ppm, methanol-$d_4$=3.31 ppm. The following abbreviations are used for the multiplicity of the NMR signals: s=singlet, br=broad, d=doublet, t=triplet, q=quartet, m=multiplet. Coupling constants are listed as J values, measured in Hz. NMR and mass spectroscopy results were corrected to account for background peaks. Chromatography refers to column chromatography performed using 60-120 mesh or 40-633 μm, 60 Å silica gel and executed under nitrogen pressure (flash chromatography) conditions. PL-$HCO_3$ MP SPE refers to StratoSpheres $HCO_3^-$ bound macroporous polystyrene Solid Phase Extraction cartridges available from Polymer Laboratories. Microwave-mediated reactions were performed in Biotage Initiator or CEM Discover microwave reactors.

LCMS Analysis

LCMS analysis of compounds was performed under electrospray conditions using the instruments and methods given in the tables below:

| System | Instrument Name | LC Detector | Mass Detector |
|---|---|---|---|
| 1 | Agilent 1100 | Photo Diode Array | ZQ-2000 |
| 2 | Waters Acquity UPLC | Photo Diode Array | SQ detector |
| 3 | Waters Acquity H Class | Photo Diode Array | SQ Detector |
| 4 | Shimadzu Nexera | Photo Diode Array | LCMS-2020 |
| 5 | Waters Acquity H Class | Photo Diode Array | QDa Mass Detector |

| Method Name | Solvent System | Column used | Gradient | UV Range | Mass Range | Column Temp. ° C. | Flow Rate ml/min |
|---|---|---|---|---|---|---|---|
| A | (A) 5 mM ammonium acetate + 0.1% formic acid in water (B) 0.1% formic acid in acetonitrile | Waters BEH C-18 2.1 × 50 mm, 1.7 μm or equivalent | 98:2 at 0.01 min up to 0.50 min, 10:90 at 5.00 min, 5:95 at 6.00 min up to 7.00 min, 98:2 at 7.01 min up to 8.00 min | 200-400 nm | 60-1000 amu | Ambient | 0.45 |
| B | (A) 2 mM ammonium acetate + 0.1% formic acid in water (B) 0.1% formic acid in acetonitrile | Waters BEH C-18 2.1 × 50 mm, 1.7 μm or equivalent | 98:2 at 0.01 min up to 0.30 min (0.55 ml/min), 50:50 at 0.60 min (0.55 ml/min), 25:75 at 1.10 min (0.55 ml/min), 0:100 at 2.00 min up to 2.70 min (0.60 ml/min), 98:2 at 2.71 min up to 3.00 min (0.55 ml/min) | 200-400 nm | 100-1200 amu | Ambient | 0.55-0.60 |

-continued

| Method Name | Solvent System | Column used | Gradient | UV Range | Mass Range | Column Temp. ° C. | Flow Rate ml/min |
|---|---|---|---|---|---|---|---|
| C | (A) 5 mM ammonium bicarbonate in water (B) acetonitrile | Waters X-Bridge C-18 4.6 × 50 mm, 3.5 μm or equivalent | 95:5 at 0.01 min, 10:90 at 5.0 min, 5:95 at 5.80 min up to 7.20 min, 95:5 at 7.21 min up to 10.0 min | 200-400 nm | 60-1000 amu | Ambient | 1.00 |
| D | (A) 10 mM ammonium formate in water, pH 3.8 (B) acetonitrile | Phenomenex Kinetex C-18 4.6 × 50 mm, 5 μm | 95:5 at 0.01 min up to 0.50 min, 95:5 to 0:100 between 0.50 min and 2.50 min and 0:100 between 2.50 min and 3.50 min | 190-320 nm | 100-750 amu | 30 | 2.2 |
| E | (A) 10 mM ammonium bicarbonate in water, pH 10 (B) acetonitrile | Phenomenex Gemini-NX C-18 4.6 × 50 mm, 5 μm | 95:5 at 0.01 min up to 0.50 min, 95:5 to 0:100 between 0.50 min and 2.50 min and 0:100 between 2.50 min and 3.50 min | 190-320 nm | 100-750 amu | 30 | 2.2 |
| F | (A) 10 mM ammonium carbonate in water, pH 10 (B) acetonitrile | Waters BEH C-18 2.1 × 50 mm, 1.7 μm | 95:5 to 0:100 between 0.01 and 2.30 min (0.7 ml/min), 0:100 between 2.30 and 2.40 min (0.7 to 0.8 mL/min) and 0:100 between 2.40 to 3.00 min (0.8 mL/min) | 190-320 | 150-2000 amu | 30 | 0.7-0.8 |
| G | (A) 10 mM ammonium bicarbonate in water, pH 10 (B) acetonitrile | Waters BEH C-18 2.1 × 50 mm, 1.7 μm | 95:5 to 0:100 between 0.01 and 2.30 min (0.7 ml/min), 0:100 between 2.30 and 2.40 min (0.7 to 0.8 mL/min) and 0:100 between 2.40 to 3.00 min (0.8 mL/min) | 190-320 | 150-2000 amu | 30 | 0.7-0.8 |
| H | (A) 10 mM ammonium formate in water, pH 3.8 (B) acetonitrile | Waters BEH C-18 2.1 × 50 mm, 1.7 μm | 95:5 to 0:100 between 0.01 and 2.30 min (0.7 ml/min), 0:100 between 2.30 and 2.40 min (0.7 to 0.8 mL/min) and 0:100 between 2.40 to 3.00 min (0.8 mL/min) | 190-320 | 150-2000 amu | 30 | 0.7-0.8 |
| I | (A) 10 mM ammonium bicarbonate in water, pH 10 (B) acetonitrile | Waters BEH C-18 2.1 × 50 mm, 1.7 μm | 95:5 to 0:100 between 0.01 and 2.30 min (0.7 ml/min), 0:100 between 2.30 and 2.40 min (0.7 to 0.8 mL/min) and 0:100 between 2.40 to 3.00 min (0.8 mL/min) | 190-400 | 150-2000 amu | 27 | 0.7-0.8 |
| J | (A) 50 mM ammonium acetate buffer, pH 7.4 (B) acetonitrile | Phenomenex Gemini-NX C18 2 × 30 mm, 3 μm | 100:0 at 0.00 min to 0:100 at 1.30 min, 0:100 between 1.30 and 1.55 min, 0:100 to 100:0 between 1.55 and 1.60 min, 100:0 between 1.60 and 3.0 min | 200-500 | 100-1200 amu | 40 | 0.5 |

LCMS data in the experimental section and Tables 2 and 3 are given in the format: (Instrument system, Method): Mass ion, retention time, UV detection wavelength.

Compound Purification

Final purification of compounds was performed by reversed-phase column chromatography, preparative reversed-phase HPLC, chiral HPLC or chiral SFC using the instruments and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Reversed-Phase Column Chromatography

Teledyne Isco instruments using pre-packaged disposable Silica-Based C18 (17%)/Silicycle/40-63 μm, 60 Å stationary phase columns with an eluent flow rate range of 15 to 200 mL/min and UV detection (254 and 280 nm).

Preparative HPLC Purification:

Shimadzu LC-20AP binary system with SPD-20 Å UV detector

Waters 2767 with PDA detector and mass triggered with a Waters ZQ equipped with an electrospray ion source operated in a positive ion mode Chiral HPLC Purification:

Shimadzu LC-20AP binary system with SPD-20 Å UV detector

Chiral SFC Purification:

WatersSFC 200

Purification Method A

Prep HPLC: [Reversed-phase (BEH C-18, 50×30 mm, 5 μm), 40 mL/min, gradient 5% (over 0.5 min), 5%-25% (over 6.4 min), 100% (over 1.6 min), 100%-5% (over 0.5 min), mobile phase (A): 10 mM ammonium carbonate in water, pH 10, (B): 100% acetonitrile].

Purification Method B

Prep HPLC: [Reversed-phase (BEH C-18, 50×30 mm, 5 μm), 40 mL/min, gradient 10% (over 0.5 min), 10%-30% (over 6.4 min), 100% (over 1.6 min), 100%-10% (over 0.5 min), mobile phase (A): 10 mM ammonium carbonate in water, pH 10, (B): 100% acetonitrile].

Purification Method C

Prep HPLC: [Reversed-phase (BEH C-18, 50×30 mm, 5 μm), 40 mL/min, gradient 10% (over 0.5 min), 10%-30% (over 6.4 min), 100% (over 1.6 min), 100%-10% (over 0.5 min), mobile phase (A): 10 mM ammonium bicarbonate in water, pH 10, (B): 100% acetonitrile].

Purification Method D

Prep HPLC: [Reversed-phase (BEH C-18, 50×30 mm, 5 μm), 40 mL/min, gradient 22% (over 0.5 min), 22%-42% (over 6.4 min), 100% (over 1.6 min), 100%-22% (over 0.5 min), mobile phase (A): 10 mM ammonium carbonate in water, pH 10, (B): 100% acetonitrile].

Purification Method E

Prep HPLC: [Reversed-phase (Gemini-NX 30×150 mm, 5 µm), 40 mL/min, gradient 10% (over 0.5 min), 10%-100% (over 6.4 min), 100% (over 1.6 min), 100%-10% (over 0.5 min), mobile phase (A): 10 mM ammonium bicarbonate in water, pH 10, (B) 100% acetonitrile].

Purification Method F

Prep HPLC: [Reversed-phase (X-BRIDGE C-18, 250×19 mm, 5 µm), 11 mL/min, gradient 10%-32% (over 30 min), 32% (over 4 min), 100% (over 2 min), 100%-10% (over 6 min), mobile phase (A): 5 mM ammonium bicarbonate+ 0.1% ammonia in water, (B): 100% acetonitrile].

Purification Method G

Prep HPLC: [Reversed-phase (BEH C-18, 150×30 mm, 5 µm), 40 mL/min, gradient 80% (over 0.5 min), 80%-100% (over 6.4 min), 100% (over 1.6 min), 100%-80% (over 0.5 min), mobile phase (A): 10 mM ammonium bicarbonate in water, pH 10, (B): 100% acetonitrile].

ABBREVIATIONS USED THROUGHOUT THIS DOCUMENT

Ac=acetate
aq.=aqueous
Bn=benzyl
Bz=benzoyl
Boc=tert-butyloxycarbonyl
$^{n}$BuOH=n-butanol
$^{t}$BuOH=t-butanol
$Bu_3P$=tri n-butylphosphine
$^{t}Bu_3P$=tri tert-butylphosphine
Cbz=benzyloxycarbonyl
COMU=(1-cyano-2-ethoxy-2-oxoethylidenaminooxy)dimethylamino-morpholino-carbenium hexafluorophosphate
DCM=dichloromethane
DEAD=diethyl azodicarboxylate
DIAD=diisopropylazodicarboxylate
DIC=N,N'-diisopropylcarbodiimide
DIPEA=N,N-diisopropylethylamine
DMA=N,N-dimethylacetamide
DMAP=4-(dimethylamino)pyridine
DMB=3,4-dimethoxybenzyl
DME=dimethoxyethane
DMF=N,N-dimethylformamide
DMSO=dimethylsulfoxide
EDC=1-ethyl-3-(3-dimethylaminopropyl)carbodiimide
ES=electro spray ionization
$Et_3N$=triethylamine
$Et_2O$=diethylether
EtOAc=ethyl acetate
EtOH=ethanol
Fmoc=fluorenylmethyloxycarbonyl
h=hour(s)
HATU=1-[bis(dimethylamino)methylene]-1H-1,2,3-triazolo[4,5-b]pyridinium 3-oxide hexafluorophosphate
$H_2O$=water
HCl=hydrogen chloride, hydrochloric acid
HOBt=hydroxybenzotriazole
HPLC=high performance liquid chromatography
IPA=propan-2-ol
LC=liquid chromatography
MeCN=acetonitrile
MeOH=methanol
min(s)=minute(s)
MS=mass spectrometry
nm=nanometre(s)
NMP=N-methyl-2-pyrrolidone
NMR=nuclear magnetic resonance
$P(Cy)_3$=tricyclohexylphosphine
PMB=4-methoxybenzyl
$PPh_3$, $Ph_3P$=triphenylphosphine
PTSA=para-toluenesulfonic acid
PyBOP=(benzotriazol-1-yloxy)tripyrrolidinophosphonium hexafluorophosphate
RP-flash=reversed-phased flash chromatography
RP-HPLC=reversed-phased high performance liquid chromatography
RT=room temperature
sat.=saturated
SFC=supercritical fluid chromatography
SNAr=nucleophilic aromatic substitution
TBAF=tetrabutylammonium fluoride
TEA=triethylamine
Teoc=pi-(trimethylsilyl)ethoxycarbonyl
TFA=trifluoroacetic acid
TFAA=trifluoroacetic anhydride
THF=tetrahydrofuran
TMAD=N,N,N',N'-tetramethylazodicarboxamide
T3P=2,4,6-tripropyl-1,3,5,2,4,6-trioxatriphosphorinane-2,4,6-trioxide

Synthesis of Intermediates

Route 1

Typical procedure for the preparation of Intermediate 2,2,4,6-trichloropyrimidin-5-ol

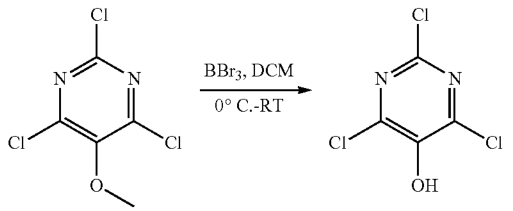

Intermediate 1 Intermediate 2

Under an atmosphere of nitrogen, a solution of 2,4,6-trichloro-5-methoxypyrimidine (Intermediate 1) (2.60 g, 12.2 mmol) in DCM (121 mL) was cooled to 0° C. and treated with boron tribromide (neat, 4.05 mL, 42.6 mmol) dropwise. After stirring for 18 h at room temperature, the reaction mixture was cooled below 0° C., carefully quenched with methanol (20 mL), then diluted with water (120 mL) and the phases were separated. The aqueous layer was extracted with DCM (3×100 mL) and the combined organic extracts were dried ($Na_2SO_4$), filtered and concentrated in-vacuo to give a pale tan solid (2.27 g). The crude material was purified by flash chromatography on silica gel (80 g cartridge) using 0% to 20% EtOAc in DCM to afford 2,4,6-trichloropyrimidin-5-ol (Intermediate 2) (1.67 g, 62%) as a white solid. The data for Intermediate 2 are in Table 2.

Route 2

Typical procedure for the preparation of protected amino alcohols, as exemplified by the preparation of Intermediate 10, tert-butyl (R)-(1-cyclopropyl-2-hydroxyethyl)carbamate

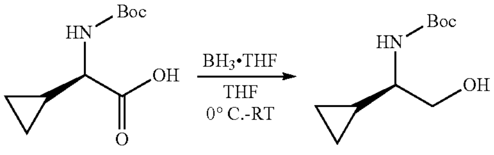

Intermediate 9 Intermediate 10

(R)-2-((tert-Butoxycarbonyl)amino)-2-cyclopropylacetic acid (Intermediate 9) (2 g, 0.009 mol) was dissolved in THE (20.0 mL) and cooled to 0° C. Borane THE complex solution in THF (1.0 M, 32 mL, 0.032 mol) was added dropwise at 0° C. and the resulting mixture was stirred at room temperature for 16 h. The reaction mixture was quenched by the addition of methanol, then the solvent was removed in-vacuo and the residue was partitioned between $H_2O$ (50 mL) and EtOAc (30 mL) and the phases were separated. The aqueous layer was further extracted with EtOAc (2×50 mL), and the combined organic layers were washed with aq. sat. $NaHCO_3$ solution. The organic layer was dried ($Na_2SO_4$) and the solvent was removed in-vacuo to give the crude product, which was purified by column chromatography (Normal-Phase 60-120 mesh silica gel, 0 to 30% EtOAc in hexanes) to give tert-butyl (R)-(1-cyclopropyl-2-hydroxyethyl)carbamate (Intermediate 10) (1.8 g, 96%) as a colourless gum.

The data for Intermediate 10 are in Table 2.

Route 3

Typical procedure for the preparation of protected amino alcohols, as exemplified by the preparation of Intermediate 14, tert-butyl ((2S,3R)-1-hydroxy-3-methoxybutan-2-yl)carbamate

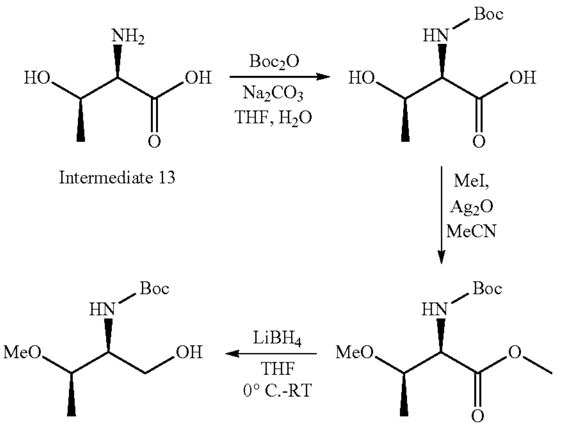

Intermediate 13

Intermediate 14

To a stirred solution of D-allothreonine (3.0 g, 25.2 mmol) in THF (41 mL) and $H_2O$ (41 mL) was added a solution of sodium carbonate (5.60 g, 52.8 mmol) in $H_2O$ (13 mL) and the resulting mixture was stirred for 5 minutes before adding di-tert-butyl dicarbonate (6.59 g, 30.2 mmol). The mixture was stirred at room temperature overnight, then water (15 mL) was added and the mixture was extracted with diethylether (2×10 mL). The aqueous layer was acidified with 1 M aqueous HCl to pH 4 and extracted with EtOAc (3×25 mL). The combined EtOAc layers were dried ($Na_2SO_4$) and concentrated in-vacuo to give (tert-butoxycarbonyl)-D-allothreonine (5.10 g, 92%) as a white solid.

H NMR (500 MHz, Chloroform-d) δ 1.23-1.36 (m, 3H), 1.45 (s, 9H), 4.06-4.24 (m, 1H), 4.30-4.41 (m, 1H), 5.58 (d, J=7.4 Hz, 1H), 6.16 (br. s, 2H).

To a stirred solution of (tert-butoxycarbonyl)-D-allothreonine (5.10 g, 23.3 mmol) in dry acetonitrile (320 mL) was added $Ag_2O$ (26.95 g, 116.0 mmol) and methyl iodide (14.5 mL, 233.0 mmol) at room temperature and the resulting mixture was stirred in the dark for 4 days.

The mixture was filtered through Celite and washed several times with DCM. The filtrate was concentrated in-vacuo to give the crude product, which was purified by flash chromatography (0-100% EtOAc in hexanes, 80 g $SiO_2$ cartridge) to give methyl N-(tert-butoxycarbonyl)-O-methyl-D-allothreoninate as a colorless liquid (3.80 g, 66%).

$^1$H NMR (400 MHz, Chloroform-d) δ 1.20 (d, J=6.5 Hz, 3H), 1.45 (s, 9H), 3.36 (s, 3H), 3.59-3.67 (m, 1H), 3.76 (s, 3H), 4.39-4.46 (m, 1H), 5.24-5.30 (m, 1H).

To a stirred solution of methyl N-(tert-butoxycarbonyl)-O-methyl-D-allothreoninate (3.80 g, 15.4 mmol) in THF (30 mL) under nitrogen was added $LiBH_4$ solution in THF (2.0 M, 11.5 mL, 23.1 mmol) at 0° C. and the mixture was slowly warmed to room temperature and stirred overnight. The reaction mixture was quenched with sat. aq. $NH_4Cl$ solution (15 mL) and extracted with ethyl acetate (3×25 mL). The combined organic extracts were dried over sodium sulfate and concentrated in-vacuo. The residue was purified by flash chromatography (0-100% EtOAc in hexanes, 80 g $SiO_2$ cartridge) to give tert-butyl ((2S,3R)-1-hydroxy-3-methoxybutan-2-yl)carbamate, (Intermediate 14) (3.10 g, 92%) as a colorless liquid.

The data for Intermediate 14 are in Table 2.

Route 4

Typical procedure for the preparation of protected amino alcohols, as exemplified by the preparation of Intermediate 18, tert-butyl (S)-(1-hydroxy-3-methoxy-3-methylbutan-2-yl)carbamate

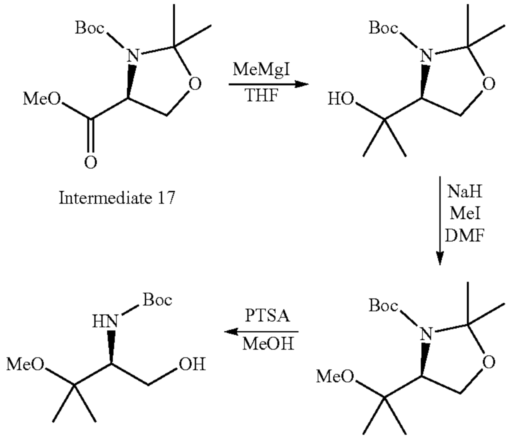

Intermediate 17

Intermediate 18

A solution of methyl iodide (3.6 mL, 57.8 mmol) in dry $Et_2O$ (39 mL) was added slowly to Mg filings (1.17 g, 48.2 mmol) in dry $Et_2O$ (10 mL). After complete consumption of the Mg, a solution of 3-(tert-butyl) 4-methyl (S)-2,2-dimethyloxazolidine-3,4-dicarboxylate (Intermediate 17) (5 g, 19.3 mmol) in dry $Et_2O$ (20 mL) was added dropwise at such a rate that the solution started to reflux. After complete addition, the reaction mixture was stirred for a further 10 min, before saturated aq. $NH_4Cl$ solution (70 mL) was added carefully. The layers were separated, and the aqueous layer was extracted with $Et_2O$ (2×70 mL). The combined organic extracts were dried ($MgSO_4$), filtered and concentrated under reduced pressure to give tert-butyl (S)-4-(2-hydroxypropan-2-yl)-2,2-dimethyloxazolidine-3-carboxylate (4.62 g, 92%) as a colorless oil, which was used directly in the next step without any purification.

$^1$H NMR (400 MHz, Chloroform-d) δ 1.16 (s, 3H), 1.17 (s, 3H), 1.49 (s, 9H), 1.50 (s, 3H), 1.58 (s, 3H), 3.72-3.82 (m, 1H), 3.92-4.02 (m, 2H), 5.25 (s, 1H).

To a solution of tert-butyl (S)-4-(2-hydroxypropan-2-yl)-2,2-dimethyloxazolidine-3-carboxylate (5.12 g, 19.7 mmol) in DMF (19.0 mL), cooled to 0° C., were added NaH (60% dispersion in mineral oil, 1.02 g, 25.6 mmol) and methyl iodide (2.46 mL, 39.5 mmol) and the reaction mixture. was stirred at room temperature for 2 h. MeOH (2.0 mL) was added to quench the reaction, then the mixture was diluted with DCM (50.0 mL) and washed twice with water. The organic layer was dried ($MgSO_4$), filtered and concentrated under reduced pressure. The residue was purified by silica gel chromatography (dry pack) using a gradient of EtOAc (0-100%) in hexanes to provide tert-butyl (S)-4-(2-methoxypropan-2-yl)-2,2-dimethyloxazolidine-3-carboxylate (4.9 g, 91%) as a colorless oil, which crystallized on standing.

$^1$H NMR (400 MHz, Chloroform-d) δ 1.13 (s, 3H), 1.19 (s, 3H), 1.48 (s, 9H), 1.49 (s, 3H), 1.61 (s, 3H), 3.21 (s, 3H), 3.83-3.89 (m, 1H), 3.90-4.11 (m, 1H), 4.12-4.18 (m, 1H).

To a stirred solution of tert-butyl (S)-4-(2-methoxypropan-2-yl)-2,2-dimethyloxazolidine-3-carboxylate (3.60 g, 13.2 mmol) in MeOH (55.0 mL) was added PTSA (250 mg, 1.32 mmol) and the resulting mixture was stirred at room temperature for 30 min. The reaction was quenched with sat. aq. $NaHCO_3$ (10 mL). The solvent was removed under reduced pressure and $H_2O$ (15 mL) was added. The aqueous layer was extracted with EtOAc (3×25 mL) and the combined organic extracts were dried ($Na_2SO_4$), filtered and concentrated under reduced pressure to give tert-butyl (S)-(1-hydroxy-3-methoxy-3-methylbutan-2-yl)carbamate (Intermediate 18) (3.0 g, 98%) as a white solid.

The data for Intermediate 18 are in Table 2.

Route 5

Typical procedure for the preparation of protected amino alcohols, as exemplified by the preparation of Intermediate 20, 2-(trimethylsilyl)ethyl (2-hydroxy-1-(oxetan-3-yl)ethyl)carbamate

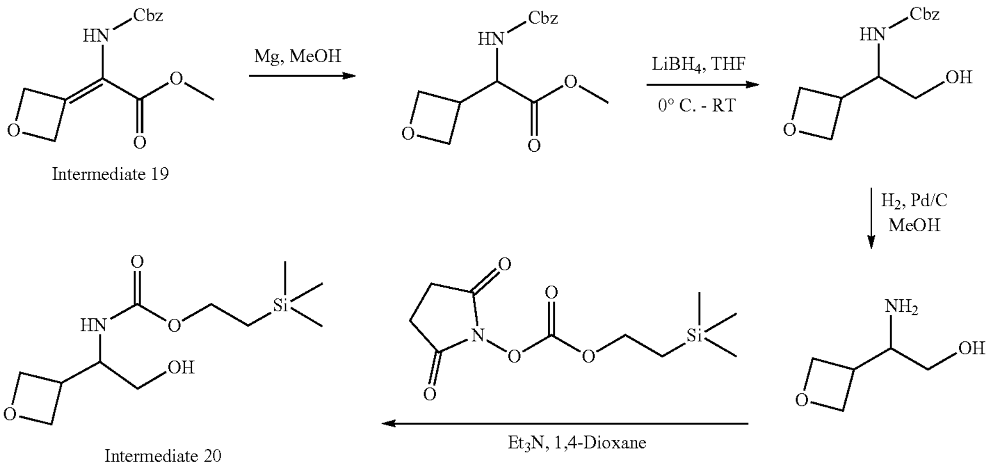

Intermediate 19

Intermediate 20

A 500-mL flask under $N_2$ was charged with methyl 2-(((benzyloxy)carbonyl)amino)-2-(oxetan-3-ylidene)acetate (Intermediate 19) (4.06 g, 14.6 mmol) and MeOH (240 mL). Mg turnings (3.56 g, 146 mmol) were then added, and the mixture was stirred at room temperature for 3 h (Warning: copious evolution of $H_2$ was observed). The resulting mixture was cooled to 0° C and sat. aq. $NH_4Cl$ (85 mL) was slowly and carefully added. The mixture was concentrated under reduced pressure until most of the MeOH had been removed, and the residue was extracted with DCM (3×60 mL). The organic phases were combined, washed with brine (50 mL), dried over $MgSO_4$, and concentrated under reduced pressure. The residue was purified by column chromatography (dry injection, 80 g $SiO_2$, 0:100 to 90:10, EtOAc:hexanes) to afford methyl 2-(((benzyloxy)carbonyl)amino)-2-(oxetan-3-yl)acetate (2.41 g, 59%) as a colorless solid.

$^1$H NMR (400 MHz, DMSO-$d_6$) δ 3.20-3.37 (m, 1H), 3.62 (s, 3H), 4.35 (t, J=6.3 Hz, 1H), 4.38-4.48 (m, 2H), 4.50-4.62 (m, 2H), 5.05 (s, 2H), 7.27-7.41 (m, 5H), 7.86 (d, J=8.0 Hz, 1H).

A 100-mL flask under $N_2$ was charged with methyl 2-(((benzyloxy)carbonyl)amino)-2-(oxetan-3-yl)acetate (2.35 g, 8.41 mmol) and anhydrous THF (35 mL). The resulting solution was cooled to 0° C., then $LiBH_4$ solution in THE (2 M, 8.4 mL, 16.8 mmol) was added dropwise. The resulting mixture was stirred at 0° C. for 30 min, then it was further stirred at room temperature for 2 h. The resulting mixture was cooled to 0° C., carefully quenched by the addition of water (20 mL), and further stirred at room temperature for 30 min. EtOAc (40 mL) was added, the phases were separated, and the aqueous phase was extracted with EtOAc (2×20 mL). The organic phases were combined, dried over $MgSO_4$, and concentrated under reduced pressure to afford benzyl (2-hydroxy-1-(oxetan-3-yl)ethyl)carbamate (1.90 g, 90%) as a colorless solid.

$^1H$ NMR (500 MHz, DMSO-$d_6$) δ 3.04-3.13 (m, 1H), 3.20-3.27 (m, 1H), 3.30-3.36 (m, 1H), 3.78-3.85 (m, 1H), 4.33-4.41 (m, 2H), 4.48-4.57 (m, 2H), 4.65 (t, J=5.6 Hz, 1H), 5.03 (s, 2H), 7.15 (d, J=8.8 Hz, 1H), 7.29-7.33 (m, 1H), 7.33-7.39 (m, 4H).

A 100-mL flask was charged with 10% Pd/C (178 mg, 0.167 mmol Pd) then the flask was purged with $N_2$. A solution of benzyl (2-hydroxy-1-(oxetan-3-yl)ethyl)carbamate (1.68 g, 6.69 mmol) in MeOH (34 mL) was then added. The atmosphere was replaced with $H_2$ by four evacuation/$H_2$ cycles, and the suspension was stirred under $H_2$ (1 atm) at room temperature for 5 h. The atmosphere in the flask was replaced with $N_2$, the suspension was filtered over Celite, and the solid residue was washed several times with MeOH. The filtrate was concentrated under reduced pressure to afford 2-amino-2-(oxetan-3-yl)ethan-1-ol (784 mg, 100%) as a colorless oil.

$^1H$ NMR (400 MHz, Chloroform-d) δ 2.90-3.00 (m, 1H), 3.18-3.29 (m, 2H), 3.50-3.56 (m, 1H), 4.47 (t, J=6.2 Hz, 1H), 4.58 (t, J=6.2 Hz, 1H), 4.73-4.83 (m, 2H). Three exchangeable protons not observed.

A 200-mL flask under $N_2$ was charged with 2-amino-2-(oxetan-3-yl)ethan-1-ol (784 mg, 6.69 mmol) and 1,4-dioxane (57 mL). $Et_3N$ (1.4 mL, 10.0 mmol) was then added, followed by a solution of 2,5-dioxopyrrolidin-1-yl (2-(trimethylsilyl)ethyl) carbonate (CAS: 78269-85-9) (1.77 g, 6.82 mmol) in 1,4-dioxane (10 mL). A thick suspension immediately formed, which was stirred at room temperature for 16 h. The resulting clear solution was concentrated under reduced pressure and the residue was dissolved in a mixture of EtOAc (75 mL) and sat. aq.

$NH_4Cl$ (50 mL). The phases were separated, and the aqueous phase was extracted with EtOAc (2×25 mL). The organic phases were combined, washed with brine (25 mL), dried over $MgSO_4$, and concentrated under reduced pressure. The residue was purified by column chromatography (dry injection, 40 g $SiO_2$, 50:50 to 100:0, EtOAc:hexanes) to afford 2-(trimethylsilyl)ethyl (2-hydroxy-1-(oxetan-3-yl)ethyl)carbamate (Intermediate 20) (1.68 g, 96%) as a colorless oil.

The data for Intermediate 20 are in Table 2.

Route 6

Typical procedure for the preparation of protected amino alcohols, as exemplified by the preparation of Intermediate 26, tert-butyl (2,6-dichloro-5-hydroxypyrimidin-4-yl)((2R,3S)-3-hydroxybutan-2-yl)carbamate

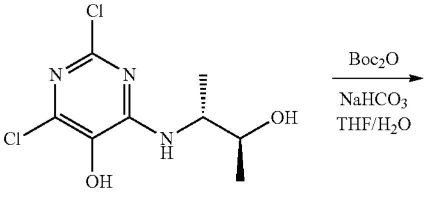

Intermediate 25

-continued

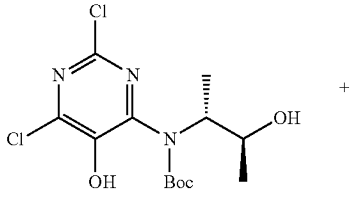

Intermediate 26

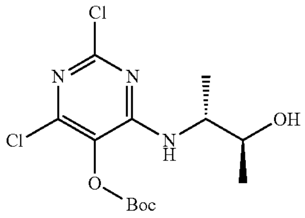

To a solution of 2,4-dichloro-6-(((2R,3S)-3-hydroxybutan-2-yl)amino)pyrimidin-5-ol (Intermediate 25) (1.02 g, 4.05 mmol) in a mixture of THF (40 mL) and water (20 mL) were added di-tert-butyl dicarbonate (927 mg, 4.25 mmol) and $NaHCO_3$ (714 mg, 8.5 mmol) and the reaction mixture was stirred at room temperature for 18 h. The mixture was then concentrated under reduced pressure and the residue was directly purified by silica gel chromatography (dry pack) using a gradient of EtOAc (0-100%) in hexanes then using a gradient of MeOH (0-15%) in DCM to provide tert-butyl (2,6-dichloro-5-hydroxypyrimidin-4-yl)((2R,3S)-3-hydroxybutan-2-yl)carbamate (Intermediate 26) (155 mg, 11%) as a colorless oil and tert-butyl (2,4-dichloro-6-(((2R,3S)-3-hydroxybutan-2-yl)amino)pyrimidin-5-yl) carbonate (350 mg, 25%) as a pale yellow oil. The undesired O-Boc product can be separately converted to the desired N-Boc product by stirring with $NaHCO_3$ in THF/H2O.

The data for Intermediate 26 are in Table 2.

Route 7

Typical procedure for the preparation of protected amino alcohols, as exemplified by the preparation of Intermediate 36, tert-butyl (1,1,1-trifluoro-3-hydroxypropan-2-yl)carbamate

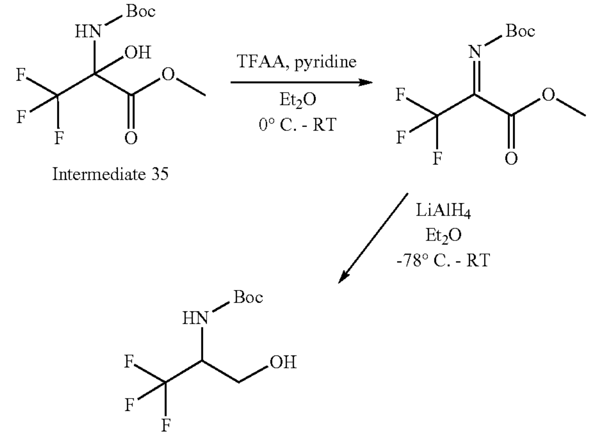

Intermediate 35

Intermediate 36

A 100-mL flask under $N_2$ was charged with methyl 2-((tert-butoxycarbonyl)amino)-3,3,3-trifluoro-2-hydroxypropanoate (Intermediate 35) (2.71 g, 9.92 mmol) and anhydrous $Et_2O$ (50 mL). The resulting mixture was cooled to 0° C., then TFAA (1.40 mL, 9.92 mmol) and pyridine (1.60 mL, 19.8 mmol) were added. The mixture was stirred for 1 h at 0° C., and it was stirred for a further 16 h at room temperature. The resulting suspension was filtered, and the solids were washed with $Et_2O$ (2×25 mL). The filtrate was washed with water (25 mL), dried over $MgSO_4$, and concentrated under reduced pressure to give the crude methyl 2-((tert-butoxycarbonyl)imino)-3,3,3-trifluoropropanoate (2.51 g, 99%) as a clear oil that was used in the next step without further purification.

$^1H$ NMR (500 MHz, Chloroform-d) δ 1.58 (s, 9H), 3.95 (s, 3H).

An oven-dried 100-mL flask under $N_2$ was charged with methyl 2-((tert-butoxycarbonyl)imino)-3,3,3-trifluoropropanoate (2.51 g, 9.84 mmol) and anhydrous $Et_2O$ (30 mL). The resulting solution was cooled to −78° C., then $LiAlH_4$ solution in THF (2 M, 9.84 mL, 19.7 mmol) was slowly added. The mixture was then stirred for 16 h while being slowly warmed to room temperature. The resulting solution was cooled to 0° C., and carefully quenched by the successive addition of water (0.75 mL), aq. NaOH (3.8 M, 0.75 mL) and water (2.3 mL). The resulting suspension was warmed to room temperature, and $MgSO_4$ was added. The suspension was filtered, and the solids were washed with THF (4×20 mL). The filtrate was concentrated under reduced pressure, and the residue was purified by column chromatography (dry injection, 40 g $SiO_2$, 5:95 to 70:30, EtOAc:hexanes) to give tert-butyl (1,1,1-trifluoro-3-hydroxypropan-2-yl)carbamate (Intermediate 36) (1.38 g, 61%) as a colorless solid.

The data for Intermediate 36 are in Table 2.

Route 8

Typical procedure for the preparation of protected amino acids, as exemplified by the preparation of Intermediate 61, 2-(((tert-butoxycarbonyl)amino)methyl)butanoic acid

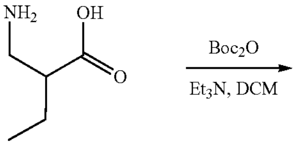

Intermediate 60

-continued

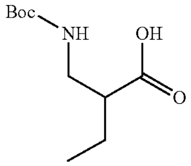

Intermediate 61

2-(Aminomethyl)butanoic acid (Intermediate 60) (1.5 g, 9.8 mmol) was dissolved in DCM (5.0 mL), and TEA (379 mg, 14.7 mmol) was added dropwise at 0° C. Di-tert-butyl dicarbonate (512 mg, 11.7 mmol) was then added and the reaction mixture was stirred at RT for 1 h. The solvent was removed in-vacuo and the residue was partitioned between $H_2O$ (100 mL) and DCM (60 mL). The aqueous layer was washed with 1 M citric acid solution and then further extracted with DCM (2×60 mL). All the organic layers were combined, dried ($Na_2SO_4$) and the solvent was removed in-vacuo to give the crude product, which was purified by column chromatography on silica using 16% EtOAc in hexane to give 2-(((tert-butoxycarbonyl)amino)methyl)butanoic acid (Intermediate 61) (2.4 g, 86%) as a colorless gum.

The data for Intermediate 61 are in Table 2.

General Synthetic Procedures:

Route A

Typical procedure for the preparation of fused pyrimidines, as exemplified by the preparation of Example 1-1, (R)-4-(3-(methylamino)pyrrolidin-1-yl)-7,8-dihydro-6H-pyrimido[5,4-b][1,4]oxazin-2-amine

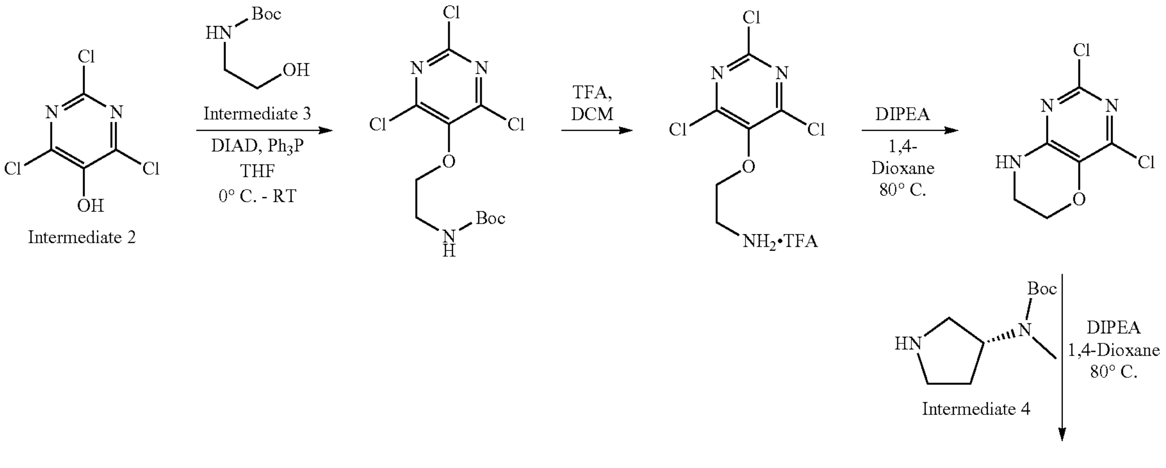

-continued

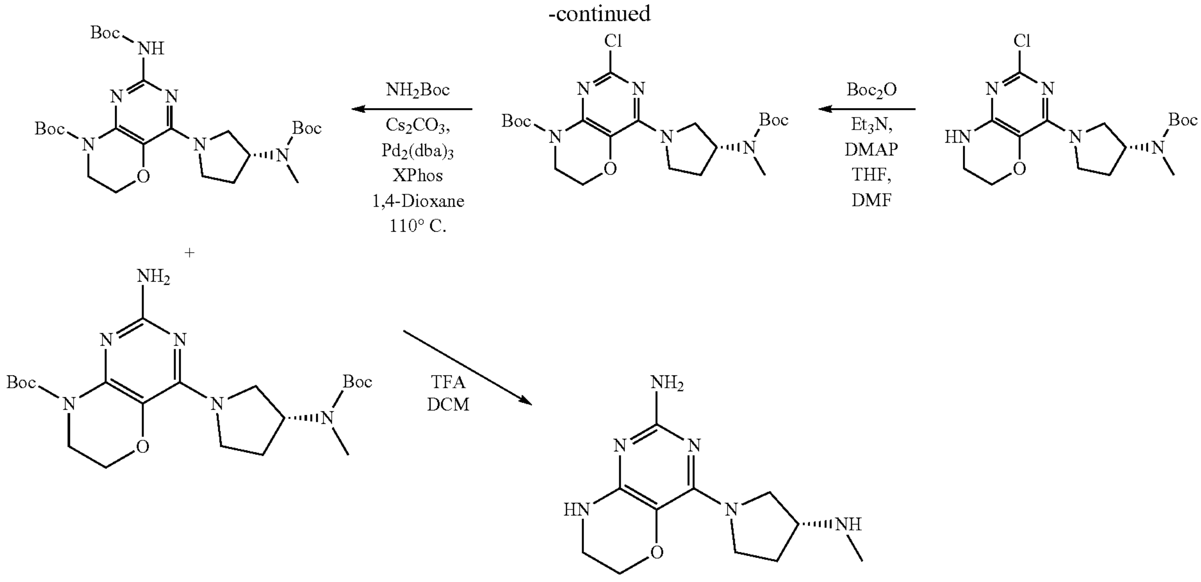

Example 1-1

To a solution of 2,4,6-trichloropyrimidin-5-ol (Intermediate 2) (384 mg, 1.926 mmol) and tert-butyl (2-hydroxyethyl)carbamate (Intermediate 3) 621 mg, 3.851 mmol) in THF (11.0 mL), cooled to 0° C., were added DIAD (0.57 mL, 2.888 mmol) and $PPh_3$ (758 mg, 2.888 mmol) and the reaction mixture was stirred for 2 h. The THF was then removed under reduced pressure and silica was added. The residue was purified by silica gel chromatography (dry pack) using a gradient of EtOAc (0-60%) in hexanes to provide tert-butyl (2-((2,4,6-trichloropyrimidin-5-yl)oxy)ethyl)carbamate (633 mg, 96%) as a white solid.

$^1$H NMR (500 MHz, Chloroform-d) δ 1.45 (s, 9H), 3.56 (q, J=5.5 Hz, 2H), 4.17 (t, J=5.0 Hz, 2H), 5.05 (s, 1H).

To a solution of tert-butyl (2-((2,4,6-trichloropyrimidin-5-yl)oxy)ethyl)carbamate (633 mg, 1.848 mmol) in DCM (5.10 mL) was added TFA (5.10 mL) and the reaction mixture was stirred at room temperature for 10 min. The mixture was then concentrated in-vacuo to dryness to give 2-((2,4,6-trichloropyrimidin-5-yl)oxy)ethan-1-amine trifluoroacetic acid salt (675 mg, >100%) as a colourless oil which was used directly in the next step without any purification.

LCMS (System 1, Method D): m/z 242/244 $(M+H)^+$ $(ES^+)$, at 0.54 min, 190-320 nm.

To a solution of 2-((2,4,6-trichloropyrimidin-5-yl)oxy)ethan-1-amine trifluoroacetic acid salt (659 mg, 1.848 mmol) in 1,4-dioxane (5.00 mL) was added DIPEA (0.97 mL, 5.545 mmol) and the reaction mixture was heated at 80° C. for 18 h. The mixture was then diluted with water and extracted with EtOAc (3×10.0 mL). The combined organic extracts were dried ($MgSO_4$), filtered and concentrated under reduced pressure. The residue was purified by silica gel chromatography (dry pack) using a gradient of EtOAc (0-100%) in hexanes to provide 2,4-dichloro-7,8-dihydro-6H-pyrimido[5,4-b][1,4]oxazine (279 mg, 73%) as a white solid.

LCMS (System 1, Method D): m/z 206/208 $(M+H)^+$ $(ES^+)$, at 1.87 min, 190-320 nm.

To a solution of 2,4-dichloro-7,8-dihydro-6H-pyrimido[5,4-b][1,4]oxazine (279 mg, 1.354 mmol) in 1,4-dioxane (2.90 mL) were added tert-butyl (R)-methyl(pyrrolidin-3-yl)carbamate (Intermediate 4) (271 mg, 1.354 mmol) and DIPEA (0.47 mL, 2.708 mmol) and the mixture was heated at 80° C. for 18 h. After cooling to room temperature, the mixture was diluted with water and extracted with EtOAc (3×10.0 mL). The combined organic extracts were dried ($MgSO_4$), filtered and concentrated under reduced pressure. The residue was purified by silica gel chromatography using a gradient of EtOAc (0-100%) in hexanes to provide tert-butyl (R)-(1-(2-chloro-7,8-dihydro-6H-pyrimido[5,4-b][1,4]oxazin-4-yl)pyrrolidin-3-yl)(methyl)carbamate (218 mg, 44%) as a white solid.

LCMS (System 1, Method D): m/z 370/372 $(M+H)^+$ $(ES^+)$, at 2.40 min, 190-320 nm.

To a solution of tert-butyl (R)-(1-(2-chloro-7,8-dihydro-6H-pyrimido[5,4-b][1,4]oxazin-4-yl)pyrrolidin-3-yl)(methyl)carbamate (127 mg, 0.343 mmol) in a mixture of THF (0.83 mL) and DMF (0.22 mL) were added di-tert-butyl dicarbonate (112 mg, 0.515 mmol), $Et_3N$ (0.102 mL, 0.755 mmol) and DMAP (21 mg, 0.172 mmol) and the reaction mixture was stirred at room temperature for 18 h. The mixture was then concentrated under reduced pressure, and the residue was diluted with DCM and silica was added. The residue was purified by silica gel chromatography (dry pack) using a gradient of EtOAc (0-40%) in hexanes to provide tert-butyl (R)-4-(3-((tert-butoxycarbonyl)(methyl)amino)pyrrolidin-1-yl)-2-chloro-6,7-dihydro-8H-pyrimido[5,4-b][1,4]oxazine-8-carboxylate (113 mg, 70%) as a colorless oil.

LCMS (System 1, Method D): m/z 470/472 $(M+H)^+$ $(ES^+)$, at 2.75 min, 190-320 nm.

To a degassed solution of tert-butyl (R)-4-(3-((tert-butoxycarbonyl)(methyl)amino)pyrrolidin-1-yl)-2-chloro-6,7-dihydro-8H-pyrimido[5,4-b][1,4]oxazine-8-carboxylate (114 mg, 0.243 mmol) and tert-butyl carbamate (28 mg, 0.243 mmol) in 1,4-dioxane (2.40 mL) were added $Cs_2CO_3$ (198 mg, 0.606 mmol), tris(dibenzylideneacetone)dipalladium(0) (CAS: 51364-51-3) (22.2 mg, 0.024 mmol) and XPhos (CAS: 564483-18-7) (23.1 mg, 0.049 mmol) and the reaction mixture was heated at 110° C. for 18 h. After cooling to room temperature, the mixture was filtered through a pad of Celite, washing the residue with EtOAc.

The filtrate was concentrated under reduced pressure and the residue was purified by silica gel chromatography using a gradient of EtOAc (0-100%) in hexanes then a gradient of MeOH (0-30%) in DCM to provide tert-butyl (R)-4-(3-((tert-butoxycarbonyl)(methyl)amino)pyrrolidin-1-yl)-2-((tert-butoxycarbonyl)amino)-6,7-dihydro-8H-pyrimido[5,4-b][1,4]oxazine-8-carboxylate (62 mg, 46%) as a pale yellow oil and tert-butyl (R)-2-amino-4-(3-((tert-butoxycarbonyl)(methyl)amino)pyrrolidin-1-yl)-6,7-dihydro-8H-pyrimido[5,4-b][1,4]oxazine-8-carboxylate (54 mg, 49%) as a yellow oil. 50 LCMS (System 1, Method D): m/z 551 $(M+H)^+$ $(ES^+)$, at 2.11 min, 190-320 nm.

LCMS (System 1, Method D): m/z 451 $(M+H)^+$ $(ES^+)$, at 1.96 min, 190-320 nm.

(0.8 mL) and the reaction mixture was stirred at room temperature for 2 h. The mixture was then concentrated to dryness and the residue purified using purification method A to provide (R)-4-(3-(methylamino)pyrrolidin-1-yl)-7,8-dihydro-6H-pyrimido[5,4-b][1,4]oxazin-2-amine, Example 1-1 (42 mg, 73%) as a white solid.

The data for Example 1-1 are in Table 3.

Route B

Typical procedure for the preparation of fused pyrimidines as exemplified by the preparation of Example 1-3, (R)-7-ethyl-4-((R)-3-(methylamino)pyrrolidin-1-yl)-7,8-dihydro-6H-pyrimido[5,4-b][1,4]oxazin-2-amine dihydrochloride salt

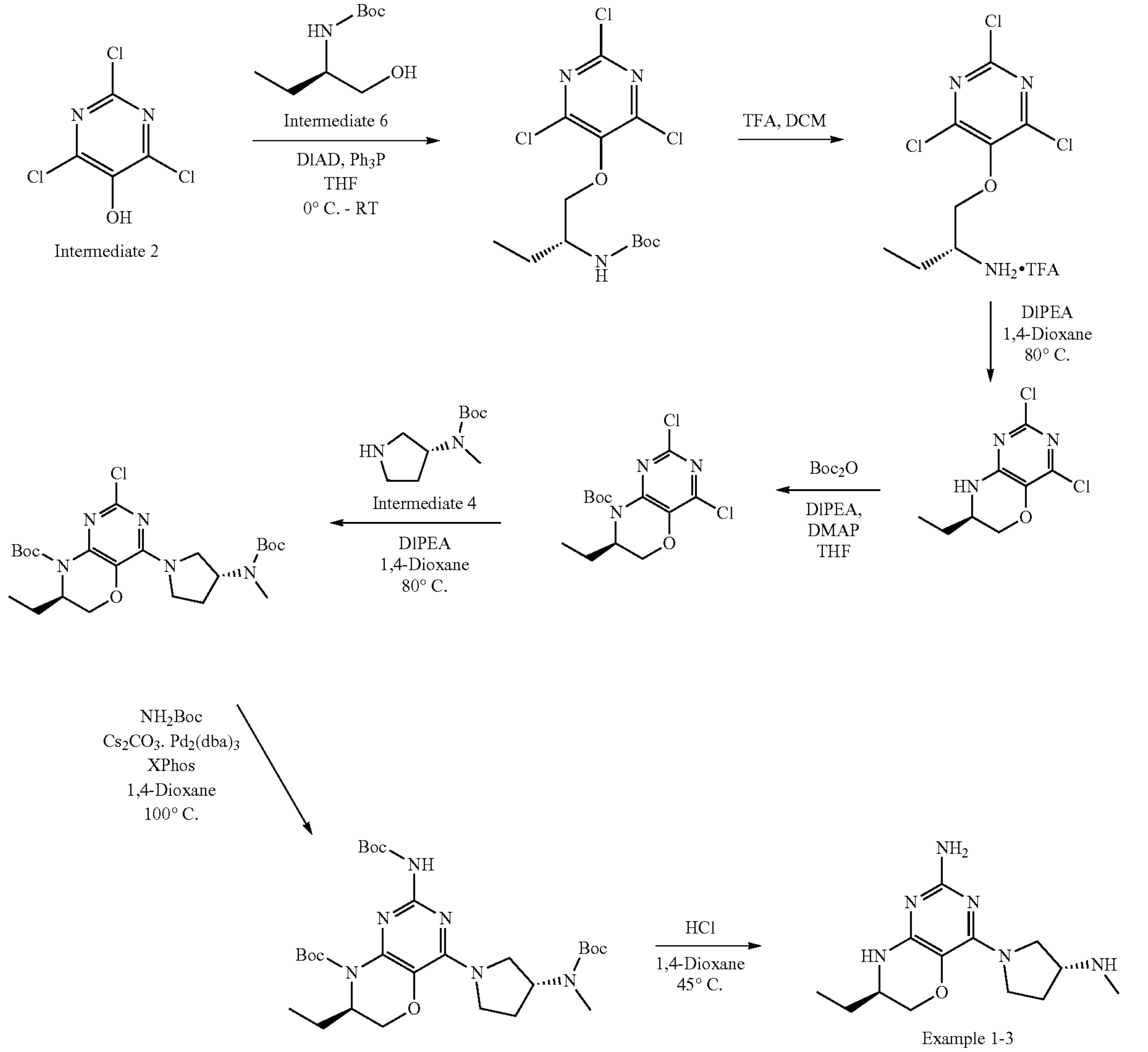

To a solution of tert-butyl (R)-4-(3-((tert-butoxycarbonyl)(methyl)amino)pyrrolidin-1-yl)-2-((tert-butoxycarbonyl)amino)-6,7-dihydro-8H-pyrimido[5,4-b][1,4]oxazine-8-carboxylate (62 mg, 0.113 mmol) and tert-butyl (R)-2-amino-4-(3-((tert-butoxycarbonyl)(methyl)amino)pyrrolidin-1-yl)-6,7-dihydro-8H-pyrimido[5,4-b][1,4]oxazine-8-carboxylate (54 mg, 0.120 mmol) in DCM (1.10 mL) was added TFA Example 1.3

A 100-mL flask under $N_2$ was charged with tert-butyl (R)-(1-hydroxybutan-2-yl)carbamate (Intermediate 6) (2.55 g, 13.5 mmol), 2,4,6-trichloropyrimidin-5-ol (Intermediate 2) (1.50 g, 7.50 mmol) and anhydrous THF (30 mL). The resulting solution was cooled to 0° C., then $Ph_3P$ (3.15 g, 12.0 mmol) was added. Once the $Ph_3P$ had completely dissolved, DIAD (2.36 mL, 12.0 mmol) was then added dropwise over ca. 5 min. The reaction mixture was stirred at 0° C. for 10 min, then it was warmed to room temperature, and stirred for a further 16 h. The mixture was concentrated to dryness, and the residue was purified by column chromatography (dry injection, 80 g $SiO_2$, 0:100 to 50:50, EtOAc:hexanes) to afford tert-butyl (R)-(1-((2,4,6-trichloropyrimidin-5-yl)oxy)butan-2-yl)carbamate (1.78 g, 64%) as a colorless solid.

$^1H$ NMR (500 MHz, DMSO-$d_6$) δ 0.89 (t, J=7.4 Hz, 3H), 1.38 (s, 9H), 1.40-1.51 (m, 1H), 1.59-1.69 (m, 1H), 3.61-3.70 (m, 1H), 3.97-4.11 (m, 2H), 6.86 (d, J=8.4 Hz, 1H).

A 100-mL flask was charged with tert-butyl (R)-(1-((2,4,6-trichloropyrimidin-5-yl)oxy)butan-2-yl)carbamate (1.78 g, 4.80 mmol) and DCM (20 mL). TFA (10.0 mL, 135 mmol) was then added and the resulting solution was stirred at room temperature for 10 min. The mixture was co-evaporated with toluene under reduced pressure to afford crude (R)-1-((2,4,6-trichloropyrimidin-5-yl)oxy)butan-2-amine trifluoroacetic acid salt as a colorless oil. The product was used in the next step without further purification.

LCMS (System 1, Method E): m/z 234/236 $(M-Cl)^+$ $(ES^+)$, at 2.05 min, 190-320 nm.

A 20-mL sealable tube under $N_2$ was charged with crude (R)-1-((2,4,6-trichloropyrimidin-5-yl)oxy)butan-2-amine trifluoroacetic acid salt (ca. 4.80 mmol) and 1,4-dioxane (13.5 mL). DIPEA (2.5 mL, 14.4 mmol) was then added, the tube was sealed, and the resulting solution was stirred at 80° C. for 16 h. The mixture was cooled to room temperature and was concentrated under reduced pressure. The residue was purified by column chromatography (dry injection, 40 g $SiO_2$, 0:100 to 80:20, EtOAc:hexanes) to afford (R)-2,4-dichloro-7-ethyl-7,8-dihydro-6H-pyrimido[5,4-b][1,4]oxazine (1.01 g, 90% over 2 steps) as a colorless oil.

LCMS (System 1, Method D): m/z 234/236 $(M+H)^+$ $(ES^+)$, at 2.18 min, 190-320 nm.

A 50-mL flask was charged with (R)-2,4-dichloro-7-ethyl-7,8-dihydro-6H-pyrimido[5,4-b][1,4]oxazine (1.01 g, 4.31 mmol) and THE (21.5 mL). DIPEA (1.5 mL, 8.6 mmol) was then added, followed by di-tert-butyl dicarbonate (1.70 g, 7.77 mmol) and DMAP (53 mg, 0.43 mmol). The resulting solution was stirred at room temperature for 16 h. The mixture was evaporated under reduced pressure, and the residue was purified by column chromatography (dry injection, 40 g $SiO_2$, 0:100 to 30:70, EtOAc:hexanes) to afford tert-butyl (R)-2,4-dichloro-7-ethyl-6,7-dihydro-8H-pyrimido[5,4-b][1,4]oxazine-8-carboxylate (1.36 g, 94%) as a colorless solid.

LCMS (System 1, Method D): m/z 278/280 $(M-56+H)^+$ $(ES^+)$, at 2.68 min, 190-320 nm.

A 20-mL sealable tube under $N_2$ was charged with tert-butyl (R)-2,4-dichloro-7-ethyl-6,7-dihydro-8H-pyrimido[5,4-b][1,4]oxazine-8-carboxylate (680 mg, 2.03 mmol), tert-butyl (R)-methyl(pyrrolidin-3-yl)carbamate (Intermediate 4) (448 mg, 2.24 mmol) and anhydrous 1,4-dioxane (5.8 mL). DIPEA (0.71 mL, 4.1 mmol) was added, the tube was then sealed, and the mixture was stirred at 80° C. for 16 h. The resulting mixture was cooled to room temperature, then it was diluted with DCM (30 mL) to dissolved the solids that had precipitated. The resulting solution was concentrated under reduced pressure over silica gel, and the residue was purified by column chromatography (dry injection, 40 g $SiO_2$, 0:100 to 50:50, EtOAc:hexanes) to afford tert-butyl (R)-4-((R)-3-((tert-butoxycarbonyl)(methyl)amino)pyrrolidin-1-yl)-2-chloro-7-ethyl-6,7-dihydro-8H-pyrimido[5,4-b][1,4]oxazine-8-carboxylate (878 mg, 87%) as a colorless solid.

LCMS (System 1, Method D): m/z 442/444 $(M-56+H)^+$ $(ES^+)$, at 2.90 min, 190-320 nm.

A 20-mL sealable tube under $N_2$ was charged with tert-butyl carbamate (310 mg, 2.64 mmol), $Cs_2CO_3$ (1.15 g, 3.53 mmol), tris(dibenzylideneacetone)dipalladium(0) (CAS: 51364-51-3) (80.7 mg, 0.0882 mmol) and XPhos (CAS: 564483-18-7) (168 mg, 0.353 mmol). A solution of tert-butyl (R)-4-((R)-3-((tert-butoxycarbonyl)(methyl)amino)pyrrolidin-1-yl)-2-chloro-7-ethyl-6,7-dihydro-8H-pyrimido[5,4-b][1,4]oxazine-8-carboxylate (878 mg, 1.76 mmol) in 1,4-dioxane (14 mL) was then added, and the resulting suspension was sparged with $N_2$ for 15 min. The tube was then sealed, and the mixture was stirred at 100° C. for 3 h. The mixture was concentrated under reduced pressure over silica gel, and the residue was purified by column chromatography (dry injection, 40 g $SiO_2$, 0:100 to 60:10, EtOAc:hexanes) to afford the still impure product as a yellow solid. The product was further purified by reversed-phase column chromatography (MeOH injection, 60 g C-18, 10:90 to 95:5, MeCN:10 mM ammonium bicarbonate in water, pH 10) to afford tert-butyl (R)-4-((R)-3-((tert-butoxycarbonyl)(methyl)amino)pyrrolidin-1-yl)-2-((tert-butoxycarbonyl)amino)-7-ethyl-6,7-50 dihydro-8H-pyrimido[5,4-b][1,4]oxazine-8-carboxylate (630 mg, 62%) as a colorless solid after lyophilization.

LCMS (System 1, Method D): m/z 579 $(M+H)^+$ $(ES^+)$, at 2.20 min, 190-320 nm.

A 50-mL flask under $N_2$ was charged with tert-butyl (R)-4-((R)-3-((tert-butoxycarbonyl)(methyl)amino)pyrrolidin-1-yl)-2-((tert-butoxycarbonyl)amino)-7-ethyl-6,7-dihydro-8H-pyrimido[5,4-b][1,4]oxazine-8-carboxylate (630 mg, 1.09 mmol) and 1,4-dioxane (5.5 mL). Once the solids had dissolved, HCl solutionin 1,4-dioxane (4 M, 5.5 mL, 22 mmol) was added, and the resulting mixture was stirred vigorously at 45° C. for 3 h. The resulting suspension was concentrated under reduced pressure, the residue was dissolved in water (10 mL) and lyophilized to dryness. The resulting yellow solid was purified by reversed-phase column chromatography ($H_2O$ injection, 60 g C-18, isocratic 5:95, MeCN:$H_2O$) to afford (R)-7-ethyl-4-((R)-3-(methylamino)pyrrolidin-1-yl)-7,8-dihydro-6H-pyrimido[5,4-b][1,4]oxazin-2-amine dihydrochloride salt, Example 1-3 (324 mg, 77%) as a colorless solid after lyophilization.

The data for Example 1-3 are in Table 3.

Route C

Typical procedure for the preparation of fused pyrimidines as exemplified by the preparation of Example 1-8, 4-((R)-3-(methylamino)pyrrolidin-1-yl)-7-(trifluoromethyl)-7,8-dihydro-6H-pyrimido[5,4-b][1,4]oxazin-2-amine

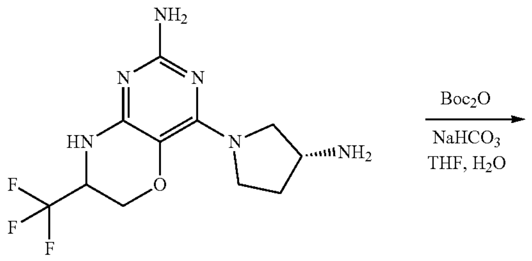

Example 2-3

-continued

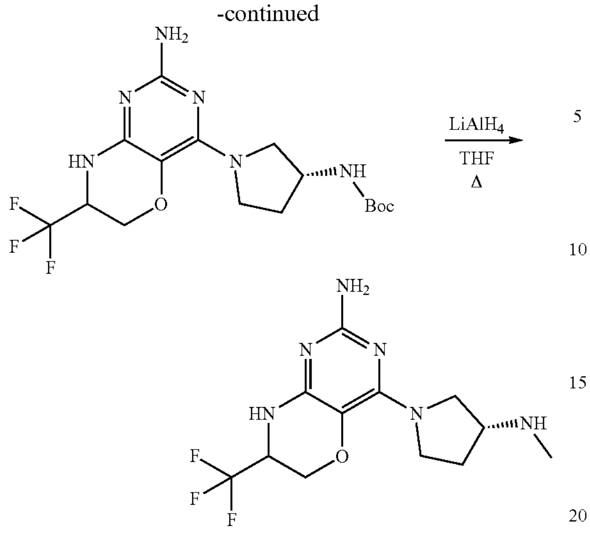

Example 1-8

In a 5-mL flask was charged 4-((R)-3-aminopyrrolidin-1-yl)-7-(trifluoromethyl)-7,8-dihydro-6H-pyrimido[5,4-b][1,4]oxazin-2-amine (Example 2-3) (20 mg, 0.0657 mmol). A solution of di-tert-butyl dicarbonate (15.1 mg, 0.0690 mmol) in THE (0.66 mL) was then added, followed by a solution of $NaHCO_3$ (11.6 mg) in water (0.33 mL). The resulting mixture was stirred at room temperature for 60 h. The mixture was diluted in EtOAc (10 mL) and brine (5 mL), the phases were separated, and the aqueous phase was extracted with EtOAc (2×5 mL). The organic phases were combined, dried over $Na_2SO_4$, and concentrated to dryness to give tert-butyl ((3R)-1-(2-amino-7-(trifluoromethyl)-7,8-dihydro-6H-pyrimido[5,4-b][1,4]oxazin-4-yl)pyrrolidin-3-yl) carbamate (17.0 mg, 64%) as a colorless solid. This product was used in the next step without further purification.

LCMS (System 1, Method D): m/z 405 $(M+H)^+$ $(ES^+)$, at 1.79 min, 190-320 nm.

A 10-mL flask under $N_2$ was charged with tert-butyl ((3R)-1-(2-amino-7-(trifluoromethyl)-7,8-dihydro-6H-pyrimido[5,4-b][1,4]oxazin-4-yl)pyrrolidin-3-yl)carbamate (27.0 mg, 0.0668 mmol) and anhydrous THE (3.3 mL). The solution was cooled to 0° C., then $LiAlH_4$ solution in THE (2 M, 0.17 mL, 0.34 mmol) was added dropwise. The resulting mixture was heated at reflux for 5 h, then it was cooled to 0° C., and carefully quenched by the addition of $Na_2SO_4 \cdot 10H_2O$ (danger: exotherm and H2 evolution). The resulting suspension was filtered, and the collected solid was washed several times with MeOH. The filtrate was filtered through a 0.45 μm filter and concentrated under reduced pressure. The residue was purified using purification method B to afford 4-((R)-3-(methylamino)pyrrolidin-1-yl)-7-(trifluoromethyl)-7,8-dihydro-6H-pyrimido[5,4-b][1,4]oxazin-2-amine, Example 1-8 (14.0 mg, 66%) as a colorless solid.

The data for Example 1-8 are in Table 3.

Route D

Typical procedure for the preparation of fused pyrimidines as exemplified by the preparation of Example 1-13, 4-((R)-3-(methylamino)pyrrolidin-1-yl)-7-(oxetan-3-yl)-7,8-dihydro-6H-pyrimido[5,4-b][1,4]oxazin-2-amine

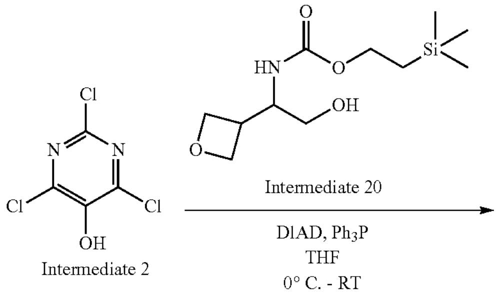

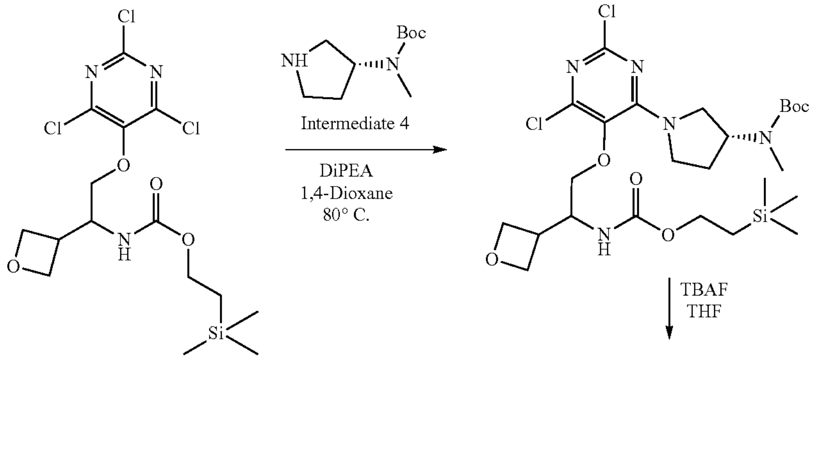

-continued

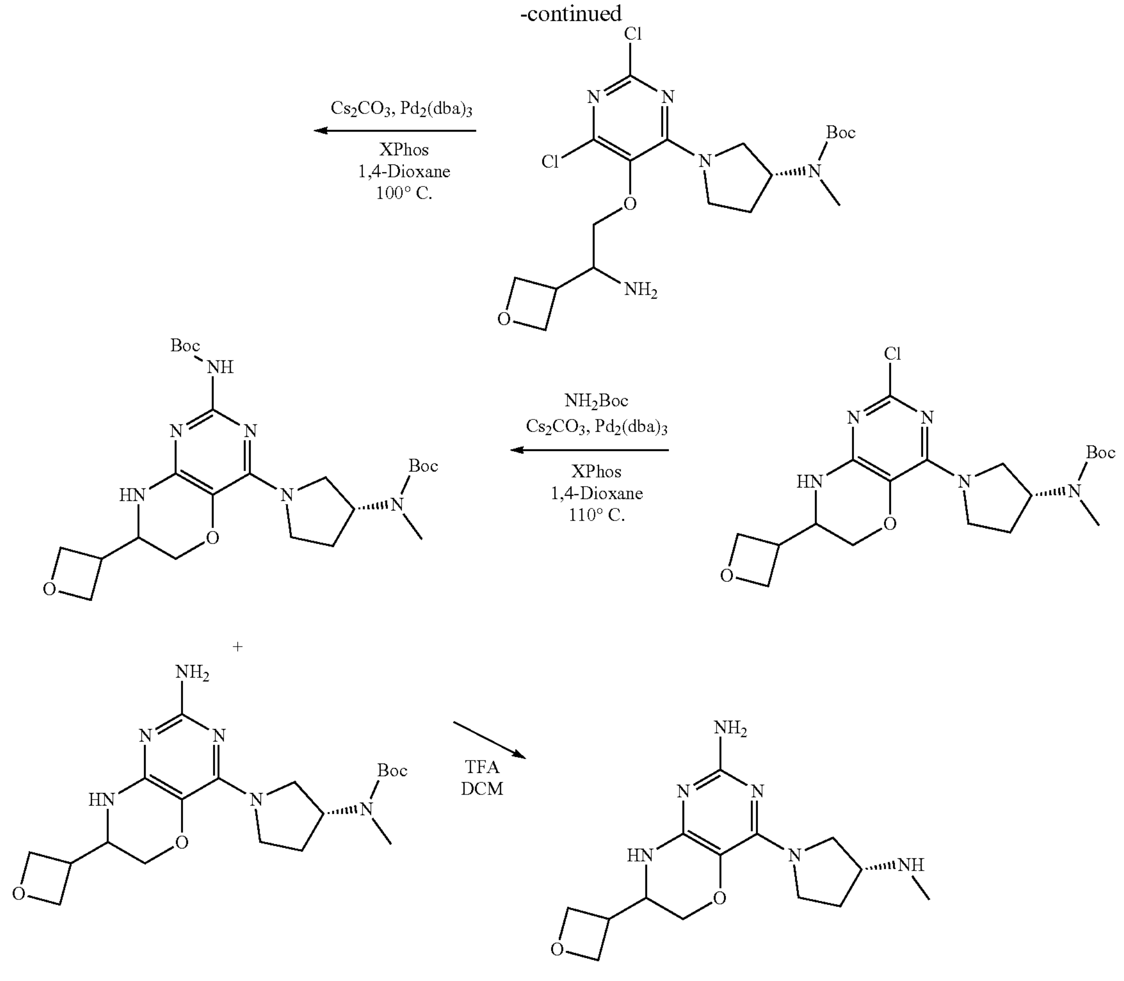

Example 1-13

A 50-mL flask under $N_2$ was charged with 2-(trimethylsilyl)ethyl (2-hydroxy-1-(oxetan-3-yl)ethyl)carbamate (Intermediate 20) (1.05 g, 4.01 mmol), 2,4,6-trichloropyrimidin-5-ol (Intermediate 2) (0.500 g, 2.51 mmol) and anhydrous THF (12.5 mL). The resulting solution was cooled to 0° C., then PhaP (986 mg, 3.76 mmol) was added. Once the $Ph_3P$ had completely dissolved, DIAD (0.740 mL, 3.76 mmol) was then added dropwise over ca. 5 min. The reaction mixture was then stirred at 0° C. for 10 min, then it was warmed to room temperature, and stirred for a further 16 h. The mixture was concentrated to dryness, and the residue was purified by column chromatography (dry injection, 40 g $SiO_2$, 0:100 to 80:20, EtOAc:hexanes) to afford the crude product, which was further purified by reversed-phase column chromatography (DMSO injection, 12 g C-18, 5:95 to 95:5, MeCN:0.1% formic acid in water) to give 2-(trimethylsilyl)ethyl (1-(oxetan-3-yl)-2-((2,4,6-trichloropyrimidin-5-yl)oxy)ethyl)carbamate (847 mg, 63%).

LCMS (System 1, Method D): m/z 414/416 $(M-CO+H)^+$ $(ES^+)$, at 2.20 min, 190-320 nm.

A 20-mL sealable tube under $N_2$ was charged with 2-(trimethylsilyl)ethyl (1-(oxetan-3-yl)-2-((2,4,6-trichloropyrimidin-5-yl)oxy)ethyl)carbamate (690 mg, 1.28 mmol), tert-butyl (R)-methyl(pyrrolidin-3-yl)carbamate (Intermediate 4) (256 mg, 1.28 mmol) and anhydrous 1,4-dioxane (6.4 mL). DIPEA (0.45 mL, 2.58 mmol) was then added, the tube was sealed, and the mixture was stirred at 80° C. for 18 h. The resulting solution was concentrated to dryness, and the residue was purified by column chromatography (dry injection, 40 g $SiO_2$, 0:100 to 90:10, EtOAc:hexanes) to afford tert-butyl ((3R)-1-(2,6-dichloro-5-(2-(oxetan-3-yl)-2-(((2-(trimethylsilyl)ethoxy)carboriyl)amino)ethoxy)pyrimidin-4-yl)pyrrolidin-3-yl)(methyl)carbamate (730 mg, 94%) as a colorless solid.

LCMS (System 1, Method D): m/z 578/580 $(M-CO+H)^+$ $(ES^+)$, at 2.32 min, 190-320 nm.

A 10-mL flask under $N_2$ was charged with tert-butyl ((3R)-1-(2,6-dichloro-5-(2-(oxetan-3-yl)-2-(((2-(trimethylsilyl)ethoxy)carbonyl)amino)ethoxy)pyrimidin-4-yl)pyrrolidin-3-yl)(methyl)carbamate (210 mg, 0.346 mmol) and anhydrous THE (3.5 mL). TBAF solution in THE (1 M, 0.865 mL, 0.865 mmol) was then added, and the resulting yellow solution was stirred at room temperature for 16 h. The reaction was quenched by the addition of sat. aq. $NH_4Cl$ (1 mL) and water (1 mL). The resulting mixture was extracted with EtOAc (3x15 mL) and the combined organic phases were dried over $MgSO_4$ and concentrated to dryness. The residue was purified by column chromatography (dry injection, 12 g $SiO_2$, 0:100 to 10:90, MeOH:DCM) to afford the crude product, which was combined with product from a similar reaction conducted at ca. twice the scale and purified by reversed-phase column chromatography (MeOH injection, 12 g C-18, 5:95 to 70:30, MeCN:10 mM ammonium bicarbonate in water, pH 10) to afford tert-butyl ((3R)-1-(5-(2-amino-2-(oxetan-3-yl)ethoxy)-2,6-dichloropyrimidin-4-yl)pyrrolidin-3-yl)(methyl)carbamate (142 mg, 26%) as a colorless solid.

LCMS (System 1, Method E): m/z 326/328 (M-Cl-BOC+H)$^+$ (ES$^+$), at 1.97 min, 190-320 nm.

A 5-mL sealable tube under $N_2$ was charged with tert-butyl ((3R)-1-(5-(2-amino-2-(oxetan-3-yl)ethoxy)-2,6-dichloropyrimidin-4-yl)pyrrolidin-3-yl)(methyl)carbamate (142 mg, 0.307 mmol), $Cs_2CO_3$ (200 mg, 0.614 mmol), tris(dibenzylideneacetone)dipalladium(0) (CAS: 51364-51-3) (14.1 mg, 0.0154 mmol) and XPhos (CAS: 564483-18-7) (29.3 mg, 0.0614 mmol). 1,4-Dioxane (3.0 mL) was then added, and the resulting suspension was sparged with $N_2$ for 15 min. The tube was then sealed, and the mixture was stirred at 100° C. for 3 h. The mixture was concentrated under reduced pressure over silica gel, and the residue was purified by column chromatography (dry injection, 40 g $SiO_2$, 0:100 to 90:10, EtOAc:hexanes) to give tert-butyl ((3R)-1-(2-chloro-7-(oxetan-3-yl)-7,8-dihydro-6H-pyrimido[5,4-b][1,4]oxazin-4-yl)pyrrolidin-3-yl)(methyl)carbamate (70 mg, 54%) as a colorless solid.

LCMS (System 1, Method D): m/z 426/428 (M+H)$^+$ (ES$^+$), at 2.00 min, 190-320 nm.

A 5-mL sealable tube under $N_2$ was charged with tert-butyl carbamate (28.9 mg, 0.247 mmol), $Cs_2CO_3$ (107 mg, 0.329 mmol), tris(dibenzylideneacetone)dipalladium(0) (CAS: 51364-51-3) (15.1 mg, 0.0164 mmol) and XPhos (CAS: 564483-18-7) (31.3 mg, 0.0657 mmol). A solution of tert-butyl ((3R)-1-(2-chloro-7-(oxetan-3-yl)-7,8-dihydro-6H-pyrimido[5,4-b][1,4]oxazin-4-yl)pyrrolidin-3-yl)(methyl)carbamate (70.0 mg, 0.164 mmol) in 1,4-dioxane (1.6 mL) was then added, and the resulting suspension was sparged with $N_2$ for 15 min. The tube was then sealed, and the mixture was stirred at 110° C. for 11 h. The mixture was concentrated under reduced pressure over silica gel, and the residue was purified by reversed-phase column chromatography (DMSO injection, 30 g C-18, 5:95 to 90:10, MeCN:10 mM ammonium bicarbonate in water, pH 10) to give tert-butyl ((3R)-1-(2-((tert-butoxycarbonyl)amino)-7-(oxetan-3-yl)-7,8-dihydro-6H-pyrimido[5,4-b][1,4]oxazin-4-yl)pyrrolidin-3-yl)(methyl)carbamate (15 mg, 18%) as a colorless solid and tert-butyl ((3R)-1-(2-amino-7-(oxetan-3-yl)-7,8-dihydro-6H-pyrimido[5,4-b][1,4]oxazin-4-yl)pyrrolidin-3-yl)(methyl)carbamate (15 mg, 22%) as a colorless solid.

LCMS (System 1, Method D): m/z 507 (M+H)$^+$ (ES$^+$), at 2.06 min, 190-320 nm.

LCMS (System 1, Method D): m/z 407 (M+H)$^+$ (ES$^+$), at 1.83 min, 190-320 nm.

A 5-mL flask under $N_2$ was charged with a mixture of tert-butyl ((3R)-1-(2-((tert-butoxycarbonyl)amino)-7-(oxetan-3-yl)-7,8-dihydro-6H-pyrimido[5,4-b][1,4]oxazin-4-yl)pyrrolidin-3-yl)(methyl)carbamate and tert-butyl ((3R)-1-(2-amino-7-(oxetan-3-yl)-7,8-dihydro-6H-pyrimido[5,4-b][1,4]oxazin-4-yl)pyrrolidin-3-yl)(methyl)carbamate (total 0.0620 mmol) and DCM (1.0 mL). TFA (0.2 mL) was then added, and the resulting solution was stirred at room temperature for 5 h. The solution was co-evaporated with toluene under reduced pressure, and the residue was purified using purification method C to afford 4-((R)-3-(methylamino)pyrrolidin-1-yl)-7-(oxetan-3-yl)-7,8-dihydro-6H-pyrimido[5,4-b][1,4]oxazin-2-amine, Example 1-13 (13.6 mg, 72%) as a colorless solid after lyophilization. 55 The data for Example-1-13 are in Table 3.

Route E

Typical procedure for the preparation of fused pyrimidines as exemplified by the preparation of Example 1-14, (R)-7,7-dimethyl-4-(3-(methylamino)pyrrolidin-1-yl)-7,8-dihydro-6H-pyrimido[5,4-b][1,4]oxazin-2-amine dihydrochloride salt

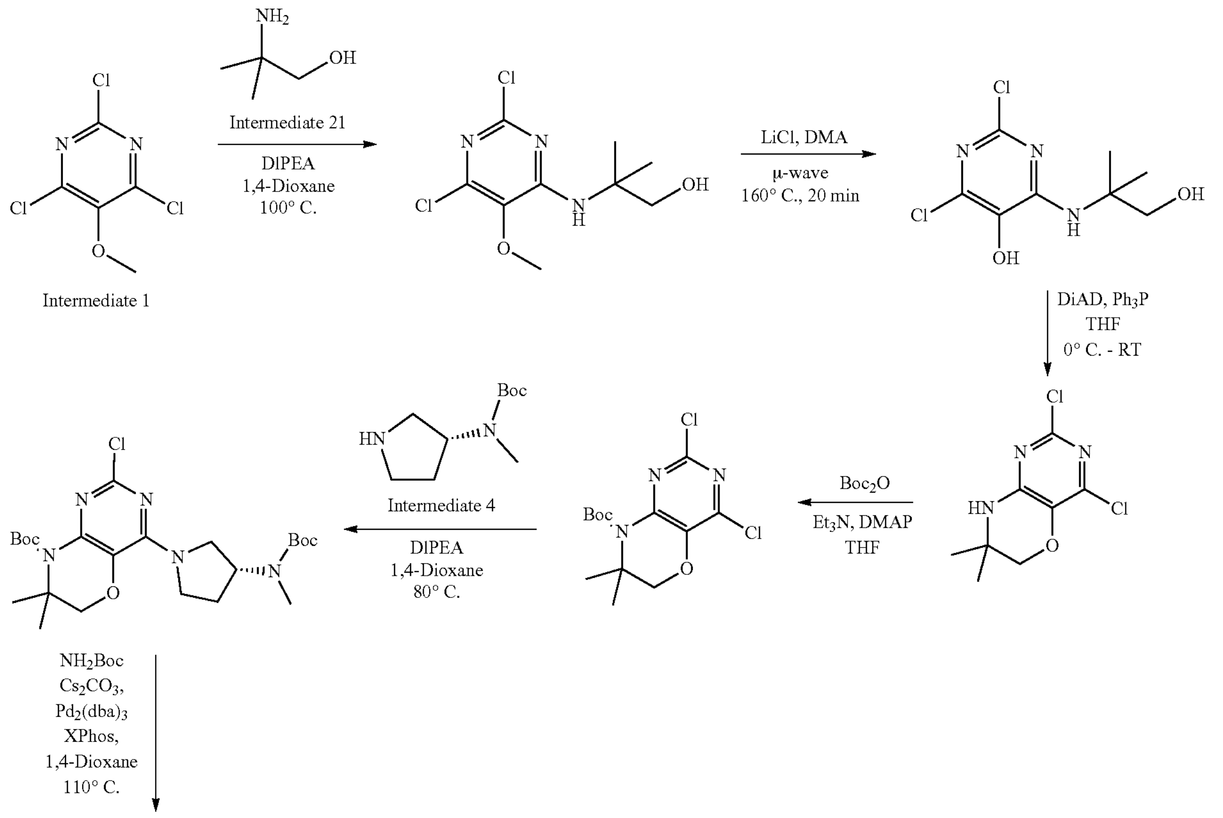

-continued

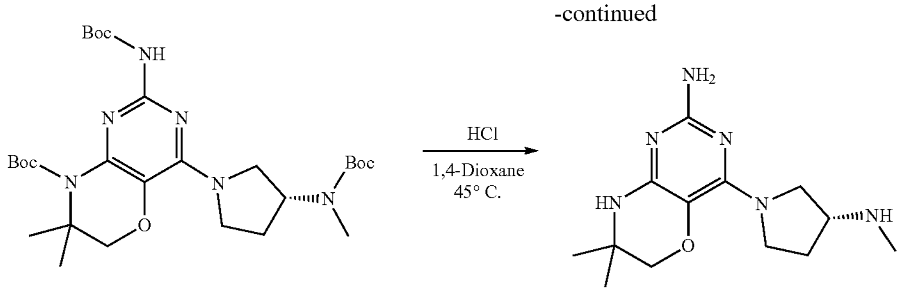

Example 1-14

To a solution of 2,4,6-trichloro-5-methoxypyrimidine (Intermediate 1) (1.00 g, 4.68 mmol) in 1,4-dioxane (7.00 mL) were added 2-amino-2-methylpropan-1-ol (Intermediate 21) (0.47 mL, 4.92 mmol) and DIPEA (2.00 mL, 11.7 mmol) and the reaction mixture was heated at 100° C. for 3 h. After cooling to room temperature, the mixture was diluted with water and the aqueous layer was extracted with EtOAc (3x20 mL). The combined organic extracts were washed with brine, dried ($MgSO_4$), filtered and concentrated under reduced pressure. The residue was purified by silica gel chromatography (dry pack) using a gradient of EtOAc (0-80%) in hexanes to provide 2-((2,6-dichloro-5-methoxypyrimidin-4-yl)amino)-2-methylpropan-1-ol (891 mg, 72%) as a colorless oil which crystallised to a white solid on standing.

LCMS (System 1, Method E): m/z 266/268 $(M+H)^+$ $(ES^+)$, at 2.05 min, 190-320 nm.

To a solution of 2-((2,6-dichloro-5-methoxypyrimidin-4-yl)amino)-2-methylpropan-1-ol (800 mg, 3.01 mmol) in DMA (6.0 mL) was added LiCl (318 mg, 7.51 mmol) and the mixture was stirred at 160° C. under microwave heating for 20 min. After cooling to room temperature, the mixture was directly purified by reversed-phase column chromatography (C-18, isocratic 5:95, MeCN:0.1% formic acid in water) to provide 2,4-dichloro-6-((1-hydroxy-2-methylpropan-2-yl)amino)pyrimidin-5-ol formic acid salt (130 mg, 17%) as a brown oil.

LCMS (System 1, Method D): m/z 252/254 $(M+H)^+$ $(ES^+)$, at 1.99 min, 190-320 nm.

To a solution of 2,4-dichloro-6-((1-hydroxy-2-methylpropan-2-yl)amino)pyrimidin-5-ol formic acid salt (200 mg, 0.793 mmol) in THF (4.7 mL) cooled to 0° C., were added $Ph_3P$ (416 mg, 1.59 mmol) and DIAD (0.313 mL, 1.59 mmol) and the reaction mixture was stirred at room temperature overnight. The mixture was then concentrated to dryness to afford crude 2,4-dichloro-7,7-dimethyl-7,8-dihydro-6H-pyrimido[5,4-b][1,4]oxazine, which was used directly in the next step without any purification.

LCMS (System 1, Method D): m/z 234/236 $(M+H)^+$ $(ES^+)$, at 1.87 min, 190-320 nm.

To a solution of the crude 2,4-dichloro-7,7-dimethyl-7,8-dihydro-6H-pyrimido[5,4-b][1,4]oxazine (0.793 mmol) in THF (7.9 mL) were added di-tert-butyl dicarbonate (537 mg, 2.46 mmol), $Et_3N$ (0.33 mL, 2.46 mmol) and DMAP (48 mg, 0.396 mmol) and the reaction mixture was stirred at room temperature for 18 h. The mixture was then concentrated under reduced pressure and silica was added. The residue was purified by silica gel chromatography (dry pack) using a gradient of EtOAc (0-50%) in hexanes to provide tert-butyl 2,4-dichloro-7,7-dimethyl-6,7-dihydro-8H-pyrimido[5,4-b][1,4]oxazine-8-carboxylate (30 mg, 11% over 2 steps) as a colorless oil.

LCMS (System 1, Method D): m/z 278/280 $(M-56+H)^+$ $(ES^+)$, at 2.26 min, 190-320 nm.

To a solution of tert-butyl 2,4-dichloro-7,7-dimethyl-6,7-dihydro-8H-pyrimido[5,4-b][1,4]oxazine-8-carboxylate (30 mg, 0.089 mmol) in 1,4-dioxane (0.3 mL) were added tert-butyl (R)-methyl(pyrrolidin-3-yl)carbamate (Intermediate 4) (20 mg, 0.099 mmol) and DIPEA (0.031 mL, 0.18 mmol) and the mixture was heated to 80° C. for 18 h. After cooling to room temperature, the mixture was diluted with water and the aqueous layer was extracted with EtOAc (3x10.0 mL). The combined organic extracts were dried ($MgSO_4$), filtered and concentrated under reduced pressure. The residue was purified by silica gel chromatography (dry pack) using a gradient of EtOAc (0-60%) in hexanes to provide tert-butyl (R)-4-(3-((tert-butoxycarbonyl)(methyl)amino)pyrrolidin-1-yl)-2-chloro-7,7-dimethyl-6,7-dihydro-8H-pyrimido[5,4-b][1,4]oxazine-8-carboxylate (37 mg, 83%) as a colorless oil.

LCMS (System 1, Method D): m/z 442/444 $(M-56+H)^+$ $(ES^+)$, at 2.41 min, 190-320 nm.

To a degassed solution of tert-butyl (R)-4-(3-((tert-butoxycarbonyl)(methyl)amino)pyrrolidin-1-yl)-2-chloro-7,7-dimethyl-6,7-dihydro-8H-pyrimido[5,4-b][1,4]oxazine-8-carboxylate (37 mg, 0.074 mmol) and tert-butyl carbamate (13 mg, 0.111 mmol) in 1,4-dioxane (0.74 mL) were added $Cs_2CO_3$ (61 mg, 0.186 mmol), tris(dibenzylideneacetone)dipalladium(0) (CAS: 51364-51-3) (6.8 mg, 0.00743 mmol) and XPhos (CAS: 564483-18-7) (7.1 mg, 0.0149 mmol) and the reaction mixture was heated to 110° C. for 2 h. After cooling to room temperature, the mixture was filtered through a pad of Celite and the residue washed with EtOAc. The filtrate was concentrated under reduced pressure and the residue purified by silica gel chromatography using a gradient of EtOAc (0-100%) in hexanes, and then by reversed-phase column chromatography (C-18, isochratic 5:95, MeCN:10 mM ammonium bicarbonate in water, pH 10) to provide tert-butyl (R)-4-(3-((tert-butoxycarbonyl)(methyl)amino)pyrrolidin-1-yl)-2-((tert-butoxycarbonyl)amino)-7,7-dimethyl-6,7-dihydro-8H-pyrimido[5,4-b][1,4]oxazine-8-carboxylate (22 mg, 51%) as a colorless oil.

LCMS (System 1, Method D): m/z 579 $(M+H)^+$ $(ES^+)$, at 2.29 min, 190-320 nm.

To a solution of tert-butyl (R)-4-(3-((tert-butoxycarbonyl)(methyl)amino)pyrrolidin-1-yl)-2-((tert-butoxycarbonyl)amino)-7,7-dimethyl-6,7-dihydro-8H-pyrimido[5,4-b][1,4]oxazine-8-carboxylate (22 mg, 0.038 mmol) in 1,4-dioxane (0.48 mL) was added HCl solution in 1,4-dioxane (4M, 0.48 mL, 1.9 mmol) and the reaction mixture was heated to 45° C. for 3 h. After cooling to room temperature, the mixture was concentrated to dryness. The residue was diluted with water and purified by reversed-phase column chromatography ($H_2O$ injection, 4 g C-18, isocratic 5:95, MeCN:$H_2O$) to afford (R)-7,7-dimethyl-4-(3-(methylamino)pyrrolidin-1-yl)-7,8-dihydro-6H-pyrimido[5,4-b][1,4]oxazin-2-amine dihydrochloride salt, Example 1-14 (12 mg, 90%) as a white solid. The data for Example 1-14 are in Table 3.

Route F

Typical procedure for the preparation of fused pyrimidines as exemplified by the preparation of Example 1-20, 7-isopropyl-8-methyl-4-((R)-3-(methylamino)pyrrolidin-1-yl)-7,8-dihydro-6H-pyrimido[5,4-b][1,4]oxazin-2-amine

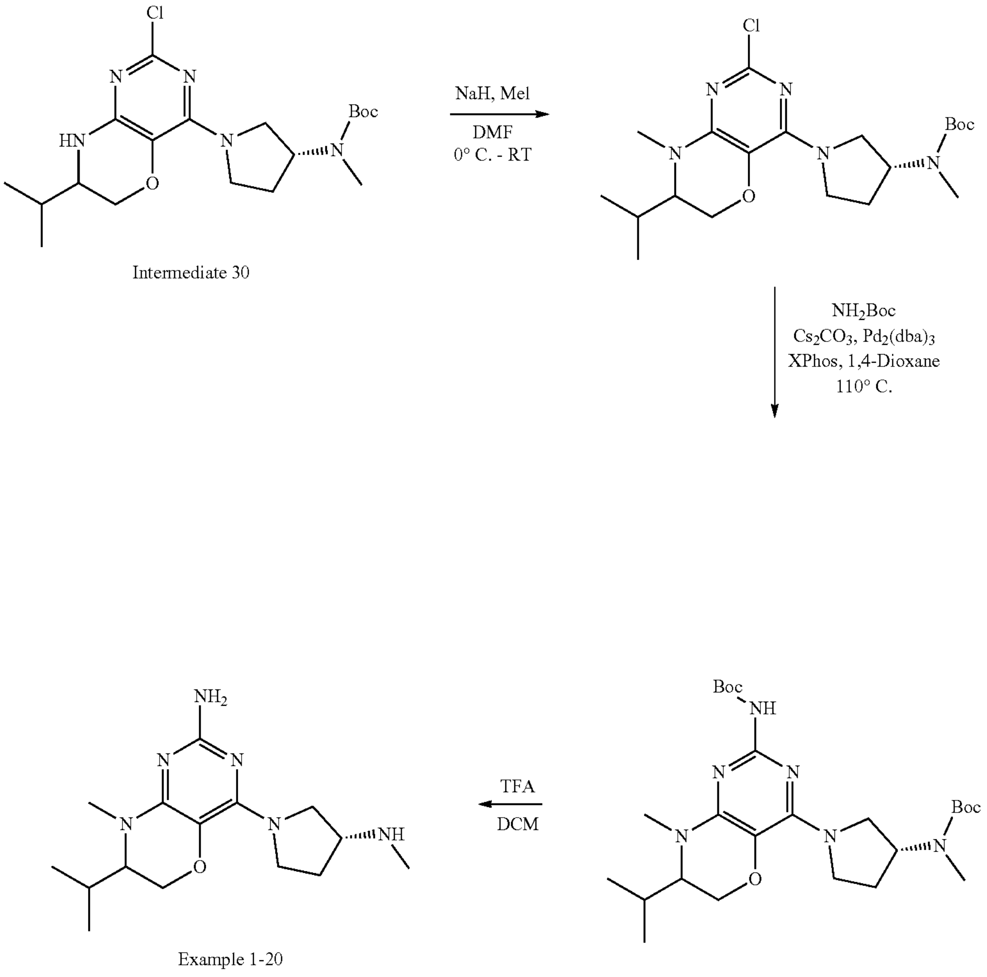

Intermediate 30

Example 1-20

To a solution of tert-butyl ((3R)-1-(2-chloro-7-isopropyl-7,8-dihydro-6H-pyrimido[5,4-b][1,4]oxazin-4-yl)pyrrolidin-3-yl)(methyl)carbamate (Intermediate 30) (100 mg, 0.243 mmol) in DMF (1.30 mL), cooled to 0° C., were added NaH (60% dispersion in mineral oil, 15 mg, 0.364 mmol) and iodomethane (0.018 mL, 0.291 mmol) and the reaction mixture was stirred at 0° C. for 30 min then warmed to room temperature and stirred for an additional 1 h. The mixture was then quenched with water and the aqueous layer was extracted with EtOAc (3×5.00 mL). The combined organic extracts were dried ($MgSO_4$), filtered and concentrated under reduced pressure. The residue was purified by silica gel chromatography (dry pack) using a gradient of EtOAc (0-40%) in hexanes to provide tert-butyl ((3R)-1-(2-chloro-7-isopropyl-8-methyl-7,8-dihydro-6H-pyrimido[5,4-b][1,4]oxazin-4-yl)pyrrolidin-3-yl)(methyl)carbamate (68 mg, 66%) as a pale yellow oil.

LCMS (System 1, Method D): m/z 426/428 $(M+H)^+$ $(ES^+)$, at 2.83 min, 190-320 nm.

To a degassed solution of tert-butyl ((3R)-1-(2-chloro-7-isopropyl-8-methyl-7,8-dihydro-6H-pyrimido[5,4-b][1,4]oxazin-4-yl)pyrrolidin-3-yi)(methyl)carbamate (68 mg, 0.16 mmol) and tert-butyl carbamate (19 mg, 0.16 mmol) in 1,4-dioxane (1.60 mL) were added $Cs_2CO_3$ (130 mg, 0.399 mmol), tris(dibenzylideneacetone)dipalladium(0) (CAS: 51364-51-3) (14.6 mg, 0.016 mmol) and XPhos (CAS: 564483-18-7) (15.2 mg, 0.032 mmol) and the reaction mixture was heated at 110° C. for 18 h. After cooling to room temperature, the mixture was filtered through a pad of Celite and the residue was washed with EtOAc. The filtrate was concentrated under reduced pressure and the residue was purified by silica gel chromatography using a gradient of EtOAc (0-50%) in hexanes to provide tert-butyl ((3R)-1-(2-((tert-butoxycarbonyl)amino)-7-isopropyl-8-methyl-7,8-dihydro-6H-pyrimido[5,4-b][1,4]oxazin-4-yl)pyrrolidin-3-yl)(methyl)carbamate (43 mg, 53%) as a pale yellow oil.

LCMS (System 1, Method D): m/z 507 $(M+H)^+$ $(ES^+)$, at 2.17 min, 190-320 nm.

To a solution of tert-butyl ((3R)-1-(2-((tert-butoxycarbonyl)amino)-7-isopropyl-8-methyl-7,8-dihydro-6H-pyrimido[5,4-b][1,4]oxazin-4-yl)pyrrolidin-3-yl)(methyl)carbamate (43 mg, 0.085 mmol) in DCM (0.50 mL) was added TFA (0.50 mL) and the reaction mixture was stirred at room temperature for 2 h. The mixture was then concentrated to dryness and the residue was purified by purification method D to provide 7-isopropyl-8-methyl-4-((R)-3-(methylamino) pyrrolidin-1-yl)-7,8-dihydro-6H-pyrimido[5,4-b][1,4] oxazin-2-amine, Example 1-20 (12 mg, 46%) as a white solid.

The data for Example 1-20 are in Table 3.

Route G

Typical procedure for the preparation of fused pyrimidines as exemplified by the preparation of Example 1-21, 4-((R)-3-(methylamino)pyrrolidin-1-yl)-6a,7,8,9-tetrahydro-6H-pyrimido[5,4-b]pyrrolo [1,2-d][1,4]oxazin-2-amine

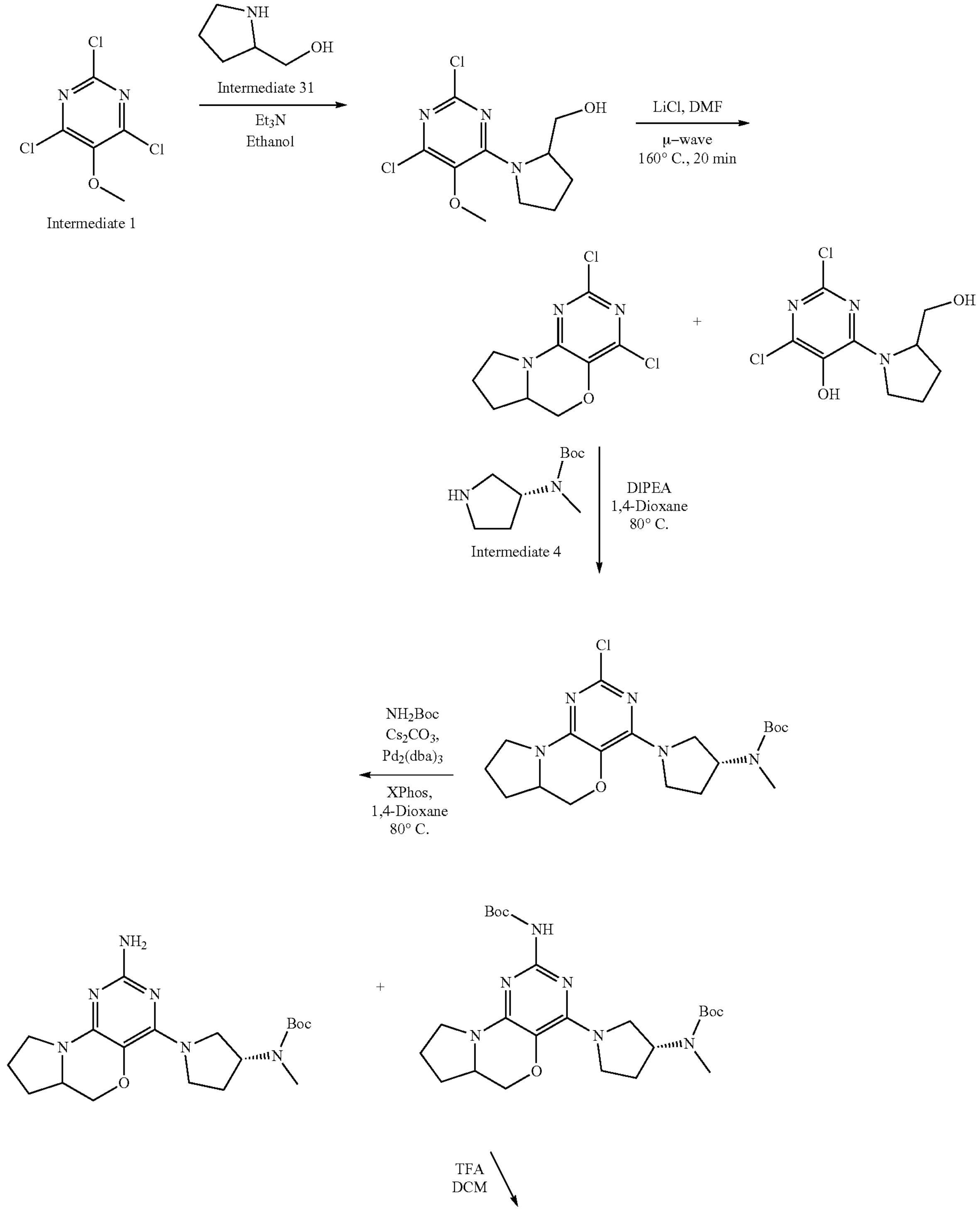

-continued

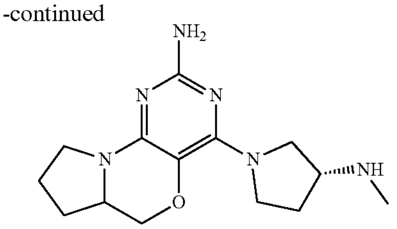

Example 1-21

To a solution of 2,4,6-trichloro-5-methoxypyrimidine (Intermediate 1) (320 mg, 1.5 mmol) in ethanol (10 mL) was added pyrrolidin-2-ylmethanol (Intermediate 31) (227 mg, 2.25 mmol) and TEA (0.42 mL, 3.0 mmol) and the reaction mixture was stirred at RT for 1 h. The reaction mixture was concentrated under reduced pressure and the residue was dissolved in DCM (10 mL). The DCM solution was washed with water (10 mL) and dried over $Na_2SO_4$ concentrated under reduced pressure. The residue was purified using flash chromatography with 0-60% ethyl acetate in hexanes to give (1-(2,6-dichloro-5-methoxypyrimidin-4-yl)pyrrolidin-2-yl) methanol (400 mg, 96%) as a white solid.

LCMS (System 1, Method D): m/z 278/280 $(M+H)^+$ $(ES^+)$, at 2.13 min, 190-320 nm.

To a solution of (1-(2,6-dichloro-5-methoxypyrimidin-4-yl)pyrrolidin-2-yl)methanol (400 mg, 1.44 mmol) in DMF (5 mL) was added LiCl (152 mg, 3.6 mmol) and the mixture was stirred at 160° C. under microwave heating for 20 min. The reaction mixture was concentrated and the residue was purified by flash chromatography using 0-100% ethyl acetate in hexanes to afford 2,4-dichloro-6a,7,8,9-tetrahydro-6H-pyrimido[5,4-b]pyrrolo[1,2-d][1,4]oxazine (150 mg, 42%) as white solid and 2,4-dichloro-6-(2-(hydroxymethyl)pyrrolidin=1-yl)pyrimidin-5-ol (100 mg, 26%) as a white solid. 2,4-Dichloro-6a,7,8,9-tetrahydro-6H-pyrimido[5,4-b]pyrrolo[1,2-d][1,4]oxazine: $^1H$ NMR (500 MHz, Chloroform-d) δ 1.48-1.58 (m, 1H), 1.99-2.10 (m, 1H), 2.14-2.19 (m, 1H), 2.20-2.26 (m, 1H), 3.44-3.50 (m, 1H), 3.56-3.64 (m, 1H), 3.72-3.80 (m, 2H), 4.62-4.67 (m, 1H).

LCMS (System 1, Method D): m/z 246/248 $(M+H)^+$ $(ES^+)$, at 2.20 min, 190-320 nm.

2,4-Dichloro-6-(2-(hydroxymethyl)pyrrolidin-1-yl)pyrimidin-5-ol: LCMS (System 1, Method D): m/z 264/266 $(M+H)^+$ $(ES^+)$, at 1.97 min, 190-320 nm.

To a solution of 2,4-dichloro-6a,7,8,9-tetrahydro-6H-pyrimido[5,4-b]pyrrolo[1,2-d][1,4]oxazine (200 mg, 0.813 mmol) and tert-butyl (R)-methyl(pyrrolidin-3-yl)carbamate (Intermediate 4) (0.163 g, 0.813 mmol) in 1,4-dioxane (4 mL) was added DIPEA (0.28 mL, 1.63 mmol) and the resulting mixture was stirred at 80° C. for 24 h. The reaction mixture was concentrated and the residue was purified by flash chromatography using 0-60% ethyl acetate in hexanes to afford tert-butyl ((3R)-1-(2-chloro-6a,7,8,9-tetrahydro-6H-pyrimido[5,4-b]pyrrolo[1,2-d][1,4]oxazin-4-yl)pyrrolidin-3-yl)(methyl)carbamate (252 mg, 75%) as a white solid.

LCMS (System 1, Method D): m/z 410/412 $(M+H)^+$ $(ES^+)$, at 2.64 min, 190-320 nm.

To a degassed solution of tert-butyl ((3R)-1-(2-chloro-6a,7,8,9-tetrahydro-6H-pyrimido[5,4-b]pyrrolo[1,2-d][1,4]oxazin-4-yl)pyrrolidin-3-yl)(methyl)carbamate (150 mg, 0.366 mmol) and tert-butyl carbamate (42.9 mg, 0.366 mmol) in 1,4-dioxane (4 mL) was added $Cs_2CO_3$ (0.477 g, 1.46 mol), tris(dibenzylideneacetone)dipalladium(0) (CAS: 51364-51-3) (21.0 mg, 0.0365 mmol) and XPhos (CAS: 564483-18-7) (34.9 mg, 0.0732 mmol). The solution was degassed with $N_2$ and stirred at 80° C. for 18 h. A mixture of tert-butyl ((3R)-1-(2-((tert-butoxycarbonyl)amino)-6a,7,8,9-tetrahydro-6H-pyrimido[5,4-b]pyrrolo[1,2-d][1,4]oxazin-4-yl)pyrrolidin-3-yl)(methyl)carbamate and tert-butyl ((3R)-1-(2-amino-6a,7,8,9-tetrahydro-6H-pyrimido[5,4-b]pyrrolo[1,2-d][1,4]oxazin-4-yl)pyrrolidin-3-yl)(methyl) carbamate was observed by LCMS. The reaction mixture was filtered over a bed of Celite under vacuum, washing the residue with ethyl acetate and the filtrate was concentrated to obtain a mixture of the two products as a yellow oil, which was used directly in the next step without any purification.

LCMS (System 1, Method D): m/z 491 $(M+H)^+$ $(ES^+)$, at 2.11 min, 190-320 nm.

LCMS (System 1, Method D): m/z 391 $(M+H)^+$ $(ES^+)$, at 1.91 min, 190-320 nm.

The yellow oil from the step above was dissolved in DCM (2.0 mL) and TFA (2.0 mL) was added at RT. The mixture was stirred at RT for 1 h and then concentrated to dryness. The residue was purified using reversed-phase column chromatography (C-18, isochratic 5:95, MeCN:10 mM ammonium bicarbonate in water, pH 10) to afford 4-((R)-3-(methylamino)pyrrolidin-1-yl)-6a,7,8,9-tetrahydro-6H-pyrimido[5,4-b]pyrrolo[1,2-d][1,4]oxazin-2-amine, Example 1-21 (21 mg, 20% over two steps) as a white solid.

The data for Example 1-21 are in Table 3.

Route H

Typical procedure for the preparation of fused pyrimidines as exemplified by the preparation of Example 7-1, (R)-1-((R)-7-isopropyl-7,8-dihydro-6H-pyrimido[5,4-b][1,4]oxazin-4-yl)-N-methylpyrrolidin-3-amine

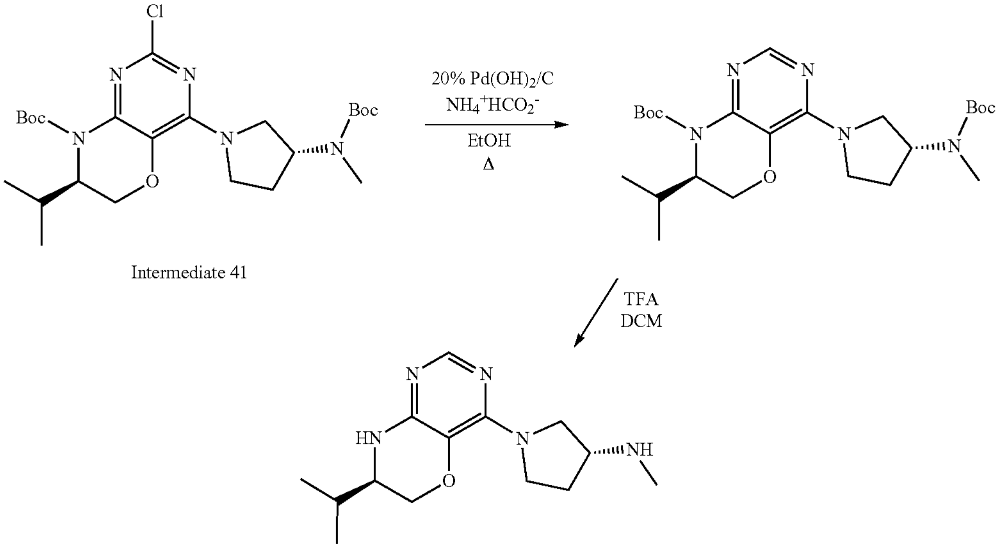

Intermediate 41

Example 7-1

A 25-mL flask was charged with 20% $Pd(OH)_2/C$ (15.1 mg, 10 mol % Pd). The atmosphere was replaced with $N_2$, then a solution of tert-butyl (R)-4-((R)-3-((tert-butoxycarbonyl)(methyl)amino)pyrrolidin-1-yl)-2-chloro-7-isopropyl-6,7-dihydro-8H-pyrimido[5,4-b][1,4]oxazine-8-carboxylate (Intermediate 41) (110 mg, 0.215 mmol) in EtOH (2.1 mL) was added followed by ammonium formate (135 mg, 2.15 mmol). The reaction mixture was heated at refluxed for 3 h. After cooling to room temperature, the reaction mixture was filtered through a pad of Celite and the residue was washed several times with MeOH. The filtrate was concentrated under reduced pressure to give tert-butyl (R)-4-((R)-3-((tert-butoxycarbonyl)(methyl)amino)pyrrolidin-1-yl)-7-isopropyl-6,7-dihydro-8H-pyrimido[5,4-b][1,4]oxazine-8-carboxylate as a white solid (103 mg, 100%), which was used directly in the next step without further purification.

LCMS (System 1, Method D): m/z 478 $(M+H)^+$ $(ES^+)$, at 2.22 min, 190-320 nm.

To a solution of tert-butyl (R)-4-((R)-3-((tert-butoxycarbonyl)(methyl)amino)pyrrolidin-1-yl)-7-isopropyl-6,7-dihydro-8H-pyrimido[5,4-b][1,4]oxazine-8-carboxylate (103 mg, 0.216 mmol) in DCM (1.00 mL) was added TFA (1.00 mL) and the reaction mixture was stirred at room temperature for 2 h. The mixture was then concentrated to dryness and the residue was purified by purification method E to provide (R)-1-((R)-7-isopropyl-7,8-dihydro-6H-pyrimido[5,4-b][1,4]oxazin-4-yl)-N-methylpyrrolidin-3-amine, Example 7-1 (43 mg, 72%) as a white foam.

The data for Example 7-1 are in Table 3.

Route I

Typical procedure for the preparation of fused pyrimidines as exemplified by the preparation of Example 7-2, (R)-1-((R)-7-cyclopropyl-7,8-dihydro-6H-pyrimido[5,4-b][1,4]oxazin-4-yl)-N-methylpyrrolidin-3-amine

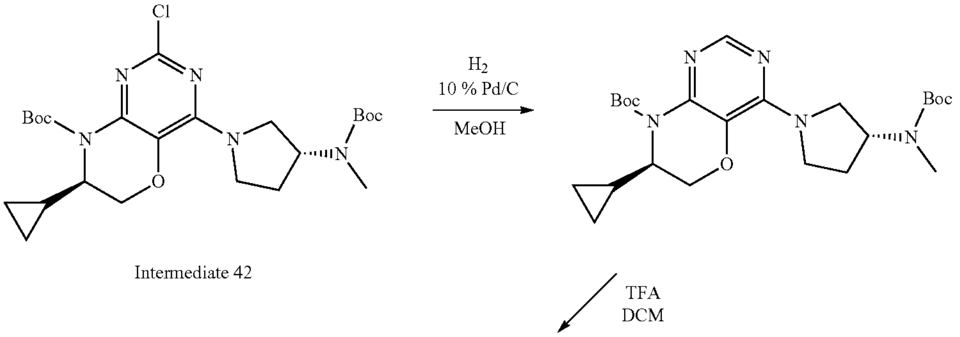

Intermediate 42

-continued

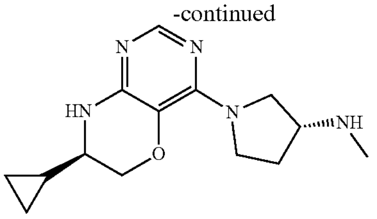

Example 7-2

To tert-butyl (R)-4-((R)-3-((tert-butoxycarbonyl)(methyl) amino)pyrrolidin-1-yl)-2-chloro-7-cyclopropyl-6,7-dihydro-8H-pyrimido[5,4-b][1,4]oxazine-8-carboxylate (Intermediate 42) (270 mg, 0.530 mmol) in MeOH (20 mL) was added 10% Pd/C catalyst (50 mg) and the resulting mixture was stirred at RT under $H_2$ (1 atmosphere pressure) for 8 h. The reaction mixture was then filtered on a bed of Celite and the residue washed with MeOH. The filtrate was concentrated under reduced pressure to afford tert-butyl (R)-4-((R)-3-((tert-butoxycarbonyl)(methyl)amino)pyrrolidin-1-yl)-7-cyclopropyl-6,7-dihydro-8H-pyrimido[5,4-b][1,4]oxazine-8-carboxylate (250 mg, 99%) as a brown solid, which was forwarded to the next step without purification.

LCMS (System 4, Method C): m/z 476 $(M+H)^+$ $(ES^+)$, at 4.84 min, 228 nm tert-Butyl (R)-4-((R)-3-((tert-butoxycarbonyl)(methyl)amino)pyrrolidin-1-yl)-7-cyclopropyl-6,7-dihydro-8H-pyrimido[5,4-b][1,4]oxazine-8-carboxylate (250 mg, 0.526 mmol) was dissolved in DCM (5.00 mL), and TFA (5 mL) was added dropwise at 0° C., and the resulting mixture was stirred for 2 h at room temperature. The solvent was removed in-vacuo and the residue was triturated with hexanes (2×20 mL) and diethyl ether (2×10 mL) to give the crude product (150 mg), which was purified by purification method F to afford (R)-1-((R)-7-cyclopropyl-7,8-dihydro-6H-pyrimido[5,4-b][1,4]oxazin-4-yl)-N-methylpyrrolidin-3-amine, Example 7-2 (35 mg, 22%) as a white solid.

The data for Example 7-2 are in Table 3.

Route J

Typical procedure for the preparation of fused pyrimidines as exemplified by the preparation of Example 10-1, (3R)-1-(7-isopropyl-2-methyl-7,8-dihydro-6H-pyrimido[5,4-b][1,4]oxazin-4-yl)-N-methylpyrrolidin-3-amine

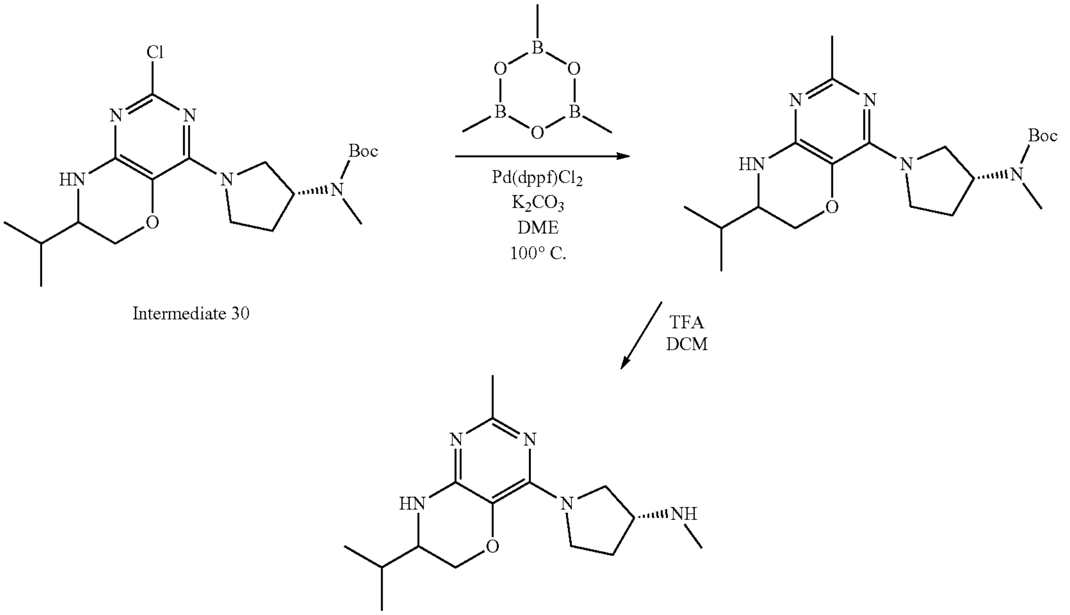

Intermediate 30

Example 10-1

A vial was charged with tert-butyl ((3R)-1-(2-chloro-7-isopropyl-7,8-dihydro-6H-pyrimido[5,4-b][1,4]oxazin-4-yl) pyrrolidin-3-yl)(methyl)carbamate (Intermediate 30) (110 mg, 0.267 mmol), trimethylboroxine (CAS: 823-96-1) (0.15 mL, 1.07 mmol), $K_2CO_3$ (74 mg, 0.534 mmol) and DME (5.80 mL). Then [1,1'-bis(diphenylphosphino)ferrocene]dichloropalladium(II) (CAS: 72287-26-4) (20 mg, 0.027 mmol) was added and the mixture was degassed with nitrogen for 15 min. The tube was sealed and the mixture was heated at 100° C. for 18 h. After cooling to room temperature, the mixture was filtered through a pad of Celite and the residue was washed with EtOAc. The filtrate was concentrated under reduced pressure and the residue was purified by silica gel chromatography using a gradient of EtOAc (0-100%) in hexanes to provide tert-butyl ((3R)-1-

(7-isopropyl-2-methyl-7,8-dihydro-6H-pyrimido[5,4-b][1,4]oxazin-4-yl)pyrrolidin-3-yl)(methyl)carbamate (69 mg, 66%) as a colorless oil.

LCMS (System 1, Method D): m/z 392 $(M+H)^+$ $(ES^+)$, at 2.02 min, 190-320 nm.

To a solution of tert-butyl ((3R)-1-(7-isopropyl-2-methyl-7,8-dihydro-6H-pyrimido[5,4-b][1,4]oxazin-4-yl)pyrrolidin-3-yl)(methyl)carbamate (61 mg, 0.156 mmol) in DCM (1.00 mL) was added TFA (1.00 mL) and the reaction mixture was stirred at room temperature for 1 h. After concentration to dryness, the residue was purified by purification method D to provide (3R)-1-(7-isopropyl-2-methyl-7,8-dihydro-6H-pyrimido[5,4-b][1,4]oxazin-4-yl)-N-methylpyrrolidin-3-amine, Example 10-1 (35 mg, 77%) as a white solid.

The data for Example 10-1 are in Table 3.

Route K

Typical procedure for the preparation of fused pyrimidines as exemplified by the preparation of Example 11-10, (S)-4-((R)-3-(methylamino)pyrrolidin-1-yl)-6,7,7a,8,9,10-hexahydropyrimido[5,4-b]pyrrolo[1,2-d][1,4]oxazepin-2-amine

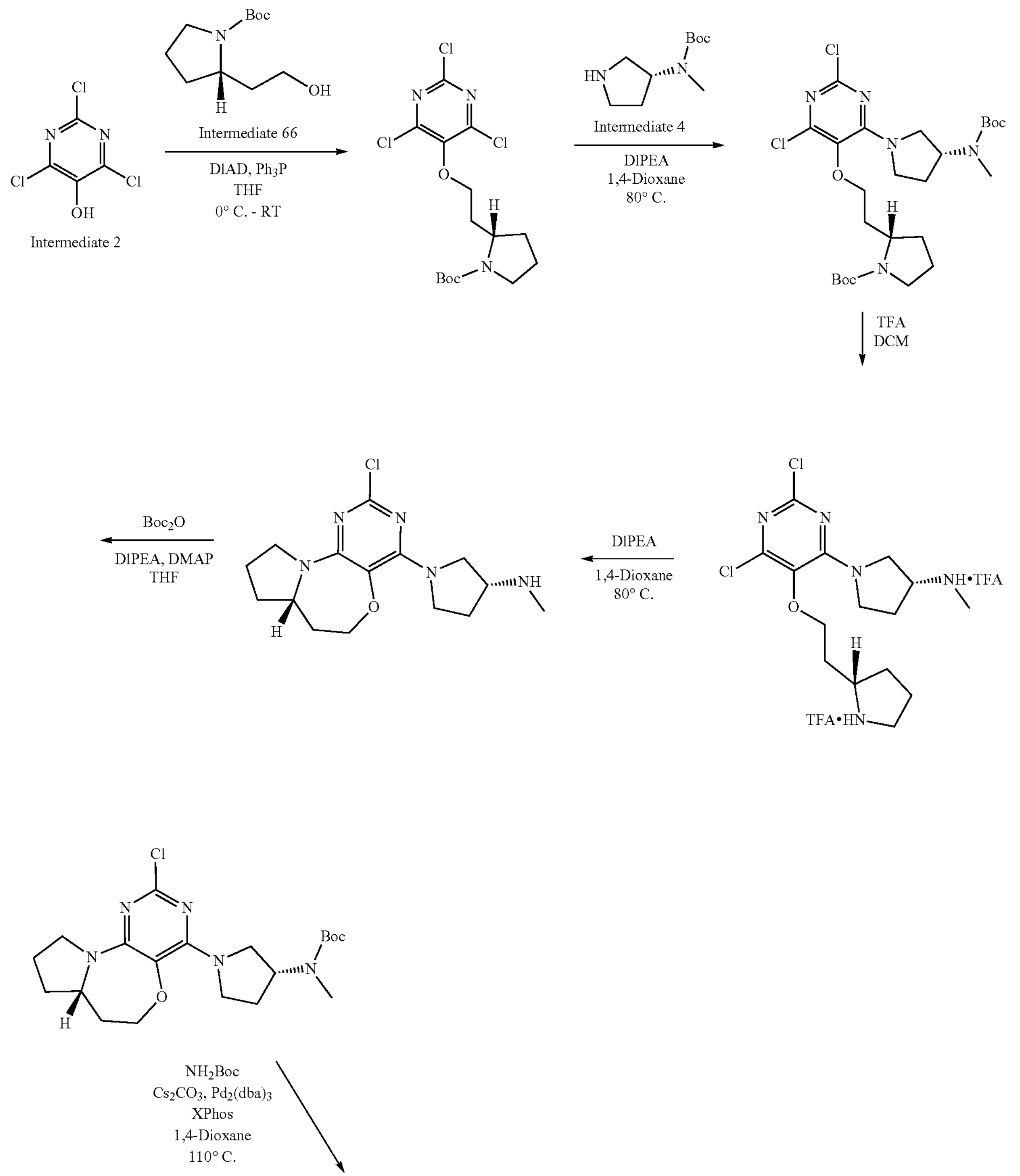

-continued

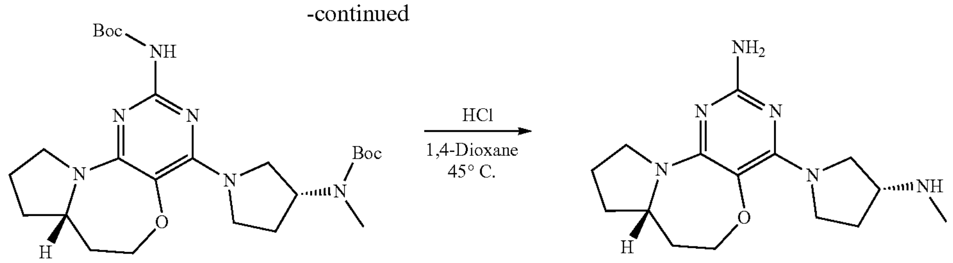

Example 11-10

To a solution of 2,4,6-trichloropyrimidin-5-ol (Intermediate 2) (550 mg, 2.76 mmol) and tert-butyl (S)-2-(2-hydroxyethyl)pyrrolidine-1-carboxylate (Intermediate 66) (1.19 g, 5.52 mmol) in THE (15.5 mL), cooled to 0° C., were added $Ph_3P$ (1.09 g, 4.14 mmol) and DIAD (0.815 mL, 4.14 mmol) and the reaction mixture was stirred at room temperature for 3 h. THE was then removed by concentration under reduced pressure and silica was added. The residue was purified by silica gel chromatography (dry pack) using a gradient of EtOAc (0-50%) in hexanes to provide tert-butyl (S)-2-(2-((2,4,6-trichloropyrimidin-5-yl)oxy)ethyl) pyrrolidine-1-carboxylate (844 mg, 77%) as a colorless oil.

$^1$H NMR (400 MHz, Chloroform-d) δ 1.45 (s, 9H), 1.75-1.83 (m, 1H), 1.83-1.97 (m, 3H), 1.99-2.11 (m, 1H), 2.25-2.36 (m, 1H), 3.26-3.48 (m, 2H), 3.95-4.06 (m, 1H), 4.07-4.23 (m, 2H).

To a solution of tert-butyl (S)-2-(2-((2,4,6-trichloropyrimidin-5-yl)oxy)ethyl)pyrrolidine-1-carboxylate (820 mg, 2.07 mmol) and tert-butyl (R)-methyl(pyrrolidin-3-yl)carbamate (Intermediate 4) (414 mg, 2.07 mmol) in 1,4-dioxane (4.73 mL) was added DIPEA (1.08 mL, 6.2 mmol) and the reaction mixture was heated at 80° C. for 3 h. The mixture was then diluted with water and the aqueous layer was extracted with EtOAc (×3). The combined organic extracts were washed with brine, dried ($MgSO_4$), filtered and concentrated under reduced pressure. The residue was purified by silica gel chromatography (dry pack) using a gradient of EtOAc (0-80%) in hexanes to provide tert-butyl (S)-2-(2-((4-((R)-3-((tert-butoxycarbonyl)(methyl)amino) pyrrolidin-1-yl)-2,6-dichloropyrimidin-5-yl)oxy)ethyl)pyrrolidine-1-carboxylate (1.07 g, 92%) as a colorless oil.

LCMS (System 1, Method D): m/z 560/562 $(M+H)^+$ $(ES^+)$, at 2.39 min, 190-320 nm.

To a solution of tert-butyl (S)-2-(2-((4-((R)-3-((tert-butoxycarbonyl)(methyl)amino)pyrrolidin-1-yl)-2,6-dichloropyrimidin-5-yl)oxy)ethyl)pyrrolidine-1-carboxylate (1.07 g, 1.91 mmol) in DCM (8.00 mL) was added TFA (8.00 mL) and the reaction mixture was stirred at room temperature for 10 min. The mixture was then concentrated to dryness to provide the crude (R)-1-(2,6-dichloro-5-(2-((S)-pyrrolidin-2-yl)ethoxy)pyrimidin-4-yl)-N-methylpyrrolidin-3-amine ditrifluoroacetic acid salt as a yellow oil, which was used directly in the next step without any purification.

LCMS (System 1, Method D): m/z 360/362 $(M+H)^+$ $(ES^+)$, at 1.35 min, 190-320 nm.

To a solution of the crude (R)-1-(2,6-dichloro-5-(2-((S)-pyrrolidin-2-yl)ethoxy)pyrimidin-4-yl)-N-methylpyrrolidin-3-amine ditrifluoroacetic acid salt (1.91 mmol) in 1,4-dioxane (5.1 mL) was added DIPEA (1.33 mL, 7.64 mmol) and the reaction mixture was heated at 80° C. for 18 h. The mixture was then concentrated under reduced pressure and the residue was purified by silica gel chromatography (dry pack) using a gradient of MeOH (0-30%) in DCM to provide (R)-1-((S)-2-chloro-6,7,7a,8,9,10-hexahydropyrimido[5,4-b]pyrrolo[1,2-d][1,4]oxazepin-4-yl)-N-methylpyrrolidin-3-amine (620 mg, 100%) as a beige solid.

LCMS (System 1, Method D): m/z 324/326 $(M+H)^+$ $(ES^+)$, at 1.86 min, 190-320 nm.

To a solution of (R)-1-((S)-2-chloro-6,7,7a,8,9,10-hexahydropyrimido[5,4-b]pyrrolo[1,2-d][1,4]oxazepin-4-yl)-N-methylpyrrolidin-3-amine (618 mg, 1.91 mmol) in THE (19.1 mL) were added di-tert-butyl dicarbonate (833 mg, 3.82 mmol), $Et_3N$ (0.567 mL, 4.2 mmol) and DMAP (117 mg, 0.954 mmol) and the reaction mixture was stirred at room temperature for 18 h. The mixture was then concentrated under reduced pressure and silica was added. The residue was purified by silica gel chromatography (dry pack) using a gradient of EtOAc (0-70%) in hexane to provide tert-butyl ((R)-1-((S)-2-chloro-6,7,7a,8,9,10-hexahydropyrimido[5,4-b]pyrrolo[1,2-d][1,4]oxazepin-4-yl)pyrrolidin-3-yl)(methyl)carbamate (480 mg, 59%) as a colorless oil.

LCMS (System 1, Method D): m/z 424/426 $(M+H)^+$ $(ES^+)$, at 2.27 min, 190-320 nm.

To a degassed solution of tert-butyl ((R)-1-((S)-2-chloro-6,7,7a,8,9,10-hexahydropyrimido[5,4-b]pyrrolo[1,2-d][1,4] oxazepin-4-yl)pyrrolidin-3-yl)(methyl)carbamate (480 mg, 1.13 mmol) and tert-butyl carbamate (199 mg, 1.7 mmol) in 1,4-dioxane (11.3 mL) were added $Cs_2CO_3$ (922 mg, 2.83 mmol), tris(dibenzylideneacetone)dipalladium(0) (CAS: 51364-51-3) (104 mg, 0.113 mmol) and XPhos (CAS: 564483-18-7) (216 mg, 0.453 mmol) and the reaction mixture was heated at 110° C. for 3 h. After cooling to room temperature, the mixture was filtered through a pad of Celite and the residue washed with EtOAc. The filtrate was concentrated under reduced pressure and the residue was purified by silica gel chromatography using a gradient of EtOAc (0-100%) in hexanes and then by reversed-phase column chromatography (C-18, isochratic 5:95, MeCN:10 mM ammonium bicarbonate in water, pH 10) to provide tert-butyl ((R)-1-((S)-2-((tert-butoxycarbonyl)amino)-6,7,7a,8,9,10-hexahydropyrimido[5,4-b]pyrrolo[1,2-d][1,4]oxazepin-4-yl)pyrrolidin-3-yl)(methyl)carbamate (291 mg, 51%) as a beige solid.

LCMS (System 2, Method F): m/z 505 $(M+H)^+$ $(ES^+)$, at 2.15 min, 254 nm.

To a solution of tert-butyl ((R)-1-((S)-2-((tert-butoxycarbonyl)amino)-6,7,7a,8,9,10-hexahydropyrimido[5,4-b]pyrrolo[1,2-d][1,4]oxazepin-4-yl)pyrrolidin-3-yl)(methyl)carbamate (291 mg, 0.577 mmol) in 1,4-dioxane (5.77 mL) was added HCl solution in 1,4-dioxane (4 M, 5.77 mL, 23.1 mmol) and the reaction mixture was heated at 45° C. for 3 h. After cooling to room temperature, the mixture was concentrated to dryness. The residue was diluted with water and purified by reversed-phase column chromatography (C-18, isochratic 5:95, $MeCN:H_2O$) and then re-purified by reverse-phase column chromatography (C-18, isochratic 5:95, MeCN:10 mM ammonium bicarbonate in water, pH 10) to provide (S)-4-((R)-3-(Methylamino)pyrrolidin-1-yl)-6,7,7a,8,9,10-hexahydropyrimido[5,4-b]pyrrolo[1,2-d][1,4]oxazepin-2-amine, Example 11-10 (85 mg, 48%) as a white solid.

The data for Example 11-10 are in Table 3.

TABLE 2

| Intermediate Number | Name | Synthetic Route | Intermediates Used | Characterising Data |
|---|---|---|---|---|
| 1 | 2,4,6-Trichloro-5-methoxypyrimidine | — | — | Commercially available, CAS: 60703-46-0 |
| 2 | 2,4,6-Trichloropyrimidin-5-ol | — | — | LCMS (System 1, Method D): m/z 197/199 $(M-H)^-$ $(ES^-)$, at 1.93 min, 190-320 nm |
| 3 | tert-Butyl (2-hydroxyethyl)carbamate | — | — | Commercially available, CAS: 26690-80-2 |
| 4 | tert-Butyl (R)-methyl(pyrrolidin-3-yl) carbamate | | | Commercially available, CAS: 392338-15-7 |
| 5 | tert-Butyl (1-hydroxypropan-2-yl)carbamate | — | — | Commercially available, CAS: 147252-84-4 |
| 6 | tert-Butyl (R)-(1-hydroxybutan-2-yl)carbamate | — | — | Commercially available, CAS: 150736-71-3 |
| 7 | tert-Butyl (R)-(1-hydroxy-3-methylbutan-2-yl)carbamate | — | — | Commercially available, CAS: 106391-87-1 |
| 8 | tert-Butyl (S)-(1-hydroxy-3-methylbutan-2-yl)carbamate | — | — | Commercially available, CAS: 79069-14-0 |
| 9 | (R)-2-((tert-butoxycarbonyl)amino)-2-cyclopropylacetic acid | — | — | Commercially available, CAS: 609768-49-2 |
| 10 | tert-Butyl (R)-(1-cyclopropyl-2-hydroxyethyl)carbamate | 2 | 9 | LCMS (System 4, Method C): m/z 200 $(M-H)^-$ $(ES^-)$, at 2.19 min, 202 nm |
| 11 | tert-Butyl (1-hydroxy-4-methylpentan-2-yl)carbamate | — | — | Commercially available, CAS: 142121-48-0 |
| 12 | tert-Butyl (S)-(1-hydroxy-3-methoxypropan-2-yl)carbamate | — | — | Commercially available, CAS: 721927-59-9 |
| 13 | D-Allothreonine | — | — | Commercially available, CAS: 24830-94-2 |
| 14 | tert-Butyl ((2S,3R)-1-hydroxy-3-methoxybutan-2-yl)carbamate | 3 | 13 | $^1$H NMR (500 MHZ, Chloroform-d) § 1.22 (d, J = 6.4 Hz, 3H), 1.46 (s, 9H), 3.34 (s, 3H), 3.51-3.56 (m, 1H), 3.59-3.65 (m, 2H), 3.93-3.98 (m, 1H), 5.33-5.40 (m, 1H). One exchangeable proton not observed. |
| 15 | (tert-Butoxycarbonyl)-D-threonine | — | — | Commercially available, CAS: 55674-67-4 |
| 16 | tert-Butyl ((2S,3S)-1-hydroxy-3-methoxybutan-2-yl)carbamate | 3 Steps 2 and 3 | 15 | $^1$H NMR (400 MHZ, Chloroform-d) o 1.17 (d, J = 6.2 Hz, 3H), 1.43 (s, 9H), 3.32 (s, 3H), 3.48-3.70 (m, 3H), 3.70-3.78 (m, 1H), 5.02-5.12 (m, 1H). One exchangeable proton not observed. |
| 17 | 3-(tert-Butyl) 4-methyl (S)-2,2-dimethyloxazolidine-3,4-dicarboxylate | — | — | Commercially available, CAS: 108149-60-6 |
| 18 | tert-Butyl (S)-(1-hydroxy-3-methoxy-3-methylbutan-2-yl)carbamate | 4 | 17 | $^1$H NMR (500 MHZ, Chloroform-d) δ 1.22 (s, 3H), 1.27 (s, 3H), 1.45 (s, 9H), 3.18-3.23 (m, 1H), 3.21 (s, 3H), 3.51-3.56 (m, 1H), 3.62-3.68 (m, 1H), 3.93-3.99 (m, 1H), 5.28-5.36 (m, 1H). |
| 19 | Methyl 2-(((benzyloxy)carbonyl)amino)-2-(oxetan-3-ylidene)acetate | — | — | Commercially available, CAS: 394653-39-5 |

TABLE 2-continued

| Intermediate Number | Name | Synthetic Route | Intermediates Used | Characterising Data |
|---|---|---|---|---|
| 20 | 2-(Trimethylsilyl)ethyl (2-hydroxy-1-(oxetan-3-yl)ethyl)carbamate | 5 | 19 | $^1$H NMR (400 MHZ, DMSO-$d_6$) δ 0.02 (s, 9H), 0.87-0.97 (m, 2H), 3.01-3.13 (m, 1H), 3.16-3.25 (m, 1H), 3.28-3.35 (m, 1H), 3.73-3.83 (m, 1H), 3.97-4.10 (m, 2H), 4.32-4.41 (m, 2H), 4.46-4.56 (m, 2H), 4.61 (t, J = 5.6 Hz, 1H), 6.87 (d, J = 8.9 Hz, 1H). |
| 21 | 2-Amino-2-methylpropan-1-ol | — | — | Commercially available, CAS: 124-68-5 |
| 22 | tert-Butyl (2-hydroxypropyl)carbamate | — | — | Commercially available, CAS: 95656-86-3 |
| 23 | (2R,3R)-3-Aminobutan-2-ol hydrochloride | — | — | Commercially available, CAS: 960008-54-2 |
| 24 | (2S,3R)-3-Aminobutan-2-ol hydrochloride | — | — | Commercially available, CAS: 1605313-24-3 |
| 25 | 2,4-Dichloro-6-(((2R,3S)-3-hydroxybutan-2-yl)amino)pyrimidin-5-ol | E Steps 1 and 2 | 1 and 24 | LCMS (System 1, Method D): m/z 252/254 $(M + H)^+$ $(ES^+)$, at 1.67 min, 190-320 nm. |
| 26 | tert-Butyl (2,6-dichloro-5-hydroxypyrimidin-4-yl)((2R,3S)-3-hydroxybutan-2-yl)carbamate | 6 | 25 | $^1$H NMR (400 MHZ, Chloroform-d) δ 1.07 (d, J = 7.2 Hz, 3H), 1.24 (d, J = 6.5 Hz, 3H), 1.49 (s, 9H), 4.24-4.37 (m, 2H). Two exchangeable protons not observed. |
| 27 | (2R,3S)-3-Aminobutan-2-ol hydrochloride | — | — | Commercially available, CAS: 126307-45-7 |
| 28 | (2S,3S)-3-Aminobutan-2-ol hydrochloride | — | — | Commercially available, CAS: 310450-42-1 |
| 29 | tert-Butyl (1-hydroxy-3-methylbutan-2-yl)carbamate. | — | — | Commercially available, CAS: 169556-48-3 |
| 30 | tert-Butyl ((3R)-1-(2-chloro-7-isopropyl-7,8-dihydro-6H-pyrimido[5,4-b][1,4]oxazin-4-yl)pyrrolidin-3-yl)(methyl)carbamate | A Steps 1 to 4 | 2, 29 and 4 | LCMS (System 1, Method D): m/z 412/414 $(M + H)^+$ $(ES^+)$, at 2.73 min, 190-320 nm. |
| 31 | Pyrrolidin-2-ylmethanol | — | — | Commercially available, CAS: 498-63-5 |
| 32 | (R)-(2-Methylpyrrolidin-2-yl)methanol hydrochloride | — | — | Commercially available, CAS: 1523530-30-4 |
| 33 | (S)-(2-Methylpyrrolidin-2-yl)methanol hydrochloride | — | — | Commercially available, CAS: 1523541-78-7 |
| 34 | tert-Butyl (R)-pyrrolidin-3-ylcarbamate | — | — | Commercially available, CAS: 122536-77-0 |
| 35 | Methyl 2-((tert-butoxycarbonyl)amino)-3,3,3-trifluoro-2-hydroxypropanoate | — | — | Commercially available, CAS: 126535-83-9 |
| 36 | tert-Butyl (1,1,1-trifluoro-3-hydroxypropan-2-yl)carbamate | 7 | 35 | $^1$H NMR (400 MHZ, DMSO-$d_6$) δ 1.40 (s, 9H), 3.46-3.55 (m, 1H), 3.60-3.68 (m, 1H), 4.07-4.21 (m, 1H), 5.04 (t, J = 5.9 Hz, 1H), 7.40 (d, J = 9.2 Hz, 1H). |
| 37 | tert-Butyl azetidin-3-yl(methyl)carbamate hydrochloride | — | — | Commercially available, CAS: 943060-59-1 |
| 38 | tert-Butyl azetidin-3-ylcarbamate hydrochloride | — | — | Commercially available, CAS: 217806-26-3 |
| 39 | 1-Methylpiperazine | — | — | Commercially available, CAS: 109-01-3 |
| 40 | tert-Butyl piperazine-1-carboxylate | — | — | Commercially available, CAS: 57260-71-6 |
| 41 | tert-Butyl (R)-4-((R)-3-((tert-butoxycarbonyl)(methyl)-amino)pyrrolidin-1-yl)-2-chloro-7-isopropyl-6,7-dihydro-8H-pyrimido[5,4-b][1,4]oxazine-8-carboxylate | A Steps 1 to 5 No DMF was used in Step 5 | 2, 7 and 4 | LCMS (System 1, Method D): m/z 456/458 $(M-56 + H)^+$ $(ES^+)$, at 2.97 min, 190-320 nm. |

TABLE 2-continued

| Intermediate Number | Name | Synthetic Route | Intermediates Used | Characterising Data |
|---|---|---|---|---|
| 42 | tert-Butyl (R)-4-((R)-3-((tert-butoxycarbonyl)(methyl)-amino)pyrrolidin-1-yl)-2-chloro-7-cyclopropyl-6,7-dihydro-8H-pyrimido[5,4-b][1,4]oxazine-8-carboxylate | B Steps 1 to 5 DCM was used in Step 4 | 2, 10 and 4 | LCMS (System 4, Method C): m/z 510/512 $(M + H)^+$ $(ES^+)$, at 5.72 min, 258 nm |
| 43 | tert-Butyl (1-hydroxy-3-methoxypropan-2-yl)carbamate | — | — | Commercially available, CAS: 1334171-66-2 |
| 44 | tert-Butyl 4-((R)-3-((tert-butoxycarbonyl)(methyl)-amino)pyrrolidin-1-yl)-2-chloro-7-(methoxymethyl)-6,7-dihydro-8H-pyrimido[5,4-b][1,4]oxazine-8-carboxylate | A Steps 1 to 5 No DMF or DMAP was used in Step 5 | 2, 43 and 4 | LCMS (System 1, Method D): m/z 458/460 $(M-56 + H)^+$ $(ES^+)$, at 2.81 min, 190-320 nm. |
| 45 | tert-Butyl (S)-4-((R)-3-((tert-butoxycarbonyl)(methyl)-amino)pyrrolidin-1-yl)-2-chloro-7-((R)-1-methoxyethyl)-6,7-dihydro-8H-pyrimido[5,4-b][1,4]oxazine-8-carboxylate | B Steps 1 to 5 | 2, 14 and 4 | LCMS (System 1, Method D): m/z 472/474 $(M-56 + H)^+$ $(ES^+)$, at 2.83 min, 190-320 nm. |
| 46 | tert-Butyl 4-((R)-3-((tert-butoxycarbonyl)(methyl)-amino)pyrrolidin-1-yl)-2-chloro-6-methyl-6,7-dihydro-8H-pyrimido[5,4-b][1,4]oxazine-8-carboxylate | A Steps 1 to 5 No DMF was used in Step 5 | 2, 22 and 4 | LCMS (System 1, Method D): m/z 428/430 $(M-56 + H)^+$ $(ES^+)$, at 2.81 min, 190-320 nm. |
| 47 | tert-Butyl (R)-4-((R)-3-((tert-butoxycarbonyl)amino)pyrrolidin-1-yl)-2-chloro-7-isopropyl-6,7-dihydro-8H-pyrimido[5,4-b][1,4]oxazine-8-carboxylate | A Steps 1 to 5 No DMF was used in Step 5 | 2, 7 and 34 | LCMS (System 1, Method D): m/z 442/444 $(M-56 + H)^+$ $(ES^+)$, at 2.81 min, 190-320 nm. |
| 48 | tert-Butyl (S)-4-((R)-3-((tert-butoxycarbonyl)amino)pyrrolidin-1-yl)-2-chloro-7-((R)-1-methoxyethyl)-6,7-dihydro-8H-pyrimido[5,4-b][1,4]oxazine-8-carboxylate | B Steps 1 to 5 | 2, 14 and 34 | LCMS (System 1, Method D): m/z 458/460 $(M-56 + H)^+$ $(ES^+)$, at 2.69 min, 190-320 nm. |
| 49 | tert-Butyl (R)-4-(3-((tert-butoxycarbonyl)(methyl)-amino)azetidin-1-yl)-2-chloro-7-isopropyl-6,7-dihydro-8H-pyrimido[5,4-b][1,4]oxazine-8-carboxylate | B Steps 1 to 5 | 2, 7 and 37 | LCMS (System 1, Method D): m/z 442/444 $(M-56 + H)^+$ $(ES^+)$, at 2.88 min, 190-320 nm. |
| 50 | tert-Butyl (3-hydroxypropyl)carbamate | — | — | Commercially available, CAS: 58885-58-8 |
| 51 | tert-Butyl (R)-(4-hydroxybutan-2-yl)carbamate | — | — | Commercially available, CAS: 167216-17-3 |
| 52 | tert-Butyl (S)-(4-hydroxybutan-2-yl)carbamate | — | — | Commercially available, CAS: 106539-36-0 |
| 53 | (R)-3-((tert-Butoxycarbonyl)amino)pentanoic acid | — | — | Commercially available, CAS: 183990-60-5 |
| 54 | tert-Butyl (R)-(1-hydroxypentan-3-yl)carbamate | 2 | 53 | LCMS (System 4, Method C): m/z 204 $(M + H)^+$ $(ES^+)$, at 3.14 min, 202 nm |

TABLE 2-continued

| Intermediate Number | Name | Synthetic Route | Intermediates Used | Characterising Data |
|---|---|---|---|---|
| 55 | (S)-3-((tert-Butoxycarbonyl)amino)-4-methylpentanoic acid | — | — | Commercially available, CAS: 179412-79-4 |
| 56 | tert-Butyl (S)-(1-hydroxy-4-methylpentan-3-yl)carbamate | 2 | 55 | LCMS (System 4, Method C): m/z 216 $(M-H)^-$ $(ES^-)$, at 3.32 min, 202 nm |
| 57 | (R)-3-((tert-Butoxycarbonyl)amino)-4-methylpentanoic acid | 1 | 1 | Commercially available, CAS: 183990-64-9 |
| 58 | tert-Butyl (R)-(1-hydroxy-4-methylpentan-3-yl)carbamate | 2 | 57 | LCMS (System 3, Method B): m/z 218 $(M+H)^+$ $(ES^+)$, at 1.47 min, 202 nm |
| 59 | tert-Butyl (3-hydroxy-2-methylpropyl)carbamate | — | — | Commercially available, CAS: 480451-99-8 |
| 60 | 2-(Aminomethyl)butanoic acid | — | — | Commercially available, CAS: 4385-92-6 |
| 61 | 2-(((tert-Butoxycarbonyl)amino)-methyl)butanoic acid | 8 | 60 | LCMS (System 4, Method C): m/z 216 $(M-H)^-$ $(ES^-)$, at 1.74 min, 202 nm |
| 62 | tert-Butyl (2-(hydroxymethyl)butyl)carbamate | 2 | 61 | LCMS (System 4, Method C): m/z 204 $(M+H)^+$ $(ES^+)$, at 3.12 min, 202 nm |
| 63 | 2-(((tert-Butoxycarbonyl)amino)methyl)-3-methylbutanoic acid | — | — | Commercially available, CAS: 1233517-91-3 |
| 64 | tert-Butyl (2-(hydroxymethyl)-3-methylbutyl)carbamate | 2 | 63 | LCMS (System 3, Method B): m/z 218 $(M+H)^+$ $(ES^+)$, at 1.54 min, 202 nm |
| 65 | (S)-2-(1-(tert-Butoxycarbonyl)pyrrolidin-2-yl)acetic acid | — | — | Commercially available, CAS: 56502-01-3 |
| 66 | tert-Butyl (S)-2-(2-hydroxyethyl)pyrrolidine-1-carboxylate | 2 | 65 | $^1$H NMR (500 MHZ, Chloroform-d) δ 1.45 (s, 9H), 1.57-1.63 (m, 1H), 1.64-1.72 (m, 1H), 1.82-1.92 (m, 2H), 1.92-2.02 (m, 1H), 3.26-3.36 (m, 2H), 3.50-3.66 (m, 2H), 4.11-4.18 (m, 1H), 4.39 (s, 1H). One exchangeable proton not observed. |
| 67 | tert-Butyl (S)-4-((R)-3-((tert-butoxycarbonyl)(methyl)-amino)pyrrolidin-1-yl)-2-chloro-8-isopropyl-7,8-dihydropyrimido[5,4-b][1,4]oxazepine-9(6H)-carboxylate | B Steps 1 to 5 DCM was used in Step 4 | 2, 56 and 4 | LCMS (System 3, Method B): m/z 526/528 $(M+H)^+$ $(ES^+)$, at 2.29 min, 202 nm |
| 68 | tert-Butyl (R)-4-((R)-3-((tert-butoxycarbonyl)(methyl)-amino)pyrrolidin-1-yl)-2-chloro-8-isopropyl-7,8-dihydropyrimido[5,4-b][1,4]oxazepine-9(6H)-carboxylate | B Steps 1 to 5 DCM was used in Step 4 | 2, 58 and 4 | LCMS (System 3, Method B): m/z 470/472 $(M-56+H)^+$ $(ES^+)$, at 2.19 min, 260 nm |

TABLE 3

Example compounds

| Ex. No. | Name | Synthetic Route and Intermediates Used | Isolation or Purification Method* | $^1$H NMR |
|---|---|---|---|---|
| 1-1 | (R)-4-(3-(Methylamino)pyrrolidin-1-yl)-7,8-dihydro-6H-pyrimido[5,4-b][1,4]oxazin-2-amine | A 1, 3 and 4 | RP-HPLC (basic) | (500 MHz, DMSO-$d_6$) δ 1.54-1.63 (m, 1H), 1.84-1.93 (m, 1H), 2.26 (s, 3H), 3.02-3.09 (m, 1H), 3.22-3.27 (m, 1H), 3.28-3.32 (m, 2H), 3.44-3.51 (m, 1H), 3.52-3.59 (m, 1H), 3.59-3.65 (m, 1H), 3.84-3.90 (m, 2H), 5.05 (s, 2H), 6.18-6.23 (m, 1H). One exchangeable proton not observed. |

TABLE 3-continued

| Example compounds | | | | |
|---|---|---|---|---|
| 1-2 | 7-Methyl-4-((R)-3-(methylamino)pyrrolidin-1-yl)-7,8-dihydro-6H-pyrimido[5,4-b][1,4]oxazin-2-amine | A<br>2, 5 and 4<br>Step 5 omitted | RP-flash (basic) | (500 MHz, DMSO-$d_6$) δ 1.06 (d, J = 6.1 Hz, 3H), 1.54-1.63 (m, 1H), 1.83-1.93 (m, 1H), 2.26 (d, J = 1.2 Hz, 3H), 3.02-3.08 (m, 1H), 3.21-3.26 (m, 1H), 3.40-3.51 (m, 3H), 3.52-3.59 (m, 1H), 3.59-3.65 (m, 1H), 3.88-3.93 (m, 1H), 5.03 (s, 2H), 6.26 (s, 1H). One exchangeable proton not observed. |
| 1-3 | (R)-7-Ethyl-4-((R)-3-(methylamino)pyrrolidin-1-yl)-7,8-dihydro-6H-pyrimido[5,4-b][1,4]oxazin-2-amine dihydrochloride salt | B<br>2, 6 and 4 | RP-flash (neutral) | $^1$H NMR (500 MHz, DMSO-$d_6$) δ 0.93 (t, J = 7.5 Hz, 3H), 1.45-1.59 (m, 2H), 2.12-2.28 (m, 2H), 2.54 (t, J = 5.3 Hz, 3H), 3.41-3.47 (m, 1H), 3.67-3.77 (m, 2H), 3.79-3.84 (m, 1H), 3.85-4.09 (m, 2H), 3.93-3.98 (m, 2H), 7.37 (s, 2H), 8.21 (d, J = 2.9 Hz, 1H), 9.55-9.66 (m, 1H), 9.73 (s, 1H), 11.96 (s, 1H). |
| 1-4 | (R)-7-Isopropyl-4-((R)-3-(methylamino)pyrrolidin-1-yl)-7,8-dihydro-6H-pyrimido [5,4-b][1,4]oxazin-2-amine | A<br>2, 7 and 4<br>No DMF was used in Step 5<br>Step 6 heated for 3 hours to give only one product | RP-HPLC (basic) | $^1$H NMR (400 MHz, DMSO-$d_6$) δ 0.87-0.95 (m, 6H), 1.56-1.66 (m, 1H), 1.73 (h, J = 6.8 Hz, 1H), 1.85-1.94 (m, 1H), 2.27 (s, 3H), 3.05-3.13 (m, 2H), 3.22-3.29 (m, 1H), 3.43-3.51 (m, 1H), 3.52-3.58 (m, 1H), 3.58-3.65 (m, 1H), 3.79 (d, J = 4.0 Hz, 2H), 5.02 (s, 2H), 6.31 (d, J = 3.0 Hz, 1H). One exchangeable proton not observed. |
| 1-5 | (S)-7-Isopropyl-4-((R)-3-(methylamino)pyrrolidin-1-yl)-7,8-dihydro-6H-pyrimido[5,4-b][1,4]oxazin-2-amine | A<br>2, 8 and 4<br>No DMF was used in Step 5 | RP-HPLC (basic) | (500 MHz, DMSO-$d_6$) δ 0.89 (d, J = 6.8 Hz, 3H), 0.92 (d, J = 6.9 Hz, 3H), 1.54-1.62 (m, 1H), 1.65-1.77 (m, 2H), 1.84-1.92 (m, 1H), 2.26 (d, J = 2.3 Hz, 3H), 3.01-3.06 (m, 1H), 3.07-3.11 (m, 1H), 3.21-3.26 (m, 1H), 3.44-3.51 (m, 1H), 3.52-3.58 (m, 1H), 3.58-3.64 (m, 1H), 3.79 (d, J = 4.1 Hz, 2H), 5.01 (s, 2H), 6.30 (d, J = 3.0 Hz, 1H). |
| 1-6 | (R)-7-Cyclopropyl-4-((R)-3-(methylamino)pyrrolidin-1-yl)-7,8-dihydro-6H-pyrimido[5,4-b][1,4]oxazin-2-amine ditrifluoroacetic acid salt | B<br>2, 10 and 4<br>DCM was used in Step 4<br>TFA/DCM was used in Step 7 | RP-HPLC (acidic) | (400 MHz, DMSO-$d_6$) δ 0.28-0.42 (m, 2H), 0.42-0.59 (m, 2H), 0.84-0.96 (m, 1H), 2.00-2.14 (m, 1H), 2.17-2.31 (m, 1H), 2.62 (s, 3H), 2.86-2.95 (m, 1H), 3.64-4.09 (m, 7H), 7.13 (br. s, 2H), 7.89 (br. s, 1H), 8.91 (br. s, 3H). |
| 1-7 | Isomer 2: 7-isobutyl-4-((R)-3-(methylamino)pyrrolidin-1-yl)-7,8-dihydro-6H-pyrimido[5,4-b][1,4]oxazin-2-amine | A<br>2, 11 and 4<br>No DMF was used in Step 5 | RP-HPLC (basic)<br>The two diastereomers were separated | (500 MHz, DMSO-$d_6$) δ 0.89 (d, J = 6.5 Hz, 6H), 1.17-1.24 (m, 1H), 1.34-1.42 (m, 1H), 1.66-1.78 (m, 2H), 1.93-2.01 (m, 1H), 2.36 (s, 3H), 3.21-3.28 (m, 1H), 3.37-3.43 (m, 2H), 3.45-3.52 (m, 1H), 3.56-3.68 (m, 3H), 3.83-3.88 (m, 1H), 5.07 (s, 2H), 6.31- |
| 1-8 | 4-((R)-3-(Methylamino)pyrrolidin-1-yl)-7-(trifluoromethyl)-7,8-dihydro-6H-pyrimido[5,4-b][1,4]oxazin-2-amine | C<br>Example 2-3 | RP-HPLC (basic) | NMR (500 MHz, DMSO-$d_6$) δ 1.58-1.67 (m, 1H), 1.85-1.95 (m, 1H), 2.27 (d, J = 2.7 Hz, 3H), 3.06-3.13 (m, 1H), 3.24-3.29 (m, 1H), 3.45-3.53 (m, 1H), 3.53-3.60 (m, 1H), 3.59-3.69 (m, 2H), 4.15-4.24 (m, 1H), 4.31 (d, J = 12.0 Hz, 1H), 5.24 (s, 2H), 7.04 (d, J = 6.0 Hz, 1H). One exchangeable proton not observed. |
| 1-9 | (R)-7-(Methoxymethyl)-4-((R)-3-(methylamino)pyrrolidin-1-yl)-7,8-dihydro-6H-pyrimido[5,4-b][1,4]oxazin-2-amine | B<br>2, 12 and 4<br>TFA/DCM was used in Step 7 | RP-flash (basic) | (500 MHz, DMSO-$d_6$) δ 1.55-1.63 (m, 1H), 1.84-1.92 (m, 1H), 2.26 (s, 3H), 3.02-3.09 (m, 1H), 3.21-3.27 (m, 1H), 3.27 (s, 3H), 3.28-3.36 (m, 2H), 3.45-3.56 (m, 3H), 3.57-3.65 (m, 1H), 3.71-3.76 (m, 1H), 3.84-3.89 (m, 1H), 5.08 (s, 2H), 6.29 (d, J = 3.4 Hz, 1H). One exchangeable proton not observed. |
| 1-10 | (S)-7-((R)-1-Methoxy-ethyl)-4-((R)-3-(methylamino)pyrrolidin-1-yl)-7,8-dihydro-6H-pyrimido [5,4-b][1,4]oxazin-2-amine dihydrochloride salt | B<br>2, 14 and 4 | RP-flash (neutral) | (500 MHz, DMSO-$d_6$) δ 1.14 (d, J = 6.2 Hz, 3H), 2.12-2.27 (m, 2H), 2.52-2.59 (m, 3H), 3.28 (s, 3H), 3.34-3.40 (m, 1H), 3.44-3.53 (m, 1H), 3.67-3.79 (m, 2H), 3.80-3.86 (m, 1H), 3.86-4.03 (m, 3H), 4.05-4.15 (m, 1H), 7.37 (br. s, 2H), 8.16 (br. s, 1H), 9.37-9.75 (m, 2H), 11.80 (br. s, 1H). |
| 1-11 | (S)-7-((S)-1-Methoxyethyl)-4-((R)-3-(methylamino)pyrrolidin-1-yl)-7,8-dihydro-6H-pyrimido[5,4-b][1,4]oxazin-2-amine dihydrochloride salt | B<br>2, 16 and 4 | RP-flash (neutral) | (500 MHz, DMSO-$d_6$) δ 1.12 (d, J = 6.2 Hz, 3H), 2.09-2.18 (m, 1H), 2.18-2.28 (m, 1H), 2.56 (s, 3H), 3.30 (s, 3H), 3.47-3.55 (m, 1H), 3.64-3.80 (m, 2H), 3.80-4.10 (m, 5H), 7.29 (br. s, 2H), 7.85 (br. s, 1H), 9.19-9.59 (m, 2H), 11.66 (br. s, 1H). One proton obscured by water peak. |
| 1-12 | (S)-7-(2-Methoxypropan-2-yl)-4-((R)-3-(methylamino)pyrrolidin-1-yl)-7,8-dihydro-6H-pyrimido[5,4-b][1,4]oxazin-2-amine | B<br>2, 18 and 4<br>TFA/DCM was used in Step 7 | RP-HPLC (basic) | (500 MHz, DMSO-$d_6$) δ 1.07 (s, 3H), 1.11 (s, 3H), 1.57-1.65 (m, 1H), 1.85-1.93 (m, 1H), 2.27 (s, 3H), 3.05-3.11 (m, 1H), 3.14 (s, 3H), 3.23-3.28 (m, 1H), 3.43-3.50 (m, 1H), 3.53-3.58 (m, 1H), 3.58-3.64 (m, 1H), 3.68-3.73 (m, 1H), 3.96-4.01 (m, 1H), 5.07 (s, 2H), 6.04 (d, J = 3.8 Hz, 1H). Two protons obscured by water peak. |

TABLE 3-continued

Example compounds

| | | | | |
|---|---|---|---|---|
| 1-13 | 4-((R)-3-(Methylamino) pyrrolidin-1-yl)-7-(oxetan-3-yl)-7,8-dihydro-6H-pyrimido[5,4-b][1,4] oxazin-2-amine | D<br>2, 20 and 4 | RP-HPLC (basic) | (500 MHz, DMSO-$d_6$) δ 1.54-1.62 (m, 1H), 1.84-1.92 (m, 1H), 2.25 (s, 3H), 3.00-3.08 (m, 2H), 3.20-3.26 (m, 1H), 3.43-3.49 (m, 1H), 3.51-3.57 (m, 1H), 3.58-3.63 (m, 1H), 3.66-3.73 (m, 3H), 4.41 (t, J = 6.2 Hz, 1H), 4.48 (t, J = 6.1 Hz, 1H), 4.54-4.61 (m, 2H), 5.07 (s, 2H), 6.65-6.69 (m, 1H). One exchangeable proton not observed. |
| 1-14 | (R)-7,7-Dimethyl-4-(3-(methylamino)pyrrolidin-1-yl)-7,8-dihydro-6H-pyrimido[5,4-b][1,4]oxazin-2-amine dihydrochloride salt | E<br>1, 21 and 4 | RP-flash (neutral) | (500 MHz, DMSO-$d_6$) δ 1.21 (s, 6H), 2.06-2.18 (m, 1H), 2.18-2.28 (m, 1H), 2.58 (s, 3H), 3.69 (s, 3H), 3.71-3.99 (m, 5H), 7.64-8.26 (m, 1H), 9.16 (br. s, 2H), 11.56 (br. s, 1H). Two exchangeable protons not observed. |
| 1-15 | 6-Methyl-4-((R)-3-(methylamino)pyrrolidin-1-yl)-7,8-dihydro-6H-pyrimido[5,4-b][1,4] oxazin-2-amine | A<br>2, 22 and 4<br>No DMF was used in Step 5 | RP-flash (basic) | (500 MHz, DMSO-$d_6$) δ 1.21 (d, J = 6.2 Hz, 3H), 1.54-1.64 (m, 1H), 1.72 (s, 1H), 1.83-1.93 (m, 1H), 2.26 (d, J = 2.3 Hz, 3H), 2.92-2.99 (m, 1H), 3.02-3.08 (m, 1H), 3.22-3.28 (m, 1H), 3.28-3.31 (m, 1H), 3.44-3.53 (m, 1H), 3.53-3.59 (m, 1H), 3.59-3.65 (m, 1H), 3.73-3.81 (m, 1H), 5.03 (s, 2H), 6.19 (d, J = 4.3 Hz, 1H). |
| 1-16 | (6S,7R)-6,7-Dimethyl-4-((R)-3-(methylamino) pyrrolidin-1-yl)-7,8-dihydro-6H-pyrimido [5,4-b][1,4]oxazin-2-amine dihydrochloride salt | E<br>1, 23 and 4 | RP-flash (neutral) | (500 MHz, DMSO-$d_6$) δ 1.07 (d, J = 6.5 Hz, 3H), 1.20 (d, J = 6.4 Hz, 3H), 2.19 (d, J = 32.9 Hz, 2H), 2.57 (s, 3H), 3.57-3.64 (m, 1H), 3.65-3.81 (m, 2H), 3.82-4.01 (m, 4H), 7.89-8.25 (m, 2H), 9.17-9.61 (m, 3H), 11.97 (br. s, 1H). |
| 1-17 | (6R,7R)-6,7-Dimethyl-4-((R)-3-(methylamino) pyrrolidin-1-yl)-7,8-dihydro-6H-pyrimido [5,4-b][1,4]oxazin-2-amine dihydrochloride salt | E<br>26 and 4<br>Steps 3, 5, 6 and 7 only | RP-flash (neutral) | (500 MHz, DMSO-$d_6$) δ 1.15 (d, J = 6.5 Hz, 3H), 1.27 (d, J = 6.2 Hz, 3H), 2.11-2.28 (m, 2H), 2.53-2.59 (m, 3H), 3.23-3.31 (m, 1H), 3.53-3.61 (m, 1H), 3.67-3.82 (m, 2H), 3.83-4.05 (m, 3H), 7.33 (br. s, 2H), 7.96 (br. s, 1H), 9.32 (br. s, 1H), 9.56 (br. s, 1H), 11.77 (br. s, 1H). |
| 1-18 | (6S,7S)-6,7-Dimethyl-4-((R)-3-(methylamino)pyrrolidin-1-yl)-7,8-dihydro-6H-pyrimido[5,4-b][1,4] oxazin-2-amine dihydrochloride salt | E<br>1, 27 and 4 | RP-flash (neutral) | (400 MHz, DMSO-$d_6$) δ 1.16 (d, J = 6.4 Hz, 3H), 1.26 (d, J = 6.2 Hz, 3H), 2.06-2.29 (m, 3H), 2.59 (s, 3H), 3.24-3.30 (m, 1H), 3.50-3.63 (m, 1H), 3.65-4.00 (m, 4H), 7.23 (br. s, 2H), 7.73 (br. s, 1H), 8.97-9.26 (m, 2H), 11.48 (br. s, 1H). |
| 1-19 | (6R,7S)-6,7-Dimethyl-4-((R)-3-(methylamino)pyrrolidin-1-yl)-7,8-dihydro-6H-pyrimido [5,4-b][1,4] oxazin-2-amine dihydrochloride salt | E<br>1, 28 and 4 | RP-flash (neutral) | (500 MHz, DMSO-$d_6$) δ 1.07 (d, J = 6.5 Hz, 3H), 1.21 (d, J = 6.4 Hz, 3H), 2.10-2.28 (m, 2H), 2.57 (s, 3H), 3.57-3.65 (m, 1H), 3.67-3.81 (m, 2H), 3.83-4.01 (m, 4H), 7.03-7.43 (m, 2H), 7.89-8.27 (m, 1H), 9.13-9.53 (m, 2H), 11.93 (s, 1H). |
| 1-20 | 7-Isopropyl-8-methyl-4-((R)-3-(methylamino)pyrrolidin-1-yl)-7,8-dihydro-6H-pyrimido[5,4-b][1,4] oxazin-2-amine | F<br>30 | RP-HPLC (basic) | (500 MHz, DMSO-$d_6$) δ 0.89 (d, J = 6.8 Hz, 3H), 0.95 (d, J = 7.0 Hz, 3H), 1.52-1.63 (m, 1H), 1.82-1.94 (m, 1H), 1.95-2.04 (m, 1H), 2.25 (d, J = 4.9 Hz, 3H), 3.00 (s, 3H), 3.02-3.06 (m, 2H), 3.20-3.25 (m, 1H), 3.40-3.47 (m, 1H), 3.47-3.55 (m, 2H), 3.55-3.64 (m, 2H), 4.10-4.16 (m, 1H), 5.12 (s, 2H). |
| 1-21 | 4-((R)-3-(Methylamino)pyrrolidin-1-yl)-6a,7,8,9-tetrahydro-6H-pyrimido[5,4-b] pyrrolo[1,2-d][1,4] oxazin-2-amine | G<br>1, 31 and 4 | RP-flash (basic) | (500 MHz, DMSO-$d_6$) δ 1.33-1.42 (m, 1H), 1.52-1.65 (m, 1H), 1.75-1.85 (m, 1H), 1.85-1.95 (m, 2H), 1.98-2.05 (m, 1H), 2.26 (d, J = 5.6 Hz, 3H), 3.00-3.09 (m, 2H), 3.20-3.28 (m, 1H), 3.40-3.47 (m, 2H), 3.49-3.57 (m, 2H), 3.57-3.63 (m, 1H), 3.64-3.68 (m, 1H), 4.27-4.32 (m, 1H), 5.17 (d, J = 2.8 Hz, 2H). One exchangeable proton not observed. |
| 1-22 | (R)-6a-Methyl-4-((R)-3-(methylamino)pyrrolidin-1-yl)-6a,7,8,9-tetrahydro-6H-pyrimido[5,4-b] pyrrolo[1,2-d][1,4] oxazin-2-amine | G<br>1, 32 and 4 | RP-HPLC (basic) | (500 MHz, DMSO-$d_6$) δ 1.09 (s, 3H), 1.48-1.61 (m, 2H), 1.65-1.81 (m, 2H), 1.82-1.90 (m, 1H), 1.90-2.03 (m, 2H), 2.27 (s, 3H), 3.00 (d, J = 10.0 Hz, 1H), 3.02-3.10 (m, 1H), 3.25-3.31 (m, 2H), 3.45-3.52 (m, 1H), 3.55 (t, J = 7.0 Hz, 2H), 3.59-3.65 (m, 1H), 4.06 (d, J = 10.0 Hz, 1H), 5.15 (s, 2H). |
| 1-23 | (S)-6a-Methyl-4-((R)-3-(methylamino)pyrrolidin-1-yl)-6a,7,8,9-tetrahydro-6H-pyrimido[5,4-b] pyrrolo[1,2-d][1,4] oxazin-2-amine | G<br>1, 33 and 4 | RP-HPLC (basic) | (500 MHz, DMSO-$d_6$) δ 1.09 (s, 3H), 1.49-1.58 (m, 1H), 1.58-1.66 (m, 1H), 1.67-1.76 (m, 1H), 1.74-1.80 (m, 1H), 1.82-1.91 (m, 2H), 1.91-2.03 (m, 1H), 2.26 (s, 3H), 3.00 (d, J = 10.0 Hz, 1H), 3.04-3.10 (m, 1H), 3.22-3.35 (m, 2H), 3.42-3.53 (m, 2H), 3.59-3.64 (m, 1H), 3.65-3.71 (m, 1H), 4.06 (d, J = 9.9 Hz, 1H), 5.14 (s, 2H). |

TABLE 3-continued

Example compounds

| | | | | |
|---|---|---|---|---|
| 2-1 | (R)-4-((R)-3-Aminopyrrolidin-1-yl)-7-ethyl-7,8-dihydro-6H-pyrimido[5,4-dihydrochloride salt | B<br>2, 6 and 34 | RP-flash (neutral) | (400 MHz, DMSO-$d_6$) δ 0.93 (t, J = 7.5 Hz, 3H), 1.46-1.58 (m, 2H), 1.99-2.11 (m, 1H), 2.13-2.25 (m, 1H), 3.42-3.50 (m, 1H), 3.67-3.99 (m, 7H), 7.31 (br. s, 2H), 8.13 (br. s, 1H), 8.47 (br. s, 3H), 11.83 (br. s, 1H). |
| 2-2 | (R)-4-((R)-3-Aminopyrrolidin-1-yl)-7-isopropyl-7,8-dihydro-6H-pyrimido[5,4-b][1,4]oxazin-2-amine dihydrochloride salt | A<br>2, 7 and 34<br>No DMF was used in Step 5<br>Step 6 heated for 3 hours to give only one product HCl/1,4-Dioxane was used in Step 7 | Solid isolated from deprotection step | (500 MHz, DMSO-$d_6$) δ 0.88-0.99 (m, 6H), 1.75-1.84 (m, 1H), 2.01-2.10 (m, 1H), 2.13-2.23 (m, 1H), 3.24-3.31 (m, 1H), 3.68-4.00 (m, 7H), 7.37 (s, 2H), 8.20 (s, 1H), 8.52 (s, 3H).<br>One exchangeable proton not observed. |
| 2-3 | 4-((R)-3-Aminopyrrolidin-1-yl)-7-(trifluoromethyl)-7,8-dihydro-6H-pyrimido[5,4-b][1,4]oxazin-2-amine | A<br>2, 36 and 34<br>No DMF was used in Step 5 | RP-flash (basic) | (500 MHz, DMSO-$d_6$) δ 1.51-1.61 (m, 1H), 1.85-1.94 (m, 1H), 3.17-3.25 (m, 1H), 3.40-3.45 (m, 1H), 3.46-3.54 (m, 1H), 3.56-3.70 (m, 3H), 4.15-4.24 (m, 1H), 4.31 (d, J = 12.1 Hz, 1H), 5.24 (s, 2H), 7.04 (d, J = 6.0 Hz, 1H).<br>Two exchangeable protons not observed. |
| 2-4 | (S)-4-((R)-3-Aminopyrrolidin-1-yl)-7-((R)-1-methoxyethyl)-7,8-dihydro-6H-pyrimido[5,4-b][1,4]oxazin-2-amine dihydrochloride salt | B<br>2, 14 and 34 | RP-flash (neutral) | (500 MHz, DMSO-$d_6$) δ 1.13 (d, J = 6.2 Hz, 3H), 1.98-2.13 (m, 1H), 2.13-2.25 (m, 1H), 3.27 (s, 3H), 3.32-3.38 (m, 1H), 3.45-3.52 (m, 1H), 3.65-3.99 (m, 6H), 4.06-4.12 (m, 1H), 7.38 (br. s, 2H), 8.18 (br. s, 1H), 8.52 (br. s, 3H), 11.85 (br. s, 1H). |
| 2-5 | (S)-4-((R)-3-Aminopyrrolidin-1-yl)-7-((S)-1-methoxyethyl)-7,8-dihydro-6H-pyrimido[5,4-b][1,4]oxazin-2-amine dihydrochloride salt | B<br>2, 16 and 34 | RP-flash (neutral) | (500 MHz, DMSO-$d_6$) δ 1.12 (d, J = 6.2 Hz, 3H), 1.95-2.10 (m, 1H), 2.12-2.25 (m, 1H), 3.30 (s, 3H), 3.33-3.39 (m, 1H), 3.48-3.55 (m, 1H), 3.68-4.05 (m, 7H), 7.25 (br. s, 2H), 7.82 (br. s, 1H), 8.38 (br. s, 3H), 11.68 (br. s, 1H). |
| 2-6 | (S)-4-((R)-3-Aminopyrrolidin-1-yl)-7-(2-methoxypropan-2-yl)-7,8-dihydro-6H-pyrimido[5,4-b][1,4]oxazin-2-amine | B<br>2, 18 and 34<br>TFA/DCM was used in Step 7 | RP-HPLC (basic) | (500 MHz, DMSO-$d_6$) δ 1.07 (s, 3H), 1.11 (s, 3H), 1.46-1.54 (m, 1H), 1.81-1.89 (m, 1H), 3.10-3.14 (m, 1H), 3.14 (s, 3H), 3.30-3.34 (m, 1H), 3.34-3.41 (m, 1H), 3.43-3.49 (m, 1H), 3.55-3.60 (m, 1H), 3.60-3.65 (m, 1H), 3.68-3.74 (m, 1H), 3.96-4.01 (m, 1H), 5.05 (s, 2H), 6.02 (d, J = 3.8 Hz, 1H).<br>Two exchangeable protons not observed. |
| 3-1 | (R)-7-Ethyl-4-(3-(methylamino)azetidin-1-yl)-7,8-dihydro-6H-pyrimido[5,4-b][1,4]oxazin-2-amine ditrifluoroacetic acid salt | B<br>2, 6 and 37<br>TFA/DCM was used in Step 7 | RP-HPLC (acidic) | (400 MHz, DMSO-$d_6$) δ 0.90 (t, J = 7.4 Hz, 3H), 1.44-1.55 (m, 2H), 2.56 (s, 3H), 3.39-3.47 (m, 1H), 3.76-3.82 (m, 1H), 3.89-3.95 (m, 1H), 3.99-4.08 (m, 1H), 4.22 (s, 2H), 4.37-4.51 (m, 2H). Four exchangeable protons not observed. |
| 3-2 | (R)-7-Isopropyl-4-(3-(methylamino)azetidin-1-yl)-7,8-dihydro-6H-pyrimido[5,4-b][1,4]oxazin-2-amine | A<br>2, 7 and 37 | RP-HPLC (basic) | (400 MHz, DMSO-$d_6$) δ 0.86-0.94 (m, 6H), 1.68-1.78 (m, 1H), 2.19 (s, 3H), 3.05-3.11 (m, 1H), 3.37-3.45 (m, 1H), 3.59-3.65 (m, 2H), 3.74-3.83 (m, 2H), 4.00-4.07 (m, 2H), 5.13 (s, 2H), 6.43 (d, J = 2.9 Hz, 1H). One exchangeable proton not observed. |
| 3-3 | (R)-7-Cyclopropyl-4-(3-(methylamino)azetidin-1-yl)-7,8-dihydro-6H-pyrimido[5,4-b][1,4]oxazin-2-amine ditrifluoroacetic acid salt | B<br>2, 10 and 37<br>TFA/DCM was used in Step 7 | RP-HPLC (acidic) | (400 MHz, Methanol-$d_4$) δ 0.32-0.40 (m, 1H), 0.40-0.48 (m, 1H), 0.54-0.70 (m, 2H), 0.87-0.98 (m, 1H), 2.73 (s, 3H), 2.80-2.88 (m, 1H), 3.87-3.95 (m, 1H), 4.09-4.19 (m, 2H), 4.28-4.42 (m, 2H), 4.54-4.68 (m, 2H).<br>Four exchangeable protons not observed. |
| 3-4 | (S)-7-((R)-1-Methoxyethyl)-4-(3-(methylamino)azetidin-1-yl)-7,8-dihydro-6H-pyrimido[5,4-b][1,4]oxazin-2-amine dihydrochloride salt | B<br>2, 14 and 37<br>TFA/DCM was used in Step 7 | TFA salt neutralized using PL-$HCO_3$ MP SPE and converted to HCl salt using 2M aq. HCl | (500 MHz, DMSO-$d_6$) δ 1.13 (d, J = 6.3 Hz, 3H), 2.51 (s, 3H), 3.27 (s, 3H), 3.32-3.39 (m, 1H), 3.44-3.52 (m, 1H), 3.78-3.86 (m, 1H), 3.99-4.11 (m, 2H), 4.25-4.59 (m, 4H), 7.36 (s, 2H), 8.29 (s, 1H), 9.92 (s, 2H). One exchangeable proton not observed. |
| 3-5 | (S)-7-((S)-1-Methoxyethyl)-4-(3-(methylamino)azetidin-1-yl)-7,8-dihydro-6H-pyrimido[5,4-b][1,4]oxazin-2-amine | B<br>2, 16 and 37<br>TFA/DCM was used in Step 7 | RP-HPLC (basic) | (500 MHz, DMSO-$d_6$) δ 1.07 (d, J = 6.2 Hz, 3H), 2.19 (s, 3H), 3.27 (s, 3H), 3.29-3.43 (m, 3H), 3.58-3.64 (m, 2H), 3.77-3.86 (m, 2H), 4.00-4.06 (m, 2H), 5.20 (s, 2H), 6.18 (d, J = 2.7 Hz, 1H).<br>One exchangeable proton not observed. |

TABLE 3-continued

| Example compounds | | | | |
|---|---|---|---|---|
| 3-6 | (S)-7-(2-Methoxypropan-2-yl)-4-(3-(methylamino)azetidin-1-yl)-7,8-dihydro-6H-pyrimido[5,4-b][1,4]oxazin-2-amine | B<br>2, 18 and 37<br>TFA/DCM was used in Step 7 | RP-HPLC (basic) | (500 MHz, DMSO-$d_6$) δ 1.06 (s, 3H), 1.11 (s, 3H), 2.19 (s, 3H), 3.14 (s, 3H), 3.28-3.35 (m, 1H), 3.37-3.43 (m, 1H), 3.58-3.64 (m, 2H), 3.69-3.74 (m, 1H), 3.95-3.99 (m, 1H), 4.00-4.07 (m, 2H), 5.18 (s, 2H), 6.15 (d, J = 3.6 Hz, 1H). One exchangeable proton not observed. |
| 4-1 | (R)-4-(3-Aminoazetidin-1-yl)-7-ethyl-7,8-dihydro-6H-pyrimido[5,4-b][1,4]oxazin-2-amine ditrifluoroacetic acid salt | B<br>2, 6 and 38<br>TFA/DCM was used in Step 7 | RP-HPLC (acidic) | (400 MHz, DMSO-$d_6$) δ 0.92 (t, J = 7.5 Hz, 3H), 1.44-1.57 (m, 2H), 3.76-3.84 (m, 1H), 3.91-3.98 (m, 1H), 4.03-4.22 (m, 3H), 4.36-4.51 (m, 2H), 7.15 (br. s, 2H), 7.99 (br. s, 1H), 8.42 (br. s, 3H), 11.99 (br. s, 1H). One proton obscured by water peak. |
| 4-2 | (R)-4-(3-Aminoazetidin-1-yl)-7-isopropyl-7,8-dihydro-6H-pyrimido[5,4-b][1,4]oxazin-2-amine | A<br>2, 7 and 38<br>No DMF was used in Step 5 | RP-HPLC (basic) | (500 MHz, DMSO-$d_6$) δ 0.87-0.95 (m, 6H), 1.69-1.77 (m, 1H), 3.06-3.11 (m, 1H), 3.50-3.56 (m, 2H), 3.59-3.66 (m, 1H), 3.74-3.82 (m, 2H), 4.03-4.08 (m, 2H), 5.13 (s, 2H), 6.41 (d, J = 2.8 Hz, 1H). Two exchangeable protons not observed. |
| 5-1 | (R)-7-Isopropyl-4-(4-methylpiperazin-1-yl)-7,8-dihydro-6H-pyrimido[5,4-b][1,4]oxazin-2-amine | A<br>2, 7 and 39<br>No DMF was used in Step 5 | RP-HPLC (basic) | $^1$H NMR (500 MHz, DMSO-$d_6$) δ 0.87-0.94 (m, 6H), 1.69-1.78 (m, 1H), 2.16 (s, 3H), 2.27-2.34 (m, 4H), 3.08-3.13 (m, 1H), 3.36-3.47 (m, 4H), 3.80-3.87 (m, 2H), 5.15 (s, 2H), 6.57 (d, J = 3.1 Hz, 1H). |
| 6-1 | (R)-7-Isopropyl-4-(piperazin-1-yl)-7,8-dihydro-6H-pyrimido[5,4-b][1,4]oxazin-2-amine | A<br>2, 7 and 40<br>No DMF was used in Step 5 | RP-HPLC (basic) | (400 MHz, DMSO-$d_6$) δ 0.87-0.95 (m, 6H), 1.68-1.79 (m, 1H), 2.65-2.74 (m, 4H), 3.06-3.13 (m, 1H), 3.32-3.36 (m, 4H), 3.79-3.87 (m, 2H), 5.13 (s, 2H), 6.53 (d, J = 3.0 Hz, 1H). One exchangeable proton not observed. |
| 7-1 | (R)-1-((R)-7-Isopropyl-7,8-dihydro-6H-pyrimido[5,4-b][1,4]oxazin-4-yl)-N-methylpyrrolidin-3-amine | H<br>41 | RP-HPLC (basic) | (500 MHz, Chloroform-d) δ 0.96-1.05 (m, 6H), 1.71-1.85 (m, 2H), 2.04-2.12 (m, 1H), 2.47 (s, 3H), 3.21-3.29 (m, 2H), 3.49-3.54 (m, 1H), 3.67-3.75 (m, 1H), 3.78-3.89 (m, 3H), 4.06-4.11 (m, 1H), 4.94 (s, 1H), 7.81 (s, 1H).<br>One exchangeable proton not observed. |
| 7-2 | (R)-1-((R)-7-Cyclopropyl-7,8-dihydro-6H-pyrimido [5,4-b][1,4]oxazin-4-yl)-N-methylpyrrolidin-3-amine | I<br>42 | RP-HPLC (basic) | (400 MHz, DMSO-$d_6$) δ 0.25-0.36 (m, 2H), 0.36-0.51 (m, 2H), 0.79-0.90 (m, 1H), 1.57-1.70 (m, 1H), 1.85-1.97 (m, 1H), 2.26 (s, 3H), 2.74-2.82 (m, 1H), 3.04-3.13 (m, 1H), 3.30-3.36 (m, 1H), 3.50-3.63 (m, 2H), 3.63-3.70 (m, 1H), 3.81-3.91 (m, 1H), 3.94-4.04 (m, 1H), 6.89 (s, 1H), 7.61 (s, 1H).<br>One exchangeable proton not observed. |
| 7-3 | (3R)-1-(7-(Methoxymethyl)-7,8-dihydro-6H-pyrimido[5,4-b][1,4]oxazin-4-yl)-N-methylpyrrolidin-3-amine | H<br>44 | RP-flash (basic) | (500 MHz, DMSO-$d_6$) δ 1.60-1.67 (m, 1H), 1.74 (br. s, 1H), 1.87-1.95 (m, 1H), 2.26 (s, 3H), 3.06-3.12 (m, 1H), 3.28 (s, 3H), 3.32-3.36 (m, 3H), 3.51-3.58 (m, 1H), 3.58-3.64 (m, 2H), 3.64-3.69 (m, 1H), 3.84-3.89 (m, 1H), 3.93-3.99 (m, 1H), 6.80-6.85 (m, 1H), 7.61 (s, 1H). |
| 7-4 | (R)-1-((S)-7-((R)-1-Methoxyethyl)-7,8-dihydro-6H-pyrimido[5,4-b][1,4]oxazin-4-yl)-N-methylpyrrolidin-3-amine hydrochloride salt | H<br>45<br>HCl/1,4-Dioxane was used in Step 2 | RP-flash (neutral) | (500 MHz, DMSO-$d_6$) δ 1.15 (d, J = 6.2 Hz, 3H), 2.14-2.22 (m, 1H), 2.22-2.30 (m, 1H), 2.58 (t, J = 5.4 Hz, 3H), 3.29 (s, 3H), 3.37-3.43 (m, 1H), 3.56-3.61 (m, 1H), 3.71-3.83 (m, 2H), 3.90-4.01 (m, 4H), 4.17-4.23 (m, 1H), 8.06 (s, 1H), 8.35 (s, 1H), 9.27 (s, 1H), 9.39 (s, 1H). |
| 7-5 | (3R)-N-Methyl-1-(6-methyl-7,8-dihydro-6H-pyrimido [5,4-b][1,4]oxazin-4-yl)pyrrolidin-3-amine | H<br>46 | RP-HPLC (basic) | $^1$H NMR (500 MHz, Chloroform-d) δ 1.32-1.37 (m, 3H), 1.70-1.81 (m, 1H), 2.03-2.13 (m, 1H), 2.47 (d, J = 1.8 Hz, 3H), 3.19-3.24 (m, 1H), 3.24-3.29 (m, 1H), 3.43-3.49 (m, 1H), 3.50-3.56 (m, 1H), 3.69-3.76 (m, 1H), 3.79-3.91 (m, 2H), 4.00-4.08 (m, 1H), 4.75 (s, 1H), 7.82 (d, J = 0.8 Hz, 1H).<br>One exchangeable proton not observed. |
| 8-1 | (R)-1-((R)-7-Isopropyl-7,8-dihydro-6H-pyrimido[5,4-b][1,4]oxazin-4-yl)pyrrolidin-3-amine | H<br>47 | RP-HPLC (basic) | (500 MHz, Chloroform-$d_6$) δ 0.97-1.04 (m, 6H), 1.64-1.73 (m, 1H), 1.75-1.86 (m, 1H), 2.03-2.12 (m, 1H), 3.21-3.27 (m, 1H), 3.40-3.46 (m, 1H), 3.57-3.63 (m, 1H), 3.68-3.75 (m, 1H), 3.80-3.90 (m, 3H), 4.06-4.11 (m, 1H), 4.90 (s, 1H), 7.81 (s, 1H).<br>Two exchangeable protons not observed. |
| 8-2 | (R)-1-((S)-7-((R)-1-Methoxyethyl)-7,8-dihydro-6H-pyrimido[5,4-b][1,4]oxazin-4-yl)pyrrolidin-3-amine hydrochloride salt | H<br>48<br>HCl/1,4-Dioxane was used in Step 2 | RP-flash (neutral) | (500 MHz, DMSO-$d_6$) δ 1.15 (d, J = 6.2 Hz, 3H), 2.07-2.14 (m, 1H), 2.18-2.27 (m, 1H), 3.29 (s, 3H), 3.36-3.44 (m, 1H), 3.58-3.65 (m, 1H), 3.75-3.83 (m, 1H), 3.83-3.89 (m, 1H), 3.89-4.01 (m, 4H), 4.17-4.23 (m, 1H), 8.11 (s, 1H), 8.58 (br. s, 4H). |
| 9-1 | (R)-1-(7-Isopropyl-7,8-dihydro-6H-pyrimido[5,4-b][1,4]oxazin-4-yl)-N-methylazetidin-3-amine | H<br>49 | RP-HPLC (basic) | (500 MHz, Chloroform-d) δ 0.99-1.05 (m, 6H), 1.86-1.94 (m, 1H), 2.81 (s, 3H), 3.39-3.44 (m, 1H), 3.99-4.06 (m, 1H), 4.07-4.12 (m, 1H), 4.13-4.21 (m, 1H), 4.53-4.61 (m, 2H), 4.61-4.70 (m, 2H), 7.94 (s, 1H), 8.45 (s, 1H).<br>One exchangeable proton not observed. |

TABLE 3-continued

| Example compounds | | | | |
|---|---|---|---|---|
| 10-1 | (3R)-1-(7-Isopropyl-2-methyl-7,8-dihydro-6H-pyrimido[5,4-b][1,4]oxazin-4-yl)-N-methylpyrrolidin-3-amine | J 30 | RP-HPLC (basic) | (500 MHz, DMSO-$d_6$) δ 0.88-0.95 (m, 6H), 1.57-1.65 (m, 1H), 1.69-1.79 (m, 1H), 1.85-1.93 (m, 1H), 2.11 (s, 3H), 2.26 (s, 3H), 3.04-3.10 (m, 1H), 3.12-3.16 (m, 1H), 3.27-3.32 (m, 1H), 3.48-3.55 (m, 1H), 3.56-3.61 (m, 1H), 3.61-3.67 (m, 1H), 3.82-3.90 (m, 2H), 6.75 (s, 1H). One exchangeable proton not observed. |
| 11-1 | (R)-4-(3-(Methylamino)pyrrolidin-1-yl)-6,7,8,9-tetrahydropyrimido[5,4-b][1,4]oxazepin-2-amine | A 2, 50 and 4 No DMF was used in Step 5 | RP-HPLC (basic) | (400 MHz, DMSO-$d_6$) δ 1.56-1.68 (m, 1H), 1.79-1.87 (m, 2H), 1.87-1.95 (m, 1H), 2.27 (s, 3H), 3.04-3.10 (m, 2H), 3.20-3.27 (m, 2H), 3.42-3.51 (m, 1H), 3.51-3.57 (m, 1H), 3.57-3.63 (m, 1H), 3.80 (t, J = 5.8 Hz, 2H), 5.20 (s, 2H), 5.52 (s, 1H). One exchangeable proton not observed. |
| 11-2 | (R)-8-Methyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 51 and 4 DCM was used in Step 4 TFA/DCM was used in Step 7 | RP-HPLC (acidic) | (400 MHz, DMSO-$d_6$) δ 1.25 (d, J = 6.6 Hz, 3H), 1.81-1.94 (m, 1H), 1.97-2.13 (m, 2H), 2.19-2.30 (m, 1H), 2.63 (s, 3H), 3.62-3.97 (m, 7H), 4.04-4.14 (m, 1H), 6.82 (br. s, 1H), 7.26 (br. s, 2H), 8.83-9.16 (m, 2H), 11.61 (br. s, 1H). |
| 11-3 | (S)-8-Methyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 52 and 4 DCM was used in Step 4 TFA/DCM was used in Step 7 | RP-HPLC (acidic) | (400 MHz, DMSO-$d_6$) δ 1.25 (d, J = 6.6 Hz, 3H), 1.82-1.94 (m, 1H), 1.97-2.16 (m, 2H), 2.16-2.29 (m, 1H), 2.63 (s, 3H), 3.60-3.98 (m, 7H), 4.02-4.14 (m, 1H), 6.71 (s, 1H), 7.18 (s, 2H), 8.67-8.92 (m, 2H). One exchangeable proton not observed. |
| 11-4 | (R)-8-Ethyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 54 and 4 DCM was used in Step 4 TFA/DCM was used in Step 7 | RP-HPLC (acidic) | (400 MHz, Methanol-$d_4$) δ 1.04 (t, J = 7.4 Hz, 3H), 1.60-1.80 (m, 2H), 1.91-2.03 (m, 1H), 2.10-2.23 (m, 2H), 2.35-2.48 (m, 1H), 2.78 (s, 3H), 3.66-3.75 (m, 1H), 3.80-3.90 (m, 2H), 3.91-4.00 (m, 2H), 4.00-4.10 (m, 2H), 4.15-4.24 (m, 1H). Six exchangeable protons not observed. |
| 11-5 | (S)-8-Isopropyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 56 and 4 DCM was used in Step 4 TFA/DCM was used in Step 7 | RP-HPLC (acidic) | (400 MHz, DMSO-$d_6$) δ 0.94 (t, J = 6.8 Hz, 6H), 1.85-2.03 (m, 3H), 2.05-2.15 (m, 1H), 2.18-2.30 (m, 1H), 2.63 (s, 3H), 3.50-3.58 (m, 1H), 3.60-3.93 (m, 5H), 3.93-4.04 (m, 1H), 4.05-4.15 (m, 1H), 6.67 (br. s, 1H), 7.28 (br. s, 2H), 8.83-9.13 (m, 2H), 11.61 (br. s, 1H). |
| 11-6 | (R)-8-Isopropyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 58 and 4 DCM was used in Step 4 | RP-HPLC (acidic)1.84- | (400 MHz, DMSO-$d_6$) δ 0.94 (t, J = 6.6 Hz, 6H), 2.03 (m, 3H), 2.06-2.16 (m, 1H), 2.17-2.29 (m, 1H), 2.62 (s, 3H), 3.53-3.62 (m, 1H), 3.64-3.93 (m, 5H), 3.95-4.04 (m, 1H), 4.05-4.14 (m, 1H), 6.65 (s, 1H), 7.30 (s, 2H), 8.89 (d, J = 46.1 Hz, 2H), 11.46 (s, 1H). |
| 11-7 | 7-Methyl-4-((R)-3-(methylamino)pyrrolidin-1-yl)-6,7,8,9-tetrahydropyrimido [5,4-b][1,4]oxazepin-2-amine ditrifluoroacetic acid salt | B 2, 59 and 4 DCM was used in Step 4 TFA/DCM was used in Step 7 | RP-HPLC (acidic) | (400 MHz, Methanol-$d_4$) δ 1.00 (d, J = 6.9 Hz, 3H), 2.13-2.25 (m, 1H), 2.30-2.46 (m, 2H), 2.78 (s, 3H), 3.22-3.29 (m, 1H), 3.46-3.55 (m, 1H), 3.62-3.70 (m, 1H), 3.78-3.91 (m, 2H), 3.91-4.08 (m, 3H), 4.18-4.26 (m, 1H). Six exchangeable protons not observed. |
| 11-8 | 7-Ethyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 62 and 4 Step 3 conducted at RT DCM was used in Step 4 TFA/DCM was used in Step 7 | RP-HPLC (acidic) | (400 MHz, Methanol-$d_4$) δ 0.97 (t, J = 7.5 Hz, 3H), 1.33-1.51 (m, 2H), 2.07-2.28 (m, 2H), 2.32-2.48 (m, 1H), 2.77 (s, 3H), 3.32-3.41 (m, 1H), 3.47-3.61 (m, 1H), 3.71-4.13 (m, 6H), 4.16-4.33 (m, 1H). Six exchangeable protons not observed. |

TABLE 3-continued

| Example compounds | | | | |
|---|---|---|---|---|
| 11-9 | 7-Isopropyl-4-((R)-3-(methylamino)pyrrolidin-1-yl)-6,7,8,9-tetrahydropyrimido[5,4-b][1,4]oxazepin-2-amine ditrifluoroacetic acid salt | B 2, 64 and 4 Steps 3 and 5 conducted at RT DCM was used in Step 4 TFA/DCM was used in Step 7 | RP-HPLC (acidic) | (400 MHz, DMSO-$d_6$) δ 0.81-0.95 (m, 6H), 1.56-1.69 (m, 1H), 1.93-2.04 (m, 1H), 2.04-2.16 (m, 1H), 2.16-2.29 (m, 1H), 2.63 (s, 3H), 3.42-3.48 (m, 2H), 3.61-3.70 (m, 1H), 3.72-3.94 (m, 5H), 4.07-4.15 (m, 1H), 7.21 (s, 3H), 8.61-9.28 (m, 2H), 11.87 (s, 1H). |
| 11-10 | (S)-4-((R)-3-(Methylamino)pyrrolidin-1-yl)-6,7,7a,8,9,10-hexahydropyrimido[5,4-b]pyrrolo[1,2-d][1,4]oxazepin-2-amine | K 2, 66 and 4 | RP-flash (neutral) then RP-flash (basic) | (500 MHz, DMSO-$d_6$) δ 1.48-1.57 (m, 1H), 1.59-1.67 (m, 1H), 1.67-1.75 (m, 1H), 1.76-1.84 (m, 1H), 1.84-1.94 (m, 2H), 1.96-2.03 (m, 1H), 2.04-2.11 (m, 1H), 2.26 (s, 3H), 3.04-3.10 (m, 1H), 3.23-3.28 (m, 1H), 3.35-3.42 (m, 2H), 3.44-3.54 (m, 2H), 3.55-3.60 (m, 1H), 3.77-3.84 (m, 1H), 3.84-3.90 (m, 2H), 5.21 (s, 2H). One exchangeable proton not observed. |
| 12-1 | (S)-4-((R)-3-Aminopyrrolidin-1-yl)-8-isopropyl-6,7,8,9-tetrahydropyrimido[5,4-b][1,4]oxazepin-2-amine ditrifluoroacetic acid salt | B 2, 56 and 34 DCM was used in Step 4 TFA/DCM was used in Step 7 | RP-HPLC (acidic) | (400 MHz, DMSO-$d_6$) δ 0.94 (t, J = 6.8 Hz, 6H), 1.82-2.06 (m, 4H), 2.10-2.26 (m, 1H), 3.63-3.92 (m, 6H), 3.94-4.03 (m, 1H), 4.04-4.14 (m, 1H), 6.65 (br. s, 1H), 7.31 (br. s, 2H), 8.14 (br. s, 3H), 11.44 (br. s, 1H). |
| 12-2 | (R)-4-((R)-3-Aminopyrrolidin-1-yl)-8-isopropyl-6,7,8,9-tetrahydropyrimido[5,4-b][1,4]oxazepin-2-amine ditrifluoroacetic acid salt | B 2, 58 and 34 DCM was used in Step 4 | RP-HPLC (acidic) | (400 MHz, DMSO-$d_6$) δ 0.94 (t, J = 6.5 Hz, 6H), 1.83-2.08 (m, 4H), 2.11-2.28 (m, 1H), 3.52-3.62 (m, 1H), 3.64-3.92 (m, 5H), 3.93-4.03 (m, 1H), 4.04-4.14 (m, 1H), 6.60 (br. s, 1H), 7.28 (br. s, 2H), 8.10 (br. s, 3H), 11.35 (br. s, 1H). |
| 13-1 | (S)-8-Isopropyl-4-(3-(methylamino)azetidin-1-yl)-6,7,8,9-tetrahydropyrimido[5,4-b][1,4]oxazepin-2-amine ditrifluoroacetic acid salt | B 2, 56 and 37 DCM was used in Step 4 TFA/DCM was used in Step 7 | RP-HPLC (acidic) | (400 MHz, DMSO-$d_6$) δ 0.93 (t, J = 6.2 Hz, 6H), 1.82-2.05 (m, 3H), 2.59 (s, 3H), 3.46-3.58 (m, 1H), 3.89-4.00 (m, 1H), 4.00-4.13 (m, 2H), 4.14-4.60 (m, 4H), 6.70 (br. s, 1H), 7.27 (br. s, 2H), 9.29 (br. s, 2H). One exchangeable proton not observed. |
| 13-2 | (R)-8-Isopropyl-4-(3-(methylamino)azetidin-1-yl)-6,7,8,9-tetrahydropyrimido[5,4-b][1,4]oxazepin-2-amine ditrifluoroacetic acid salt | B 2, 58 and 37 DCM was used in Step 4 TFA/DCM was used in Step 7 | RP-HPLC (acidic) | (400 MHz, DMSO-$d_6$) δ 0.93 (t, J = 5.9 Hz, 6H), 1.84-2.05 (m, 3H), 2.59 (s, 3H), 3.46-3.55 (m, 1H), 3.81-4.60 (m, 4H), 3.89-3.99 (m, 1H), 4.00-4.13 (m, 2H), 6.63 (br. s, 1H), 7.30 (br. s, 2H), 9.16 (br. s, 2H). One exchangeable proton not observed. |
| 14-1 | (R)-1-((S)-8-Isopropyl-6,7,8,9-tetrahydropyrimido[5,4-b][1,4]oxazepin-4-yl)-N-methylpyrrolidin-3-amine trifluoroacetic acid salt | H 67 | RP-HPLC (acidic) | (400 MHz, DMSO-$d_6$) δ 0.87-0.99 (m, 6H), 1.79-1.90 (m, 1H), 1.91-2.11 (m, 3H), 2.19-2.31 (m, 1H), 2.63 (s, 3H), 3.29-3.38 (m, 1H), 3.61-3.70 (m, 1H), 3.71-3.86 (m, 4H), 3.94-4.04 (m, 1H), 4.12-4.22 (m, 1H), 6.43 (br. s, 1H), 7.89 (s, 1H), 8.73-8.96 (m, 2H). |
| 14-2 | (R)-1-((R)-8-Isopropyl-6,7,8,9-tetrahydropyrimido[5,4-b][1,4]oxazepin-4-yl)-N-methylpyrrolidin-3-amine trifluoroacetic acid salt | H 68 HCl/1,4-Dioxane was used in Step 2 | RP-HPLC (acidic) | (400 MHz, DMSO-$d_6$) δ 0.88-1.00 (m, 6H), 1.87-2.00 (m, 2H), 2.01-2.19 (m, 2H), 2.20-2.31 (m, 1H), 2.64 (s, 3H), 3.49-3.60 (m, 1H), 3.65-3.76 (m, 1H), 3.76-3.86 (m, 3H), 3.87-3.96 (m, 1H), 4.06-4.16 (m, 1H), 4.16-4.24 (m, 1H), 7.20 (s, 1H), 8.09 (s, 1H), 8.68-9.07 (m, 2H). |
| 17-1 | 4-((R)-3-(methylamino)pyrrolidin-1-yl)-6a,7,8,9,9a,10-hexahydro-6H-cyclopenta[e]pyrimido[5,4-b][1,4]oxazepin-2-amine ditrifluoroacetic acid salt | | | |
| 17-2 | 4-((R)-3-aminopyrrolidin-1-yl)-6a,7,8,9,9a, 10-hexahydro-6H-cyclopenta[e]pyrimido[5,4-b][1,4]oxazepin-2-amine | | | |

TABLE 3-continued

| Example compounds | |
|---|---|
| 17-3 | 4-(3-(methylamino)azetidin-1-yl)-6a,7,8,9,9a,10-hexahydro-6H-cyclopenta[e]pyrimido[5,4-b][1,4]oxazepin-2-amine |
| 17-4 | (R)-4'-(3-(methylamino)pyrrolidin-1-yl)-6'H,8'H-spiro[cyclobutane-1,7'-pyrimido[5,4-b][1,4]oxazin]-2'-amine |
| 17-5 | (R)-7,7-dimethyl-4-(3-(methylamino)pyrrolidin-1-yl)-6,7,8,9-tetrahydropyrimido[5,4-b][1,4]oxazepin-2-amine |
| 17-6 | (R)-8-ethyl-4-(3-(methylamino)azetidin-1-yl)-6,7,8,9-tetrahydropyrimido[5,4-b][1,4]oxazepin-2-amine |
| 17-7 | (R)-4-((R)-3-aminopyrrolidin-1-yl)-8-ethyl-6,7,8,9-tetrahydropyrimido[5,4-b][1,4]oxazepin-2-amine dihydrochloride salt |
| 17-8 | (R)-8-ethyl-4-((4aR,7aR)-octahydro-6H-pyrrolo[3,4-b]pyridin-6-yl)-6,7,8,9-tetrahydropyrimido[5,4-b][1,4]oxazepin-2-amine |
| 17-9 | (3R)-1-(8-ethyl-8-methyl-6,7,8,9-tetrahydropyrimido[5,4-b][1,4]oxazepin-4-yl)-N-methylpyrrolidin-3-amine |
| 17-10 | 8-ethyl-8-methyl-4-((R)-3-(methylamino)pyrrolidin-1-yl)-6,7,8,9-tetrahydropyrimido[5,4-b][1,4]oxazepin-2-amine |
| 17-11 | (R)-4'-(3-(methylamino)pyrrolidin-1-yl)-6'H,8'H-spiro[cyclopentane-1,7'-pyrimido[5,4-b][1,4]oxazin]-2'-amine |
| 17-12 | (R)-N-methyl-1-(6'H,8'H-spiro[cyclopentane-1,7'-pyrimido [5,4-b][1,4]oxazin]-4'-yl)pyrrolidin-3-amine |
| 17-13 | (R)-1-(3,3-difluoro-6'H,8'H-spiro[cyclobutane-1,7''-pyrimido[5,4-b][1,4]oxazin]-4'-yl)-N-methylpyrrolidin-3-amine |
| 17-14 | (R)-7-ethyl-7-methyl-4-((R)-3-(methylamino)pyrrolidin-1-yl)-7,8-dihydro-6H-pyrimido[5,4-b][1,4]oxazin-2-amine |
| 17-15 | (R)-3,3-difluoro-4'-(3-(methylamino)pyrrolidin-1-yl)-6'H,8'H-spiro[cyclobutane-1,7'-pyrimido[5,4-b][1,4]oxazin]-2'-amine |

TABLE 3-continued

Example compounds

| Ex. No. | LCMS System and Method | LCMS data |
| --- | --- | --- |
| 1-1 | System 2 Method F | m/z 251 $(M + H)^+$ $(ES^+)$, at 0.78 min, 254 nm |
| 1-2 | System 2 Method F | m/z 265 $(M + H)^+$ $(ES^+)$, at 0.85 min, 254 nm |
| 1-3 | System 2 Method G | m/z 279 $(M + H)^+$ $(ES^+)$, at 0.96 min, 254 nm |
| 1-4 | System 2 Method I | m/z 293 $(M + H)^+$ $(ES^+)$, at 3.04 min, 220 nm |
| 1-5 | System 2 Method F | m/z 293 $(M + H)^+$ $(ES^+)$, at 1.11 min, 254 nm |
| 1-6 | System 4 Method C | m/z 291 $(M + H)^+$ $(ES^+)$, at 2.33 min, 202 nm |
| 1-7 | System 2 Method F | m/z 307 $(M + H)^+$ $(ES^+)$, at 1.28 min, 254 nm |
| 1-8 | System 2 Method I | m/z 319 $(M + H)^+$ $(ES^+)$, at 2.74 min, 220 nm |
| 1-9 | System 2 Method F | m/z 295 $(M + H)^+$ $(ES^+)$, at 1.56 min, 254 nm |
| 1-10 | System 2 Method G | m/z 309 $(M + H)^+$ $(ES^+)$, at 0.89 min, 254 nm |
| 1-11 | System 2 Method G | m/z 309 $(M + H)^+$ $(ES^+)$, at 0.92 min, 254 nm |
| 1-12 | System 2 Method F | m/z 323 $(M + H)^+$ $(ES^+)$, at 0.99 min, 254 nm |
| 1-13 | System 2 Method G | m/z 307 $(M + H)^+$ $(ES^+)$, at 0.72 min, 254 nm |
| 1-14 | System 2 Method G | m/z 279 $(M + H)^+$ $(ES^+)$, at 0.94 min, 254 nm |
| 1-15 | System 2 Method F | m/z 265 $(M + H)^+$ $(ES^+)$, at 0.84 min, 254 nm |

TABLE 3-continued

| Example compounds | | |
|---|---|---|
| 1-16 | System 2 Method G | m/z 279 $(M + H)^+$ $(ES^+)$, at 0.91 min, 254 nm |
| 1-17 | System 2 Method F | m/z 279 $(M + H)^+$ $(ES^+)$, at 0.97 min, 254 nm |
| 1-18 | System 2 Method G | m/z 279 $(M + H)^+$ $(ES^+)$, at 0.94 min, 254 nm |
| 1-19 | System 2 Method G | m/z 279 $(M + H)^+$ $(ES^+)$, at 0.94 min, 254 nm |
| 1-20 | System 2 Method F | m/z 307 $(M + H)^+$ $(ES^+)$, at 1.21 min, 254 nm |
| 1-21 | System 2 Method F | m/z 291 $(M + H)^+$ $(ES^+)$, at 0.97 min, 254 nm |
| 1-22 | System 2 Method F | m/z 305 $(M + H)^+$ $(ES^+)$, at 1.06 min, 254 nm |
| 1-23 | System 2 Method F | m/z 305 $(M + H)^+$ $(ES^+)$, at 1.06 min, 254 nm |
| 2-1 | System 2 Method G | m/z 265 $(M + H)^+$ $(ES^+)$, at 0.87 min, 254 nm |
| 2-2 | System 2 Method G | m/z 279 $(M + H)^+$ $(ES^+)$, at 0.97 min, 254 nm |
| 2-3 | System 2 Method F | m/z 305 $(M + H)^+$ $(ES^+)$, at 0.87 min, 254 nm |
| 2-4 | System 2 Method G | m/z 295 $(M + H)^+$ $(ES^+)$, at 0.80 min, 254 nm |
| 2-5 | System 2 Method G | m/z 295 $(M + H)^+$ $(ES^+)$, at 0.87 min, 254 nm |
| 2-6 | System 2 Method F | m/z 309 $(M + H)^+$ $(ES^+)$, at 0.91 min, 254 nm |
| 3-1 | System 4 Method C | m/z 265 $(M + H)^+$ $(ES^+)$, at 2.21 min, 202 nm |

TABLE 3-continued

| Example compounds | | |
|---|---|---|
| 3-2 | System 2 Method F | m/z 279 $(M + H)^+$ $(ES^+)$, at 0.98 min, 254 nm |
| 3-3 | System 4 Method C | m/z 277 $(M + H)^+$ $(ES^+)$, at 2.36 min, 301 nm |
| 3-4 | System 2 Method G | m/z 295 $(M + H)^+$ $(ES^+)$, at 0.82 min, 254 nm |
| 3-5 | System 2 Method F | m/z 295 $(M + H)^+$ $(ES^+)$, at 0.85 min, 254 nm |
| 3-6 | System 2 Method F | m/z 309 $(M + H)^+$ $(ES^+)$, at 0.90 min, 254 nm |
| 4-1 | System 4 Method C | m/z 251 $(M + H)^+$ $(ES^+)$, at 2.01 min, 202 nm |
| 4-2 | System 2 Method G | m/z 265 $(M + H)^+$ $(ES^+)$, at 0.88 min, 254 nm |
| 5-1 | System 2 Method F | m/z 293 $(M + H)^+$ $(ES^+)$, at 1.11 min, 254 nm |
| 6-1 | System 2 Method I | m/z 279 $(M + H)^+$ $(ES^+)$, at 2.80 min, 220 nm |
| 7-1 | System 2 Method G | m/z 278 $(M + H)^+$ $(ES^+)$, at 1.09 min, 254 nm |
| 7-2 | System 4 Method C | m/z 276 $(M + H)^+$ $(ES^+)$, at 2.39 min, 202 nm |
| 7-3 | System 2 Method F | m/z 280 $(M + H)^+$ $(ES^+)$, at 0.86 min, 254 nm |
| 7-4 | System 2 Method G | m/z 294 $(M + H)^+$ $(ES^+)$, at 0.92 min, 254 nm |
| 7-5 | System 2 Method G | m/z 250 $(M + H)^+$ $(ES^+)$, at 0.88 min, 254 nm |
| 8-1 | System 2 Method G | m/z 264 $(M + H)^+$ $(ES^+)$, at 1.00 min, 254 nm |

TABLE 3-continued

| Example compounds | | | |
|---|---|---|---|
| | 8-2 | System 2 Method G | m/z 280 $(M + H)^+$ $(ES^+)$, at 0.83 min, 254 nm |
| | 9-1 | System 2 Method G | m/z 264 $(M + H)^+$ $(ES^+)$, at 1.02 min, 254 nm |
| | 10-1 | System 2 Method F | m/z 292 $(M + H)^+$ $(ES^+)$, at 1.15 min, 254 nm |
| | 11-1 | System 2 Method F | m/z 265 $(M + H)^+$ $(ES^+)$, at 0.78 min, 254 nm |
| | 11-2 | System 4 Method C | m/z 279 $(M + H)^+$ $(ES^+)$, at 2.09 min, 202 nm |
| | 11-3 | System 4 Method C | m/z 279 $(M + H)^+$ $(ES^+)$, at 2.29 min, 297 nm |
| | 11-4 | System 3 Method A | m/z 293 $(M + H)^+$ $(ES^+)$, at 2.03 min, 310 nm |
| | 11-5 | System 4 Method C | m/z 307 $(M + H)^+$ $(ES^+)$, at 2.57 min, 202 nm |
| | 11-6 | System 3 Method A | m/z 307 $(M + H)^+$ $(ES^+)$, at 2.16 min, 310 nm |
| | 11-7 | System 4 Method C | m/z 279 $(M + H)^+$ $(ES^+)$, at 2.23 min, 202 nm |
| | 11-8 | System 4 Method C | m/z 293 $(M + H)^+$ $(ES^+)$, at 2.28 min, 202 nm |
| | 11-9 | System 4 Method C | m/z 307 $(M + H)^+$ $(ES^+)$, at 2.61 min, 202 nm |
| | 11-10 | System 2 Method F | m/z 305 $(M + H)^+$ $(ES^+)$, at 1.03 min, 254 nm |
| | 12-1 | System 3 Method A | m/z 293 $(M + H)^+$ $(ES^+)$, at 2.21 min, 225 nm |
| | 12-2 | System 3 Method A | m/z 293 $(M + H)^+$ $(ES^+)$, at 2.29 min, 202 nm |

TABLE 3-continued

| Example compounds | | |
|---|---|---|
| 13-1 | System 3 Method A | m/z 293 (M + H)$^+$ (ES$^+$), at 1.94 min, 254 nm |
| 13-2 | System 3 MethodA | m/z 293 (M + H)$^+$ (ES$^+$), at 2.09 min, 202 nm |
| 14-1 | System 3 Method B | m/z 292 (M + H)$^+$ (ES$^+$), at 1.24 min, 240 nm |
| 14-2 | System 3 Method A | m/z 292 (M + H)$^+$ (ES$^+$), at 2.13 min, 241 nm |
| 17-1 | System 5 Method J | m/z 305 (M + H)$^+$ (ES$^+$), at 1.20 min, 226 nm |
| 17-2 | System 5 Method J | m/z 291 (M + H)$^+$ (ES$^+$), at 1.18 min, 226 nm |
| 17-3 | System 5 Method J | m/z 291 (M + H)$^+$ (ES$^+$), 1.21 min, at 225 nm |
| 17-4 | System 5 Method J | m/z 291 (M + H)$^+$ (ES$^+$), at 1.16 min, 226 nm |
| 17-5 | System 5 Method J | m/z 293 (M + H)$^+$ (ES$^+$), at 1.17 min, 229 nm |
| 17-6 | System 5 Method J | m/z 279 (M + H)$^+$ (ES$^+$), at 1.17 min, 225 nm |
| 17-7 | System 5 Method J | m/z 279 (M + H)$^+$ (ES$^+$), at 1.15 min, 226 nm |
| 17-8 | System 5 Method J | m/z 319 (M + H)$^+$ (ES$^+$), at 1.19 min, 229 nm |
| 17-9 | System 5 Method J | m/z 292 (M + H)$^+$ (ES$^+$), at 1.22 min, 235 nm |
| 17-10 | System 5 Method J | m/z 307 (M + H)$^+$ (ES$^+$), at 1.20 min, 226 nm |
| 17-11 | System 5 Method J | m/z 305 (M + H)$^+$ (ES$^+$), at 1.21 min, 228 nm |

TABLE 3-continued

| Example compounds | | |
|---|---|---|
| 17-12 | System 5<br>Method J | m/z 290<br>$(M + H)^+$<br>$(ES^+)$, at<br>1.22 min,<br>234 nm |
| 17-13 | System 5<br>Method J | m/z 312<br>$(M + H)^+$<br>$(ES^+)$, at<br>1.20 min,<br>232 nm |
| 17-14 | System 5<br>Method J | m/z 293<br>$(M + H)^+$<br>$(ES^+)$, at<br>1.19 min,<br>225 nm |
| 17-15 | System 5<br>Method J | m/z 327<br>$(M + H)^+$<br>$(ES^+)$, at<br>1.19 min,<br>225 nm |

*For the purification methods:
basic = using high pH aqueous eluent (with $(NH_4)_2CO_3$ or $NH_4HCO_3$);
acidic = using low pH aqueous eluent (with $HCO_2H$ or TFA);
neutral = using water.

BIOLOGICAL ACTIVITY

H4 Antagonist Functional cAMP Gi Assay

HEKf cells were infected overnight using baculovirus expressing the human H4 receptor, then centrifuged at 1,200 rpm for 5 min, frozen in cell freezing medium (Sigma) and stored at −150° C. On the day of assay, the cells were thawed and resuspended in HBSS with 500 nM IBMX to achieve a density of 1,500 cells/well. H4 ligands were prepared in DMSO and stamped by LabCyte ECHO acoustic dispensing at 25 nL in low volume plates. 10 μL/well cells were plated in the presence of 1 μM forskolin, subjected to centrifugation at 1,200 rpm for 1 min and incubated for 30 min prior to addition of Cisbio cAMP detection reagents to a total volume 20 μL/well. For the antagonist assay, cells were pre-incubated with H4 antagonist ligands for 30 min prior to addition of $EC_{80}$ concentration of histamine and a further 30 min incubation. Following detection reagent addition and shaking at room temperature for 60 min, cAMP accumulation was measured using HTRF on a PheraStar plate reader. $EC_{50}$ values were generated using a 4-parameter logistical fit equation to quantify agonist potencies. Functional antagonist affinity values were generated using the Cheng-Prusoff equation to calculate a $pK_b$value using the antagonist assay data.

H4 Antagonist Functional Dynamic Mass Redistribution Assay

HEKf cells were infected using baculovirus expressing the human H4 receptor, plated into fibronectin-coated EPIC plates at a density of 10,000 cells/well and incubated overnight at 37° C. The medium on cells was changed to 30 μL HBSS with 20 mM HEPES per well and 30 nL DMSO were added per well by LabCyte ECHO acoustic dispensing. Following 2 h equilibration at room temperature, 30 nL of H4 ligands prepared in DMSO were stamped by LabCyte ECHO acoustic dispensing into seeded EPIC plates and cellular dynamic mass redistribution was monitored using a Corning EPIC plate reader. Following 45 min measurement, 30 nL/well of histamine $EC_{80}$ was added and monitored to obtain antagonist assay data. Maximum baseline-corrected responses in pm were used to generate concentration response curves. $EC_{50}$ values were generated using a 4-parameter logistical fit equation to quantify agonist potencies. Functional antagonist affinity values were generated using the Cheng-Prusoff equation to calculate a $pK_b$ value using the antagonist assay data.

hERG Assay hERG assay data was determined by Metrion Biosciences, Cambridge, UK, using the experimental protocols detailed below: A Chinese Hamster Ovary (CHO) cell line stably expressing the human ether-a-go-go related gene was grown and passaged under standard culture conditions. Cells were prepared for assays using dissociation protocols designed to optimise cell health, yield, and seal and assay quality. Test samples were provided as 10 mM stock solutions in 100% DMSO. All sample handling and serial dilutions were performed using glass containers and glass-lined plates. A top working concentration of 30 μM was prepared from the 10 mM sample stock solution using a 1:333-fold dilution into external recording solution (0.3% DMSO v/v). In the single-concentration assay, test samples were screened at 30 μM against a minimum of three separate cells. In the $pIC_{50}$ assay, test samples were screened at 1, 3, 10 and 30 μM against a minimum of three separate cells. Each four-point concentration-response curve was constructed using cumulative double sample additions of each concentration to the same cell.

All experiments were performed on the QPatch gigaseal automated patch clamp platform. The composition of external and internal recording solutions for the QPatch experiments is shown in Table A below. All solutions were filtered (0.2 μm) prior to each experiment.

TABLE A

The composition of external and internal solutions (in mM) used in the hERG study

| Constituent | Intracellular Solution (mM) | Extracellular Solution (mM) |
|---|---|---|
| NaCl | — | 140 |
| KCl | 70 | 2 |
| KF | 60 | — |

TABLE A-continued

| The composition of external and internal solutions (in mM) used in the hERG study | | |
|---|---|---|
| Constituent | Intracellular Solution (mM) | Extracellular Solution (mM) |
| HEPES | 10 | 10 |
| $MgCl_2$ | — | 1 |
| $CaCl_2$ | 1 | 2 |
| Glucose | — | 5 |
| EGTA | 5 | — |
| MgATP | 5 | — |
| pH | 7.2 (KOH) | 7.4 (NaOH) |

All recordings were made in the conventional whole-cell configuration and performed at room temperature (~21° C.) using standard single hole chips (Rchip 1.5-4 MΩ). Series resistance (4-15 MΩ) was compensated by >80%. Currents were elicited from a holding potential of −90 mV using the industry standard "+40/−40" voltage protocol as shown in FIG. 1; this was applied at a stimulus frequency of 0.1 Hz.

On achieving the whole-cell configuration, vehicle (0.3% DMSO v/v in external recording solution) was applied to each cell in two bolus additions with a two-minute recording period between each addition to allow stable recordings to be achieved. Following the vehicle period, either:

i) For the single concentration assay—a single concentration of test sample was applied at 30 μM as five bolus additions per test concentration at two-minute intervals; or ii) For the $pIC_{50}$ assay—four concentrations of test sample were applied from 1 μM to 30 μM as two bolus additions per test concentration at two-minute intervals;

and then the effects on hERG tail current amplitude were measured during the four-minute recording period. For each sweep of the voltage protocol, membrane current and the passive properties of the individual cells were recorded by the QPatch assay software (version 5.0). Peak outward tail current amplitude elicited during the test pulse to −40 mV was measured relative to the instantaneous leak current measured during the initial pre-pulse step to −40 mV. For QC purposes, the minimum current amplitude for the assay is >200 pA peak outward current, measured at the end of the vehicle period. The QPatch analysis software calculates the mean peak current for the last three sweeps at the end of each concentration application period and the data is exported to Excel and interrogated using a bioinformatics suite developed running in Pipeline Pilot (Biovia, USA). The template calculates percent inhibition for each test concentration application period as the reduction in mean peak current or charge relative to the value measured at the end of the control (i.e. vehicle) period. The percent inhibition values from each cell are used to construct concentration-response curves employing a four-parameter logistic fit with 0 and 100% inhibition levels fixed at very low and very high concentrations, respectively, and a free Hill slope factor. The $IC_{50}$ (50% inhibitory concentration) and Hill coefficient are then determined, but only data from cells with Hill slopes within 0.5>nH<2.0 are included. The $IC_{50}$ data reported below represents the mean of at least three separate cells (N≥3). By convention, a test sample that fails to achieve >40% block at the top concentration will yield an ambiguous $IC_{50}$ value due to a poor or unconstrained fit. In this instance an arbitrary $IC_{50}$ value is returned that is 0.5 log unit above the highest concentration tested. For example, if a sample fails to demonstrate a mean inhibition of >40% block at a top concentration of 30 μM then an $IC_{50}$ value of 100 μM is reported, i.e. $pIC_{50}$≤4.0.

The vast majority of examples have been prepared as single enantiomers or single diastereomers. Some compounds however, have been prepared as racemates or mixtures of diastereomers, and occasionally those racemates or diastereomers have been separated into single isomers using the techniques of reversed-phased HPLC, chiral HPLC or chiral SEC. For these particular compounds, isomer assignment (Isomer 1, Isomer 2) is based on the retention time of the compound using the separation technique that was performed in the final isomer separation step. By implication, this could be reversed-phased HPLC, chiral HPLC or chiral SFC retention time, and this will vary from compound to compound.

TABLE 4

| H4 and hERG Activity | | | | |
|---|---|---|---|---|
| | | | hERG Activity | |
| | H4 Antagonist Activity | | | hERG |
| Ex. No. | Human H4 CAMP $fpK_b$ | Human H4 DMR $fpK_b$ | hERG $pIC_{50}$ | % inhibition at 30 μM |
| Thioperamide[1] | 7.2 | 6.5 | — | — |
| JNJ-7777120[2] | 8.0 | 8.5 | 5.4 | — |
| JNJ-39758979[3] | 8.1 | 8.5 | ≤4.0 | — |
| Toreforant[4] | 7.7 | 7.9 | 5.5 | 89 |
| PF-3893787[5] | 9.1 | 9.1 | 5.1 | 67 |
| Compound 61[6] | 9.0 | 9.1 | 5.2 | — |
| Compound 48[7] | 8.1 | 9.0 | 4.5 | 55 |
| 1-1 | 6.3 | — | — | 25 |
| 1-2 | 7.9 | — | — | — |
| 1-3 | 9.0 | — | — | 18 |
| 1-4 | 9.1 | — | ≤4.0 | 20 |
| 1-5 | 7.6 | — | — | 68 |
| 1-6 | 9.2 | — | — | — |
| 1-7 | 7.7 | — | — | — |
| 1-8 | 8.0 | — | — | 19 |
| 1-9 | 8.0 | — | — | 12 |
| 1-10 | 8.2 | — | — | 12 |
| 1-11 | 7.8 | — | — | — |

TABLE 4-continued

| H4 and hERG Activity | | | | |
|---|---|---|---|---|
| | | | hERG Activity | |
| | H4 Antagonist Activity | | | hERG |
| Ex. No. | Human H4 CAMP $fpK_b$ | Human H4 DMR $fpK_b$ | hERG $pIC_{50}$ | % inhibition at 30 μM |
| 1-12 | 8.7 | — | — | 8.3 |
| 1-13 | 7.5 | — | — | — |
| 1-14 | 8.2 | — | — | 11 |
| 1-15 | 6.4 | — | — | 1.5 |
| 1-16 | 7.5 | — | — | — |
| 1-17 | 7.1 | — | — | — |
| 1-18 | 6.5 | — | — | — |
| 1-19 | 7.1 | — | — | — |
| 1-20 | 7.0 | — | — | — |
| 1-21 | 7.9 | — | — | 8.5 |
| 1-22 | 6.6 | — | — | 45 |
| 1-23 | 7.4 | — | — | — |
| 2-1 | 8.5 | — | — | — |
| 2-2 | 9.2 | — | ≤4.0 | — |
| 2-3 | 8.0 | — | — | 28 |
| 2-4 | 7.3 | — | — | — |
| 2-5 | 7.1 | — | — | — |
| 2-6 | 7.7 | — | — | — |
| 3-1 | 8.7 | — | — | — |
| 3-2 | 8.9 | — | ≤4.0 | 26 |
| 3-3 | 8.1 | — | — | — |
| 3-4 | 7.9 | — | — | 12 |
| 3-5 | 7.7 | — | — | — |
| 3-6 | 7.6 | — | — | — |
| 4-1 | 7.1 | — | — | — |
| 4-2 | 7.2 | — | — | — |
| 5-1 | 8.5 | — | — | 44 |
| 6-1 | 8.4 | — | — | 13 |
| 7-1 | 9.2 | — | — | 31 |
| 7-2 | 8.5 | — | — | — |
| 7-3 | 6.5 | — | — | 48 |
| 7-4 | 7.5 | — | — | — |
| 7-5 | 6.6 | — | — | — |
| 8-1 | 8.3 | — | — | 21 |
| 8-2 | 6.2 | — | — | — |
| 9-1 | 8.4 | — | — | 18 |
| 10-1 | 6.4 | — | — | — |
| 11-1 | 6.7 | — | — | — |
| 11-2 | 8.6 | 8.3 | — | 13 |
| 11-3 | 7.5 | 8.0 | — | — |
| 11-4 | 9.2 | 8.9 | ≤4.0 | 39 |
| 11-5 | 9.4 | — | ≤4.0 | 21 |
| 11-6 | 7.9 | — | — | — |
| 11-7 | 6.6 | — | — | — |
| 11-8 | 7.5 | — | — | — |
| 11-9 | 7.2 | 7.3 | — | — |
| 11-10 | 6.1 | — | — | — |
| 12-1 | 9.2 | 8.6 | ≤4.0 | — |
| 12-2 | 7.4 | — | — | |
| 13-1 | 9.0 | 8.8 | ≤4.0 | 15 |
| 13-2 | 7.8 | — | — | — |
| 14-1 | 8.5 | 9.1 | — | 41 |
| 14-2 | 7.0 | — | — | — |
| 17-1 | — | 7.9 | — | 29 |
| 17-2 | — | 7.7 | — | — |
| 17-3 | — | 7.5 | — | 42 |
| 17-4 | — | 8.7 | — | — |
| 17-5 | — | 6.7 | — | — |
| 17-6 | — | 8.0 | — | — |
| 17-7 | — | 8.0 | — | — |
| 17-8 | — | 7.8 | — | — |
| 17-9 | — | 7.4 | — | — |
| 17-10 | — | 8.0 | — | — |
| 17-11 | — | 8.1 | — | — |
| 17-12 | — | 8.1 | — | — |

TABLE 4-continued

H4 and hERG Activity

| | H4 Antagonist Activity | | hERG Activity | |
|---|---|---|---|---|
| | | | | hERG |
| Ex. No. | Human H4 CAMP $fpK_b$ | Human H4 DMR $fpK_b$ | hERG $pIC_{50}$ | % inhibition at 30 μM |
| 17-13 | — | 8.4 | — | — |
| 17-14 | — | 8.1 | — | — |
| 17-15 | — | 8.1 | — | — |

[1]Changlu Liu et al, J Pharmacol Exp Ther., 299, (2001), 121-130.
[2]Jennifer D. Venable et al, J. Med. Chem., 48, (2005), 8289-8298.
[3]Brad M. Savall et al, J. Med. Chem., 57, (2014), 2429-2439.
[4]Robin L Thurmond et al, Ann Pharmacol Pharm., 2, (2017), 1-11.
[5]Charles E. Mowbray et al, Bioorg. Med. Chem. Lett., 21, (2011), 6596-6602.
[6]Rogier A. Smits et al, Bioorg. Med. Chem. Lett., 23, (2013), 2663-2670.
[7]Chan-Hee Park et al, J. Med. Chem., 61, (2018), 2949-2961.

The invention claimed is:

1. A compound of the formula (1):

(1)

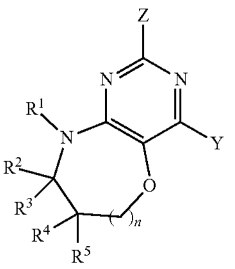

or a salt thereof, wherein;

Z is H, $NH_2$ or $C_{1-3}$ alkyl;

Y is selected from the group consisting of:

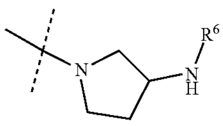 ; 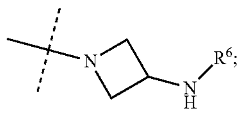

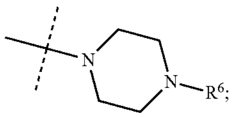 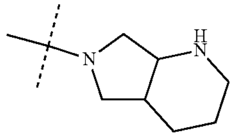 ;

n is 0 or 1;

$R^1$ is H or $C_{1-3}$ alkyl optionally substituted with 1 to 6 fluorine atoms, or is joined to $R^3$ to form a ring which is optionally substituted with 1 to 6 fluorine atoms;

$R^2$ is H, optionally substituted $C_{1-6}$ alkyl, optionally substituted $C_{3-6}$ cycloalkyl, or an optionally substituted 3 to 6-membered heterocyclyl group, wherein the optional substituents are selected from $OC_{1-3}$ alkyl or 1 to 6 fluorine atoms, or $R^2$ is joined to $R^3$ to form a ring which is optionally substituted with 1 to 6 fluorine atoms;

$R^3$ is H or $C_{1-3}$ alkyl optionally substituted with 1 to 6 fluorine atoms, or is joined to $R^1$ to form a ring which is optionally substituted with 1 to 6 fluorine atoms, or is joined to $R^2$ to form a ring which is optionally substituted with 1 to 6 fluorine atoms, or is joined to $R^4$ to form a ring which is optionally substituted with 1 to 6 fluorine atoms;

$R^4$ is H or $C_{1-3}$ alkyl optionally substituted with 1 to 6 fluorine atoms, or is joined to $R^3$ to form a ring which is optionally substituted with 1 to 6 fluorine atoms, or is joined to $R^5$ to form a ring which is optionally substituted with 1 to 6 fluorine atoms;

$R^5$ is H or $C_{1-3}$ alkyl optionally substituted with 1 to 6 fluorine atoms, or is joined to $R^4$ to form a ring which is optionally substituted with 1 to 6 fluorine atoms;

and $R^6$ is H or methyl.

2. The compound according to claim 1 which is a compound of formula (2a) or (2b):

(2a)

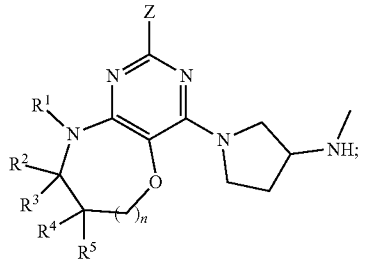

(2b)

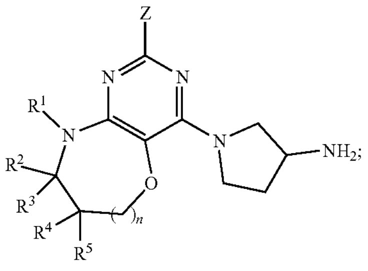

or a salt thereof.

3. The compound according to claim 2 which is a compound of formula (3a) or (3b):

(3a)

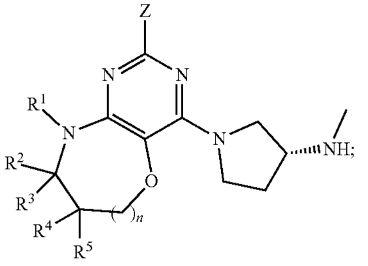

(3b)

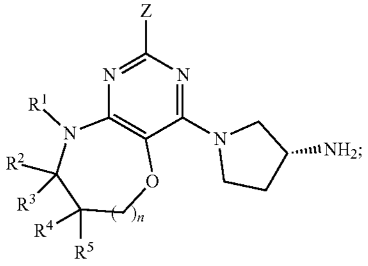

or a salt thereof.

4. The compound according to claim 1 which is a compound of formula (2c) or (2d):

(2c)

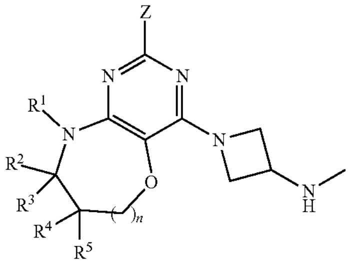

;

(2d)

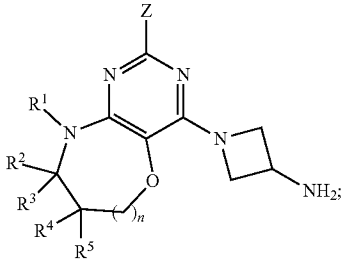

or a salt thereof.

5. The compound according to claim 1 which is a compound of formula (2e):

(2e)

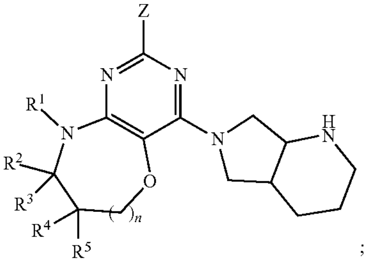

;

or a salt thereof.

6. The compound according to claim 5 which is a compound of formula (3c):

(3c)

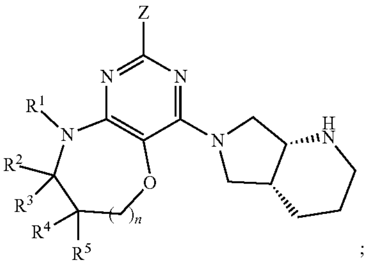

;

or a salt thereof.

7. The compound according to claim 1 which is a compound of formula (4):

(4)

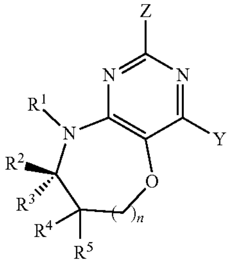

or a salt thereof.

8. The compound according to claim 1, wherein Z is H, $NH_2$ or methyl.

9. The compound according to claim 8, wherein Z is $NH_2$.

10. The compound according to claim 1, wherein $R^1$ is H.

11. The compound according to claim 1, wherein $R^2$ is selected from the group consisting of H, methyl, ethyl, isopropyl, cyclopropyl, isobutyl, trifluoromethyl, $CH_2OMe$, $CH(CH_3)OMe$, $C(CH_3)_2OMe$ and oxetanyl.

12. The compound according to claim 11, wherein $R^2$ is ethyl or isopropyl.

13. The compound according to claim 1, wherein $R^3$ is H or methyl.

14. The compound according to claim 1, wherein $R^2$ is ethyl and $R^3$ is methyl.

15. The compound according to claim 1, wherein $R^4$ is H, methyl, ethyl or isopropyl.

16. The compound according to claim 15, wherein $R^4$ is H.

17. The compound according to claim 1, wherein n is 0.

18. The compound according to claim 1, wherein n is 1.

19. The compound according to claim 1 which is selected from the group consisting of:

(R)-4-(3-(Methylamino)pyrrolidin-1-yl)-7,8-dihydro-6H-pyrimido[5,4-b][1,4]oxazin-2-amine;

7-Methyl-4-((R)-3-(methylamino)pyrrolidin-1-yl)-7,8-dihydro-6H-pyrimido[5,4-b][1,4]oxazin-2-amine;

(R)-7-Ethyl-4-((R)-3-(methylamino)pyrrolidin-1-yl)-7,8-dihydro-6H-pyrimido[5,4-b][1,4]oxazin-2-amine;

(R)-7-Isopropyl-4-((R)-3-(methylamino)pyrrolidin-1-yl)-7,8-dihydro-6H-pyrimido[5,4-b][1,4]oxazin-2-amine;

(S)-7-Isopropyl-4-((R)-3-(methylamino)pyrrolidin-1-yl)-7,8-dihydro-6H-pyrimido[5,4-b][1,4]oxazin-2-amine;

(R)-7-Cyclopropyl-4-((R)-3-(methylamino)pyrrolidin-1-yl)-7,8-dihydro-6H-pyrimido[5,4-b][1,4]oxazin-2-amine;

7-isobutyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-7-(trifluoromethyl)-7,8-dihydro-6H-pyrimido[5,4-b][1,4]oxazin-2-amine;

(R)-7-(Methoxymethyl)-4-((R)-3-(methylamino)pyrrolidin-1-yl)-7,8-dihydro-6H-pyrimido[5,4-b][1,4]oxazin-2-amine;

(S)-7-((R)-1-Methoxyethyl)-4-((R)-3-(methylamino)pyrrolidin-1-yl)-7,8-dihydro-6H-pyrimido[5,4-b][1,4]oxazin-2-amine;

(S)-7-((S)-1-Methoxyethyl)-4-((R)-3-(methylamino)pyrrolidin-1-yl)-7,8-dihydro-6H-pyrimido[5,4-b][1,4]oxazin-2-amine;

(S)-7-(2-Methoxypropan-2-yl)-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-7-(oxetan-3-yl)-7,8-dihydro-6H-pyrimido[5,4-b][1,4]oxazin-2-amine;

(R)-7,7-Dimethyl-4-(3-(methylamino)pyrrolidin-1-yl)-7,8-dihydro-6H-pyrimido[5,4-b][1,4]oxazin-2-amine;

6-Methyl-4-((R)-3-(methylamino)pyrrolidin-1-yl)-7,8-dihydro-6H-pyrimido[5,4-b][1,4]oxazin-2-amine;

(6S,7R)-6,7-Dimethyl-4-((R)-3-(methylamino)pyrrolidin-1-yl)-7,8-dihydro-6H-pyrimido[5,4-b][1,4]oxazin-2-amine;

(6R,7R)-6,7-Dimethyl-4-((R)-3-(methylamino)pyrrolidin-1-yl)-7,8-dihydro-6H-pyrimido[5,4-b][1,4]oxazin-2-amine;

(6S,7S)-6,7-Dimethyl-4-((R)-3-(methylamino)pyrrolidin-1-yl)-7,8-dihydro-6H-pyrimido[5,4-b][1,4]oxazin-2-amine;

(6R,7S)-6,7-Dimethyl-4-((R)-3-(methylamino)pyrrolidin-1-yl)-7,8-dihydro-6H-pyrimido[5,4-b][1,4]oxazin-2-amine;

7-Isopropyl-8-methyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-6a,7,8,9-tetrahydro-6H-pyrimido[5,4-b]pyrrolo[1,2-d][1,4]oxazin-2-amine;

(R)-6a-Methyl-4-((R)-3-(methylamino)pyrrolidin-1-yl)-6a,7,8,9-tetrahydro-6H-pyrimido[5,4-b]pyrrolo[1,2-d][1,4]oxazin-2-amine;

(S)-6a-Methyl-4-((R)-3-(methylamino)pyrrolidin-1-yl)-6a,7, 8,9-tetrahydro-6H-pyrimido[5,4-b]pyrrolo[1,2-d][1,4]oxazin-2-amine;

(R)-4-((R)-3-Aminopyrrolidin-1-yl)-7-ethyl-7,8-dihydro-6H-pyrimido[5,4-b][1,4]oxazin-2-amine;

(R)-4-((R)-3-Aminopyrrolidin-1-yl)-7-isopropyl-7,8-dihydro-6H-pyrimido[5,4-b][1,4]oxazin-2-amine;

4-((R)-3-Aminopyrrolidin-1-yl)-7-(trifluoromethyl)-7,8-dihydro-6H-pyrimido[5,4-b][1,4]oxazin-2-amine;

(S)-4-((R)-3-Aminopyrrolidin-1-yl)-7-((R)-1-methoxyethyl)-7,8-dihydro-6H-pyrimido[5,4-b][1,4]oxazin-2-amine;

(S)-4-((R)-3-Aminopyrrolidin-1-yl)-7-((S)-1-methoxyethyl)-7,8-dihydro-6H-pyrimido[5,4-b][1,4]oxazin-2-amine;

(S)-4-((R)-3-Aminopyrrolidin-1-yl)-7-(2-methoxypropan-2-yl)-7,8-dihydro-6H-pyrimido[5,4-b][1,4]oxazin-2-amine;

(R)-7-Ethyl-4-(3-(methylamino)azetidin-1-yl)-7,8-dihydro-6H-pyrimido[5,4-b][1,4]oxazin-2-amine;

(R)-7-Isopropyl-4-(3-(methylamino)azetidin-1-yl)-7,8-dihydro-6H-pyrimido[5,4-b][1,4]oxazin-2-amine;

(R)-7-Cyclopropyl-4-(3-(methylamino)azetidin-1-yl)-7,8-dihydro-6H-pyrimido[5,4-b][1,4]oxazin-2-amine;

(S)-7-((R)-1-Methoxyethyl)-4-(3-(methylamino)azetidin-1-yl)-7,8-dihydro-6H-pyrimido[5,4-b][1,4]oxazin-2-amine;

(S)-7-((S)-1-Methoxyethyl)-4-(3-(methylamino)azetidin-1-yl)-7,8-dihydro-6H-pyrimido[5,4-b][1,4]oxazin-2-amine;

(S)-7-(2-Methoxypropan-2-yl)-4-(3-(methylamino)azetidin-1-yl)-7,8-dihydro-6H-pyrimido[5,4-b][1,4]oxazin-2-amine;

(R)-4-(3-Aminoazetidin-1-yl)-7-ethyl-7,8-dihydro-6H-pyrimido[5,4-b][1,4]oxazin-2-amine;

(R)-4-(3-Aminoazetidin-1-yl)-7-isopropyl-7,8-dihydro-6H-pyrimido[5,4-b][1,4]oxazin-2-amine (R)-7-Isopropyl-4-(4-methylpiperazin-1-yl)-7,8-dihydro-6H-pyrimido[5,4-b][1,4]oxazin-2-amine;

(R)-7-Isopropyl-4-(piperazin-1-yl)-7,8-dihydro-6H-pyrimido[5,4-b][1,4]oxazin-2-amine;

(R)-1-((R)-7-Isopropyl-7,8-dihydro-6H-pyrimido[5,4-b][1,4]oxazin-4-yl)-N-methylpyrrolidin-3-amine;

(R)-1-((R)-7-Cyclopropyl-7,8-dihydro-6H-pyrimido[5,4-b][1,4]oxazin-4-yl)-N-methylpyrrolidin-3-amine;

(3R)-1-(7-(Methoxymethyl)-7,8-dihydro-6H-pyrimido[5,4-b][1,4]oxazin-4-yl)-N-methylpyrrolidin-3-amine;

(R)-1-((S)-7-((R)-1-Methoxyethyl)-7,8-dihydro-6H-pyrimido[5,4-b][1,4]oxazin-4-yl)-N-methylpyrrolidin-3-amine;

(3R)-N-Methyl-1-(6-methyl-7,8-dihydro-6H-pyrimido[5,4-b][1,4]oxazin-4-yl)pyrrolidin-3-amine;

(R)-1-((R)-7-Isopropyl-7,8-dihydro-6H-pyrimido[5,4-b][1,4]oxazin-4-yl)pyrrolidin-3-amine;

(R)-1-((S)-7-((R)-1-Methoxyethyl)-7,8-dihydro-6H-pyrimido[5,4-b][1,4]oxazin-4-yl)pyrrolidin-3-amine;

(R)-1-(7-Isopropyl-7,8-dihydro-6H-pyrimido[5,4-b][1,4]oxazin-4-yl)-N-methylazetidin-3-amine;

(3R)-1-(7-Isopropyl-2-methyl-7,8-dihydro-6H-pyrimido[5,4-b][1,4]oxazin-4-yl)-N-methylpyrrolidin-3-amine;

(R)-4-(3-(Methylamino)pyrrolidin-1-yl)-6,7,8,9-tetrahydropyrimido[5,4-b][1,4]oxazepin-2-amine;

(R)-8-Methyl-4-((R)-3-(methylamino)pyrrolidin-1-yl)-6,7,8,9-tetrahydropyrimido[5,4-b][1,4]oxazepin-2-amine;

(S)-8-Methyl-4-((R)-3-(methylamino)pyrrolidin-1-yl)-6,7,8,9-tetrahydropyrimido[5,4-b][1,4]oxazepin-2-amine;

(R)-8-Ethyl-4-((R)-3-(methylamino)pyrrolidin-1-yl)-6,7,8,9-tetrahydropyrimido[5,4-b][1,4]oxazepin-2-amine;

(S)-8-Isopropyl-4-((R)-3-(methylamino)pyrrolidin-1-yl)-6,7, 8,9-tetrahydropyrimido[5,4-b][1,4]oxazepin-2-amine;

(R)-8-Isopropyl-4-((R)-3-(methylamino)pyrrolidin-1-yl)-6,7,8,9-tetrahydropyrimido[5,4-b][1,4]oxazepin-2-amine;

7-Methyl-4-((R)-3-(methylamino)pyrrolidin-1-yl)-6,7,8,9-tetrahydropyrimido[5,4-b][1,4]oxazepin-2-amine;

7-Ethyl-4-((R)-3-(methylamino)pyrrolidin-1-yl)-6,7,8,9-tetrahydropyrimido[5,4-b][1,4]oxazepin-2-amine;

7-Isopropyl-4-((R)-3-(methylamino)pyrrolidin-1-yl)-6,7,8,9-tetrahydropyrimido[5,4-b][1,4]oxazepin-2-amine;

(S)-4-((R)-3-(Methylamino)pyrrolidin-1-yl)-6,7,7a,8,9,10-hexahydropyrimido[5,4-b]pyrrolo[1,2-d][1,4]oxazepin-2-amine;

(S)-4-((R)-3-Aminopyrrolidin-1-yl)-8-isopropyl-6,7,8,9-tetrahydropyrimido[5,4-b][1,4]oxazepin-2-amine;

(R)-4-((R)-3-Aminopyrrolidin-1-yl)-8-isopropyl-6,7,8,9-tetrahydropyrimido[5,4-b][1,4]oxazepin-2-amine;

(S)-8-Isopropyl-4-(3-(methylamino)azetidin-1-yl)-6,7,8,9-tetrahydropyrimido[5,4-b][1,4]oxazepin-2-amine;

(R)-8-Isopropyl-4-(3-(methylamino)azetidin-1-yl)-6,7,8,9-tetrahydropyrimido[5,4-b][1,4]oxazepin-2-amine;

(R)-1-((S)-8-Isopropyl-6,7,8,9-tetrahydropyrimido[5,4-b][1,4]oxazepin-4-yl)-N-methylpyrrolidin-3-amine;

(R)-1-((R)-8-Isopropyl-6,7,8,9-tetrahydropyrimido[5,4-b][1,4]oxazepin-4-yl)-N-methylpyrrolidin-3-amine;

4-[(3R)-3-(methylamino)pyrrolidin-1-yl]-6a,7, 8,9,9a,10-hexahydro-6H-cyclopenta[e]pyrimido[5,4-b][1,4]oxazepin-2-amine;

4-[(3R)-3-aminopyrrolidin-1-yl]-6a,7, 8,9,9a,10-hexahydro-6H-cyclopenta[e]pyrimido[5,4-b][1,4]oxazepin-2-amine;

4-[3-(methylamino)azetidin-1-yl]-6a,7, 8,9,9a,10-hexahydro-6H-cyclopenta[e]pyrimido[5,4-b][1,4]oxazepin-2-amine;

4'-[(3R)-3-(methylamino)pyrrolidin-1-yl]-6'H,8'H-spiro[cyclobutane-1,7'-pyrimido[5,4-b][1,4]oxazin]-2'-amine;

7,7-dimethyl-4-[(3R)-3-(methylamino)pyrrolidin-1-yl]-6,7,8,9-tetrahydropyrimido[5,4-b][1,4]oxazepin-2-amine;

8-ethyl-4-[3-(methylamino)azetidin-1-yl]-6,7,8,9-tetrahydropyrimido[5,4-b][1,4]oxazepin-2-amine;

4-[(3R)-3-aminopyrrolidin-1-yl]-8-ethyl-6,7,8,9-tetrahydropyrimido[5,4-b][1,4]oxazepin-2-amine;

8-ethyl-4-[(4aR,7aR)-octahydro-6H-pyrrolo[3,4-b]pyridin-6-yl]-6,7,8,9-tetrahydropyrimido[5,4-b][1,4]oxazepin-2-amine;

(3R)-1-(8-ethyl-8-methyl-6,7,8,9-tetrahydropyrimido[5,4-b][1,4]oxazepin-4-yl)-N-methylpyrrolidin-3-amine;

8-ethyl-8-methyl-4-[(3R)-3-(methylamino)pyrrolidin-1-yl]-6,7,8,9-tetrahydropyrimido[5,4-b][1,4]oxazepin-2-amine;

4'-[(3R)-3-(methylamino)pyrrolidin-1-yl]-6'H,8'H-spiro[cyclopentane-1,7'-pyrimido[5,4-b][1,4]oxazin]-2'-amine;

(3R)-N-methyl-1-(6'H,8'H-spiro[cyclopentane-1,7'-pyrimido[5,4-b][1,4]oxazin]-4'-yl)pyrrolidin-3-amine;

(3R)-1-(3,3-difluoro-6'H,8'H-spiro[cyclobutane-1,7'-pyrimido[5,4-b][1,4]oxazin]-4'-yl)-N-methylpyrrolidin-3-amine;

7-ethyl-7-methyl-4-[(3R)-3-(methylamino)pyrrolidin-1-yl]-7,8-dihydro-6H-pyrimido[5,4-b][1,4]oxazin-2-amine; and 3,3-difluoro-4'-[(3R)-3-(methylamino)pyrrolidin-1-yl]-6'H,8'H-spiro[cyclobutane-1,7'-pyrimido[5,4-b][1,4]oxazin]-2'-amine;

or a salt thereof.

20. The compound according to claim 19 which is selected from the group consisting of:

(R)-4-(3-(Methylamino)pyrrolidin-1-yl)-7,8-dihydro-6H-pyrimido[5,4-b][1,4]oxazin-2-amine;

(R)-7-Ethyl-4-((R)-3-(methylamino)pyrrolidin-1-yl)-7,8-dihydro-6H-pyrimido[5,4-b][1,4]oxazin-2-amine;

(R)-7-Isopropyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-7-(trifluoromethyl)-7, 8-dihydro-6H-pyrimido[5,4-b][1,4]oxazin-2-amine;

(R)-7-(Methoxymethyl)-4-((R)-3-(methylamino)pyrrolidin-1-yl)-7,8-dihydro-6H-pyrimido[5,4-b][1,4]oxazin-2-amine;

(S)-7-((R)-1-Methoxyethyl)-4-((R)-3-(methylamino)pyrrolidin-1-yl)-7,8-dihydro-6H-pyrimido[5,4-b][1,4]oxazin-2-amine;

(S)-7-(2-Methoxypropan-2-yl)-4-((R)-3-(methylamino)pyrrolidin-1-yl)-7,8-dihydro-6H-pyrimido[5,4-b][1,4]oxazin-2-amine;

(R)-7,7-Dimethyl-4-(3-(methylamino)pyrrolidin-1-yl)-7,8-dihydro-6H-pyrimido[5,4-b][1,4]oxazin-2-amine;

6-Methyl-4-((R)-3-(methylamino)pyrrolidin-1-yl)-7,8-dihydro-6H-pyrimido[5,4-b][1,4]oxazin-2-amine;

4-((R)-3-(Methylamino)pyrrolidin-1-yl)-6a,7,8,9-tetrahydro-6H-pyrimido[5,4-b]pyrrolo[1,2-d][1,4]oxazin-2-amine;

(R)-4-((R)-3-Aminopyrrolidin-1-yl)-7-isopropyl-7, 8-dihydro-6H-pyrimido[5,4-b][1,4]oxazin-2-amine;

4-((R)-3-Aminopyrrolidin-1-yl)-7-(trifluoromethyl)-7,8-dihydro-6H-pyrimido[5,4-b][1,4]oxazin-2-amine;

(R)-7-Isopropyl-4-(3-(methylamino)azetidin-1-yl)-7,8-dihydro-6H-pyrimido[5,4-b][1,4]oxazin-2-amine;

(S)-7-((R)-1-Methoxyethyl)-4-(3-(methylamino)azetidin-1-yl)-7,8-dihydro-6H-pyrimido[5,4-b][1,4]oxazin-2-amine;

(R)-7-Isopropyl-4-(piperazin-1-yl)-7,8-dihydro-6H-pyrimido[5,4-b][1,4]oxazin-2-amine;

(R)-1-((R)-7-Isopropyl-7,8-dihydro-6H-pyrimido[5,4-b][1,4]oxazin-4-yl)pyrrolidin-3-amine;

(R)-8-Methyl-4-((R)-3-(methylamino)pyrrolidin-1-yl)-6,7, 8,9-tetrahydropyrimido[5,4-b][1,4]oxazepin-2-amine;

(S)-8-Isopropyl-4-((R)-3-(methylamino)pyrrolidin-1-yl)-6,7,8,9-tetrahydropyrimido[5,4-b][1,4]oxazepin-2-amine;

(S)-4-((R)-3-Aminopyrrolidin-1-yl)-8-isopropyl-6,7,8,9-tetrahydropyrimido[5,4-b][1,4]oxazepin-2-amine; and (S)-8-Isopropyl-4-(3-(methylamino)azetidin-1-yl)-6,7,8,9-tetrahydropyrimido[5,4-b][1,4]oxazepin-2-amine;

or a salt thereof.

21. The compound according to claim 1 having H4 receptor activity.

22. The compound according to claim 21 which exhibits low hERG activity.

23. A pharmaceutical composition comprising a compound as defined in claim 1 and a pharmaceutically acceptable excipient.

24. A method of treating an inflammatory disorder in a subject in need thereof comprising administering an effective therapeutic amount of a compound according to claim 1 to said subject.

25. The method of claim 24, wherein said inflammatory disorder is selected from the group consisting of asthma, chronic pruritus, dermatitis, rheumatoid arthritis, gastric ulcerogenesis and colitis.

* * * * *